(12) United States Patent
Park et al.

(10) Patent No.: US 11,696,497 B2
(45) Date of Patent: Jul. 4, 2023

(54) ORGANIC LIGHT EMITTING DEVICE

(71) Applicant: LG Display Co., Ltd., Seoul (KR)

(72) Inventors: Heejun Park, Paju-si (KR); Seonkeun Yoo, Gunpo-si (KR); Soyoung Jang, Seoul (KR); Jicheol Shin, Seoul (KR); Sangbeom Kim, Paju-si (KR); Sunghoon Kim, Seoul (KR); Tae Wan Lee, Seoul (KR); Seong-Min Park, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 633 days.

(21) Appl. No.: 16/724,057

(22) Filed: Dec. 20, 2019

(65) Prior Publication Data

US 2020/0203620 A1 Jun. 25, 2020

(30) Foreign Application Priority Data

Dec. 21, 2018 (KR) ........................ 10-2018-0167667

(51) Int. Cl.

| | |
|---|---|
| *H01L 51/50* | (2006.01) |
| *H10K 85/60* | (2023.01) |
| *C07D 333/76* | (2006.01) |
| *C07D 409/04* | (2006.01) |
| *C07D 307/77* | (2006.01) |
| *H10K 50/18* | (2023.01) |
| *H10K 50/15* | (2023.01) |
| *H10K 50/844* | (2023.01) |
| *H10K 59/123* | (2023.01) |

(52) U.S. Cl.
CPC ......... *H10K 85/636* (2023.02); *C07D 307/77* (2013.01); *C07D 333/76* (2013.01); *C07D 409/04* (2013.01); *H10K 85/633* (2023.02); *H10K 50/156* (2023.02); *H10K 50/18* (2023.02); *H10K 50/844* (2023.02); *H10K 59/123* (2023.02); *H10K 85/615* (2023.02); *H10K 85/6574* (2023.02); *H10K 85/6576* (2023.02)

(58) Field of Classification Search
None
See application file for complete search history.

(56) References Cited

U.S. PATENT DOCUMENTS

| | | | |
|---|---|---|---|
| 9,065,060 B2 | 6/2015 | Hong et al. | |
| 2006/0124924 A1* | 6/2006 | Suh | ..................... H01L 51/0545 257/40 |
| 2016/0056387 A1 | 2/2016 | Kim et al. | |
| 2017/0256722 A1 | 9/2017 | Shim et al. | |
| 2018/0083197 A1* | 3/2018 | Park | ..................... C07D 307/77 |
| 2018/0186764 A1 | 7/2018 | Jung et al. | |

(Continued)

FOREIGN PATENT DOCUMENTS

| | | | |
|---|---|---|---|
| CN | 103119125 A | 5/2013 | |
| CN | 103189469 A | 7/2013 | |
| CN | 103403125 A | 11/2013 | |

(Continued)

*Primary Examiner* — Gregory D Clark
(74) *Attorney, Agent, or Firm* — Seed IP Law Group LLP

(57) ABSTRACT

The present disclosure provides a novel compound and an organic light-emitting device comprising the same. When the novel compound is applied as a hole transport material to an organic light emitting device, the novel compound allows the device to have improved drive voltage, efficiency and lifespan characteristics.

20 Claims, 2 Drawing Sheets

(56) References Cited

U.S. PATENT DOCUMENTS

2019/0185411 A1    6/2019  Lee et al.

FOREIGN PATENT DOCUMENTS

| | | |
|---|---|---|
| CN | 106687444 A | 5/2017 |
| CN | 107849000 A | 3/2018 |
| CN | 108341795 A | 7/2018 |
| DE | 112019002827 T5 | 3/2021 |
| KR | 10-2016-0149879 A | 12/2016 |
| KR | 10-1789998 B1 | 10/2017 |
| KR | 10-2017-0130737 A | 11/2017 |

* cited by examiner

ORGANIC LIGHT EMITTING DEVICE

CROSS-REFERENCE TO RELATED APPLICATION

This application claims the priority of Korean Patent Application No. 10-2018-0167667 filed on Dec. 21, 2018 in the Korean Intellectual Property Office, the disclosure of which is hereby incorporated by reference in its entirety.

BACKGROUND

Technical Field

The present disclosure relates to a novel compound and an organic light-emitting device comprising the same.

Description of the Related Art

As a display device becomes larger recently, a flat display device with good space utilization is getting more attention. One of such flat display devices may include an organic light-emitting display device including an organic light-emitting diode (OLED). The organic light-emitting display device is rapidly developing.

In the organic light-emitting diode (OLED), when charges are injected into a light-emitting layer formed between a first electrode and a second electrode to form paired electrons and holes to form excitons, exciton energy is converted to light for emission. The organic light emitting diode may be driven at a lower voltage and has a relatively low power consumption than a conventional display device. The organic light emitting diode may have advantages of having excellent color rendering and being able to be applied to a flexible substrate for various applications.

BRIEF SUMMARY

One purpose of the present disclosure is to provide a novel compound of a novel structure that is stable materially and has high hole mobility.

Another purpose of the present disclosure is to develop an organic light-emitting device with high efficiency, low power consumption and long lifespan by applying the novel compound to a hole transport layer or an auxiliary hole transport layer of the organic light-emitting device.

The purposes of the present disclosure are not limited to the above-mentioned purposes. Other purposes and advantages of the present disclosure, as not mentioned above, may be understood from the following descriptions and more clearly understood from the embodiments of the present disclosure. Further, it will be readily appreciated that the objects and advantages of the present disclosure may be realized by features and combinations thereof as disclosed in the claims.

According to an aspect of the present disclosure, there is provided a compound represented by the following Chemical Formula 1:

[Chemical Formula 1]

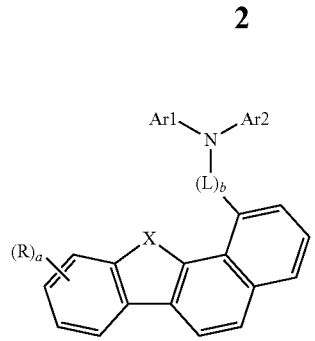

in the Chemical Formula 1,

X is O or S,

R represents one selected from the group consisting of an aryl group having 6 to 30 carbon atoms, an amino group, a heterocyclic group having 3 to 30 carbon atoms and including at least one hetero atom selected from the group consisting of O, N and S, an alkyl group having 1 to 30 carbon atoms, an alkenyl group having 2 to 30 carbon atoms, an alkynyl group having 2 to 30 carbon atoms, an alkoxy group having 1 to 30 carbon atoms, and an aryloxy group having 6 to 30 carbon atoms, a is an integer from 0 to 4, provided that when a is 2 or greater, each R is the same as or different from each other, or adjacent R groups are bonded to each other to form a ring, L represents a direct bond or represents one selected from the group consisting of substituted or unsubstituted arylene having 6 to 30 carbon atoms and substituted or unsubstituted heteroarylene having 3 to 30 carbon atoms, b is an integer from 0 to 4, and each of Ar1 and Ar2 independently represents one selected from the group consisting of a substituted or unsubstituted C6 to C60 aryl group, a C3 to C30 heteroaromatic ring containing at least one heteroatom selected from the group consisting of O, N and S, an alkyl group having 1 to 30 carbon atoms, an alkenyl group having 2 to 30 carbon atoms, an alkynyl group having 2 to 30 carbon atoms, an alkoxyl group having 1 to 30 carbon atoms, and an aryloxy group having from 6 to 30 carbon atoms.

In another aspect of the present disclosure, there is provided an organic light-emitting device that includes a first electrode, a second electrode, and at least one organic material layer between the first and second electrodes, wherein the organic material layer contains a compound represented by the Chemical Formula 1.

The organic light-emitting device according to the present disclosure may have improved drive voltage, efficiency and lifespan.

Further specific effects of the present disclosure as well as the effects as described above will be described in conjunction with illustrations of specific details for carrying out the present disclosure.

DETAILED DESCRIPTION

Figure 1:
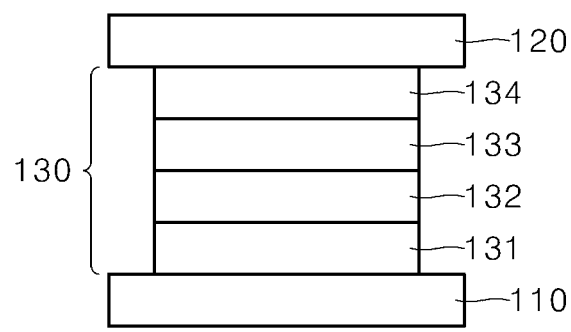
FIG. 1 is a schematic cross-sectional view of an organic light-emitting device incorporating the compound represented by the Chemical Formula 1 according to one embodiment of the present disclosure.

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expressions such as "at least one of," when preceding a list of elements, may modify the entire list of elements and may not modify certain individual elements of the list.

It will be understood that, although the terms "first," "second," "third," and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a term "unsubstituted" means that a hydrogen atom has not been substituted. In this case, the hydrogen atom includes protium, deuterium and tritium. As used herein, a substituent in the term "substituted" may include one selected from the group consisting of, for example, an alkyl group of 1 to 20 carbon atoms unsubstituted or substituted with halogen, an alkoxy group having 1 to 20 carbon atoms unsubstituted or substituted with halogen, halogen, a cyano group, a carboxy group, a carbonyl group, an amine group, an alkylamine group having 1 to 20 carbon atoms, a nitro group, an alkylsilyl group having 1 to 20 carbon atoms, an alkoxysilyl group having 1 to 20 carbon atoms, a cycloalkylsilyl group having 3 to 30 carbon atoms, an arylsilyl group having 6 to 30 carbon atoms, an aryl group having 6 to 30 carbon atoms, an arylamine group having 6 to 20 carbon atoms, a heteroaryl group having 4 to 30 carbon atoms, and a combination thereof. However, the present disclosure is not limited thereto.

As used herein, a term "alkyl" means any alkyl including a straight chain alkyl, and branched chain alkyl.

As used herein, a term "heterocyclic ring" includes a hetero aromatic ring and a hetero alicyclic ring. Each of the "hetero aromatic ring" and the "hetero alicyclic ring" may contain a single ring or a polycyclic ring.

As used herein, the term "hetero" as used in the term 'hetero ring', 'hetero aromatic ring', or 'hetero alicyclic ring' means that one or more carbon atoms, for example, 1 to 5 carbon atoms among carbon atoms constituting the aromatic or alicyclic ring are substituted with at least one hetero atom selected from the group consisting of N, O, S and combinations thereof.

Further, as used herein, each of the terms "hetero ring," "hetero aromatic ring" and "hetero alicyclic ring" includes a single ring and a polycyclic ring. Further, each of the terms "hetero ring," "hetero aromatic ring" and "hetero alicyclic ring" includes at least two single rings as in biphenyl.

As used herein, the phase "combination thereof" as used in the definition of the substituent means that two or more substituents may be bonded to each other via a linking group or two or more substituents may be bonded to each other via condensation, unless otherwise defined.

Hereinafter, the present disclosure describes a novel compound according to some embodiments of the present disclosure, and an organic electro-luminescent device including the compound.

According to one implementation of the present disclosure, there is provided a compound represented by the following Chemical Formula 1:

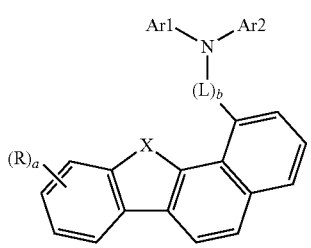

[Chemical Formula 1]

in the Chemical Formula 1,

X is O or S,

R represents one selected from the group consisting of an aryl group having 6 to 30 carbon atoms, an amino group, a heterocyclic group having 3 to 30 carbon atoms and including at least one hetero atom selected from the group consisting of O, N and S, an alkyl group having 1 to 30 carbon atoms, an alkenyl group having 2 to 30 carbon atoms, an alkynyl group having 2 to 30 carbon atoms, an alkoxy group having 1 to 30 carbon atoms, and an aryloxy group having 6 to 30 carbon atoms, a is an integer from 0 to 4, provided that when a is 2 or greater, each R is the same as or different from each other, or adjacent R groups may be bonded to each other to form a ring, L represents a direct bond or represents one selected from the group consisting of substituted or unsubstituted arylene having 6 to 30 carbon atoms and substituted or unsubstituted heteroarylene having 3 to 30 carbon atoms, b is an integer of 0 to 4, and each of Ar1 and Ar2 independently represents one selected from the group consisting of a substituted or unsubstituted C6 to C60 aryl group, a C3 to C30 heteroaromatic ring containing at least one heteroatom selected from the group consisting of O, N and S, an alkyl group having 1 to 30 carbon atoms, an alkenyl group having 2 to 30 carbon atoms, an alkynyl group having 2 to 30 carbon atoms, an alkoxyl group having 1 to 30 carbon atoms, and an aryloxy group having from 6 to 30 carbon atoms.

When the adjacent R groups are bonded to each other to form a ring, the ring may include an alicyclic or aromatic, single or polycyclic ring-based, saturated or unsaturated ring having 5 to 30 carbon atoms.

For example, when R is an aryl group, R may be a fluorenyl group.

In one embodiment, each of Ar1 and Ar2 in the Chemical Formula 1 may be selected from following substituents.

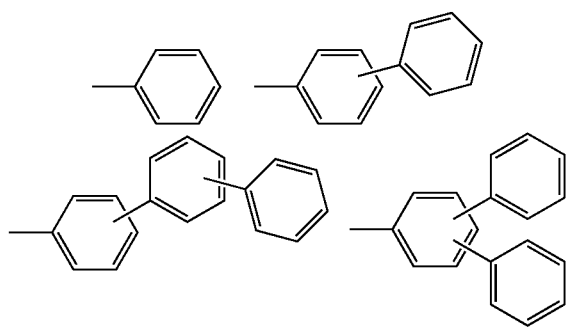

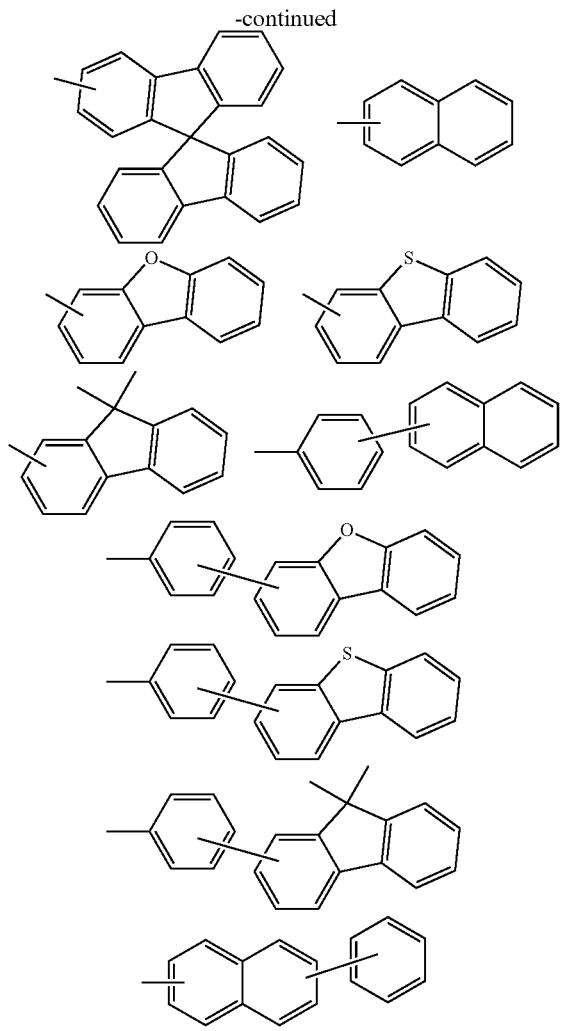

The compound represented by the Chemical Formula 1 has excellent hole transport characteristics and material stability, thereby to lower a device drive voltage, and to improve efficiency, and power consumption when the compound is applied to an organic light-emitting device. Further, when the compound is applied to the organic light-emitting device, the organic light-emitting device has high thermal and electrical stability to have a long lifespan.

The compound may be applied to a hole transport layer or an auxiliary hole transport layer of an organic light-emitting device.

In one implementation, the compound represented by the Chemical Formula 1 is free of a carbazole group. Amine derivatives containing carbazole as a previously known hole transport material have a disadvantage that the hole mobility of carbazole is low, and thus the device efficiency is low and power consumption is high. However, the compound represented by the Chemical Formula 1 is an amine derivative excluding the carbazole and has a framework structure contributing to the hole mobility. Thus, the compound represented by the Chemical Formula 1 realizes high hole mobility, thus improving power consumption when the compound is applied to the organic light-emitting device.

In one implementation, each of R, L, Ar1 and Ar2 of the compound represented by the following Chemical Formula 1 is not carbazole or is free of carbazole.

Further, a framework structure of the compound represented by the Chemical Formula 1 is naphthyl-containing naphthobenzofuran or naphthobenzothiophene, which has improved structural stability compared to dibenzothiophene and dibenzofuran structures. This framework structure of the compound represented by the Chemical Formula 1 may improve the lifespan characteristics of the organic light-emitting device.

Therefore, the compound represented by the Chemical Formula 1 contains a non-carbazole-based amine derivative as a hole transport material, but has a high hole mobility characteristic. Thus, the compound represented by the Chemical Formula 1 can lower the device drive voltage. A fused ring structure of a core in the compound is a novel structure in a hole transport material and thus may contribute to implementation of a thermally and electrically stable device.

Specifically, the compound represented by the Chemical Formula 1 may be represented by any of the following Chemical Formulas:

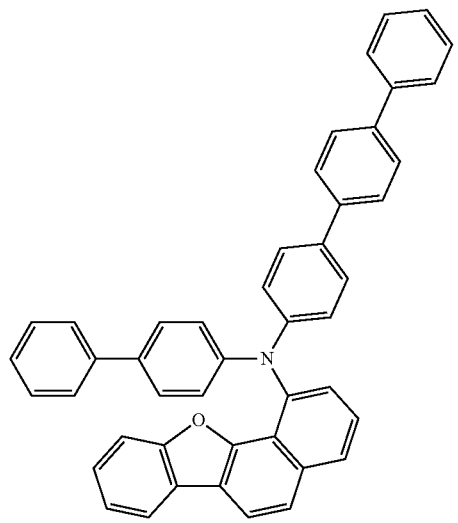

1

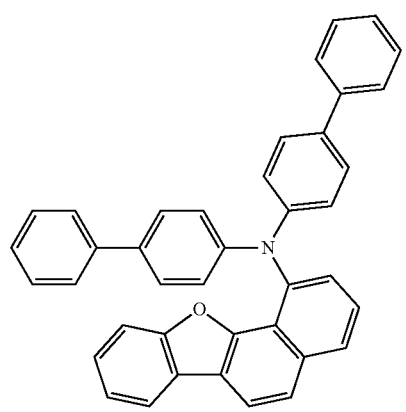

2

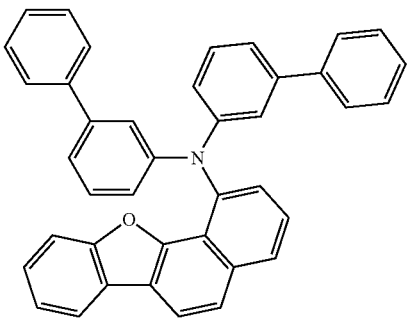

3

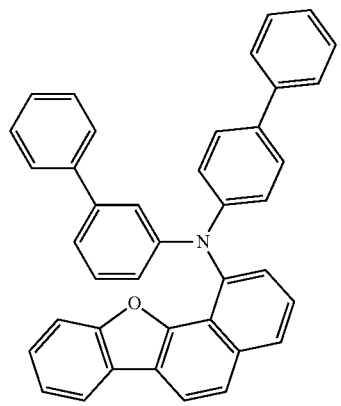

4

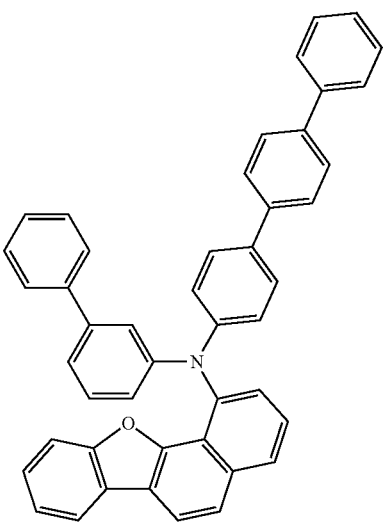

5

6
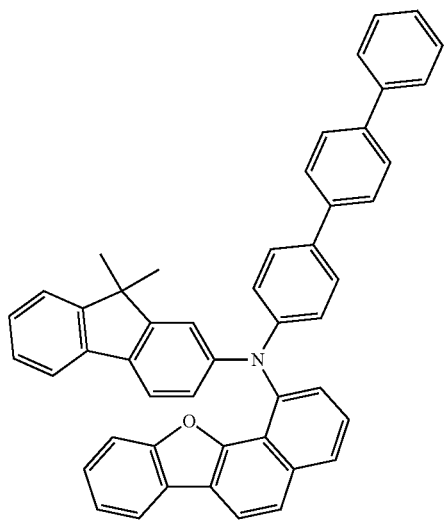
7
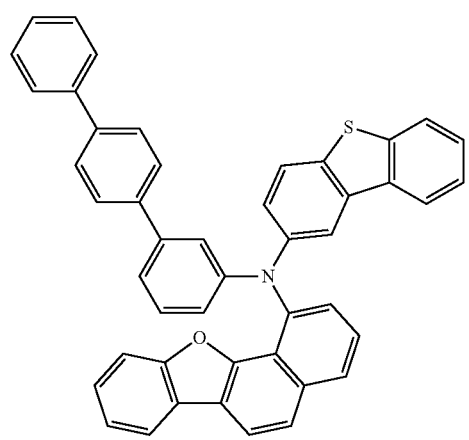
8
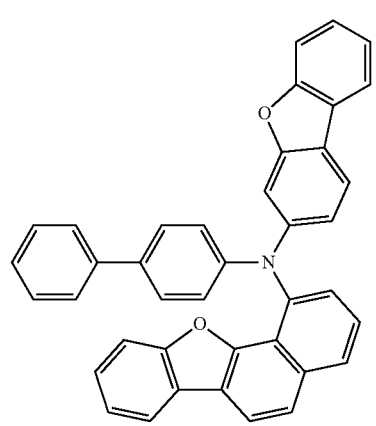
9
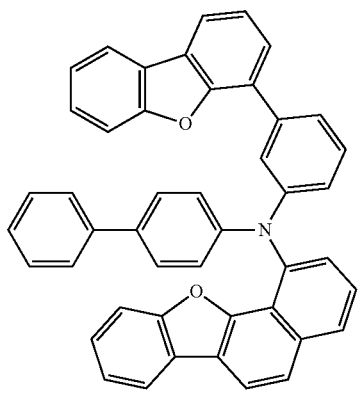
10
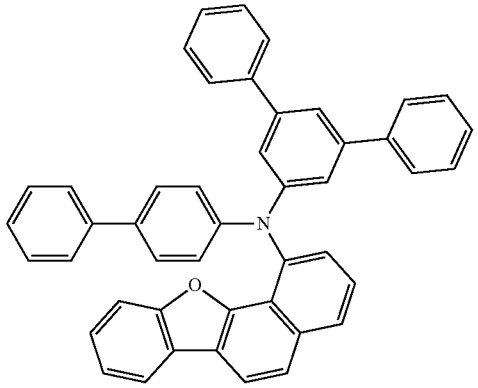
11
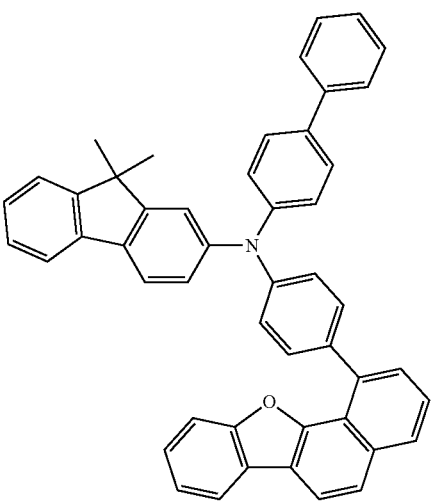

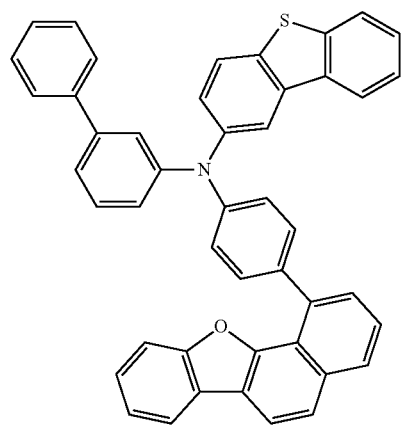
12
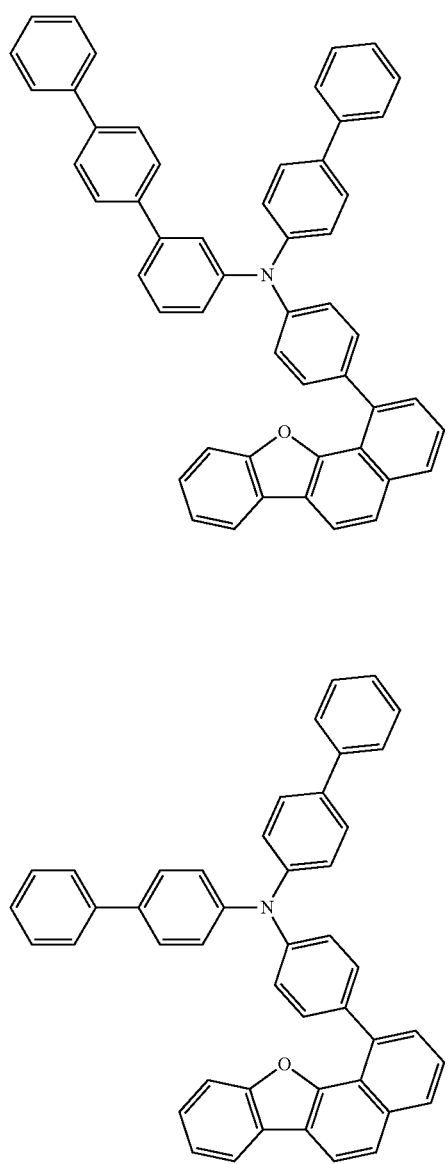
13
14
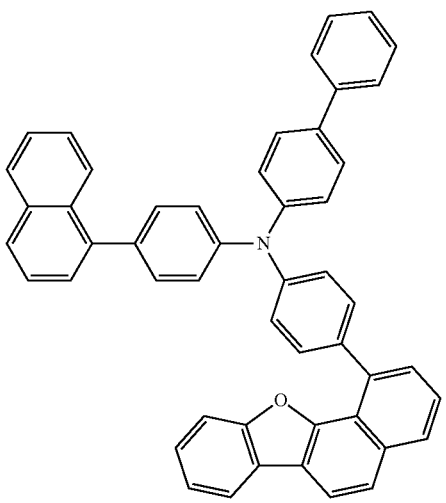
15
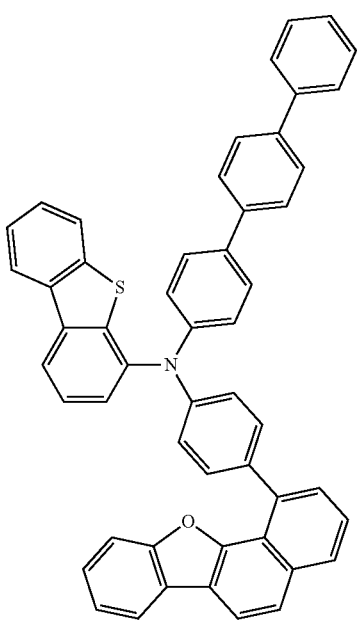
16

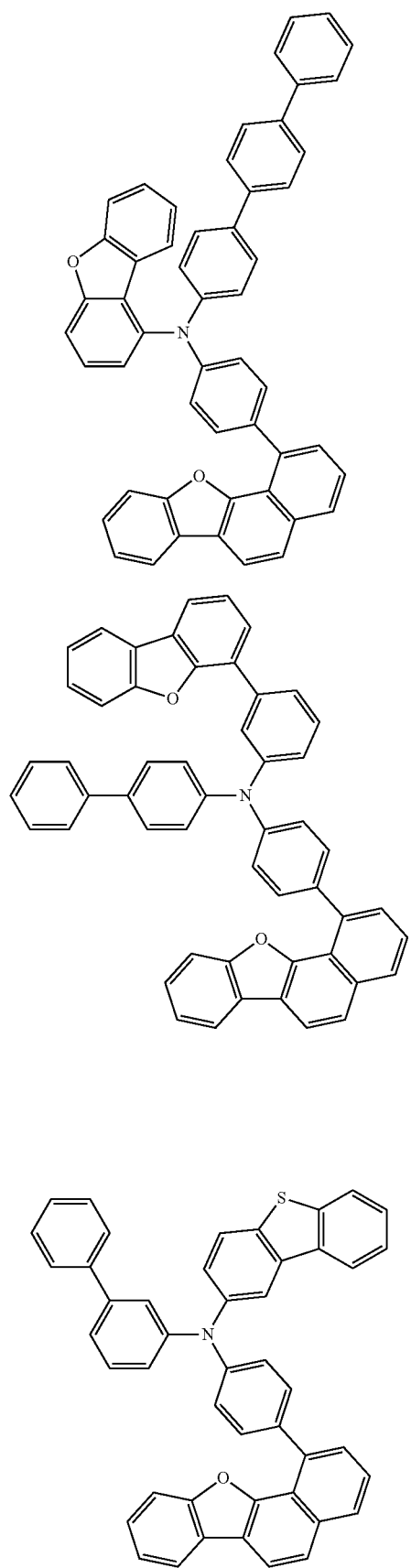
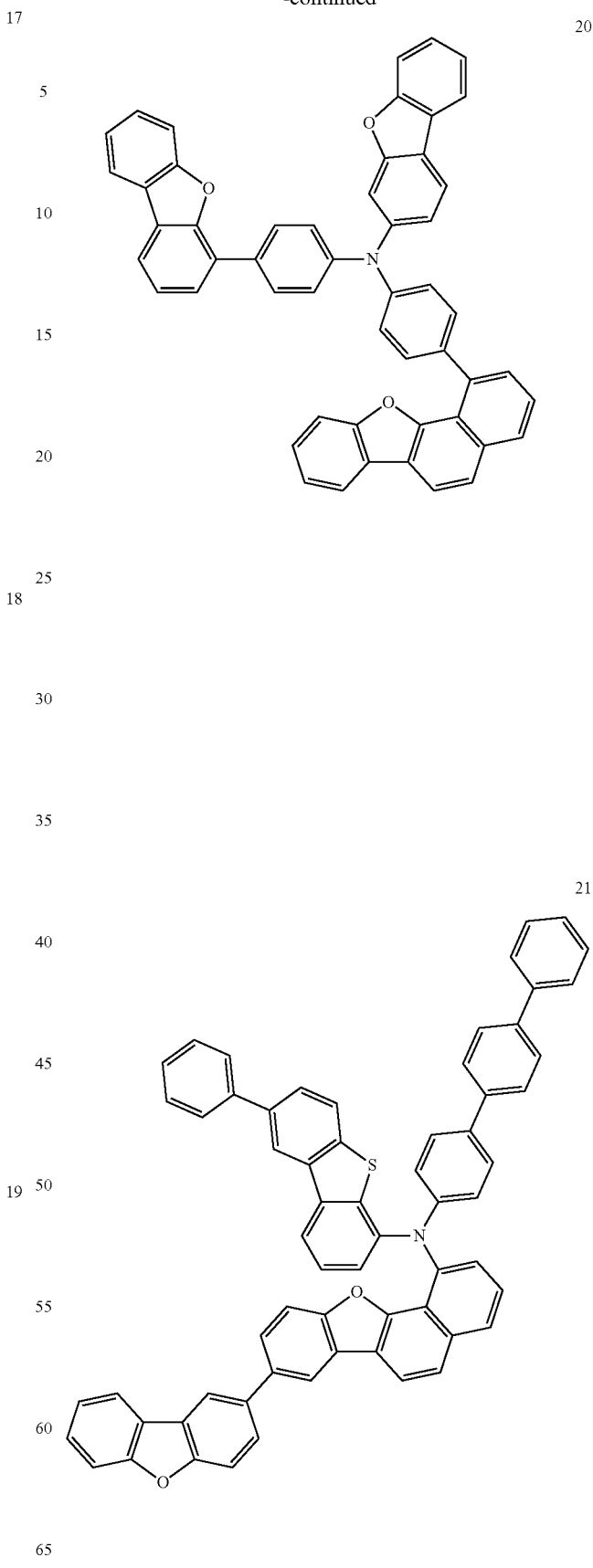

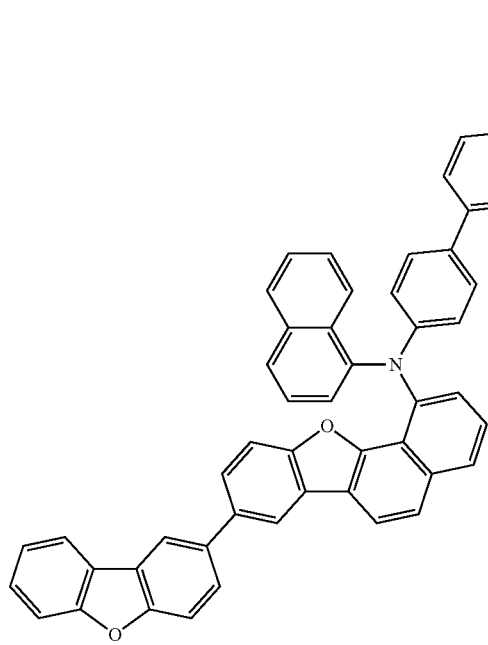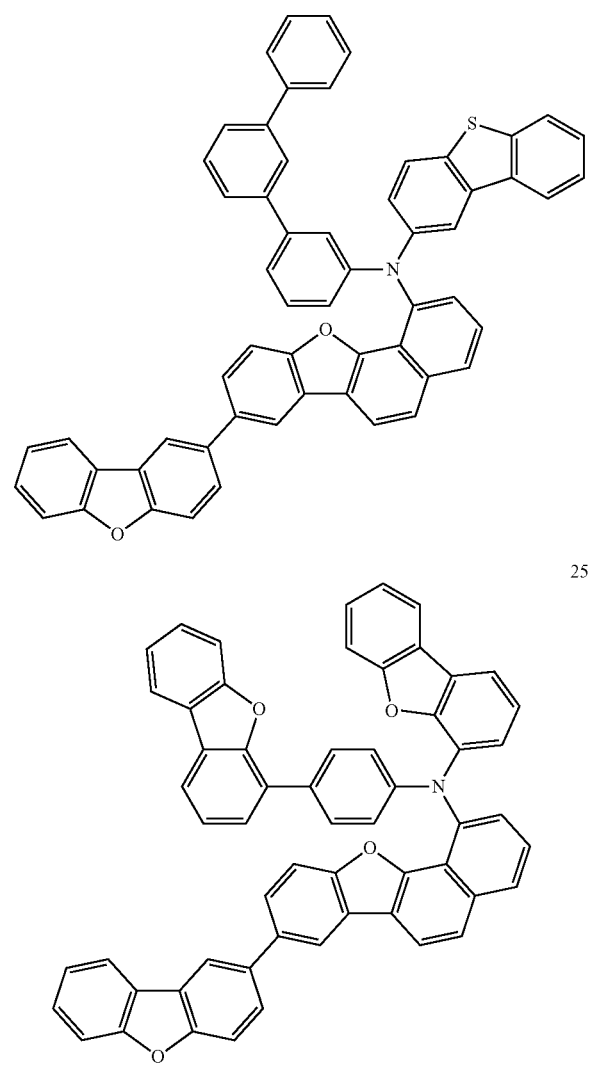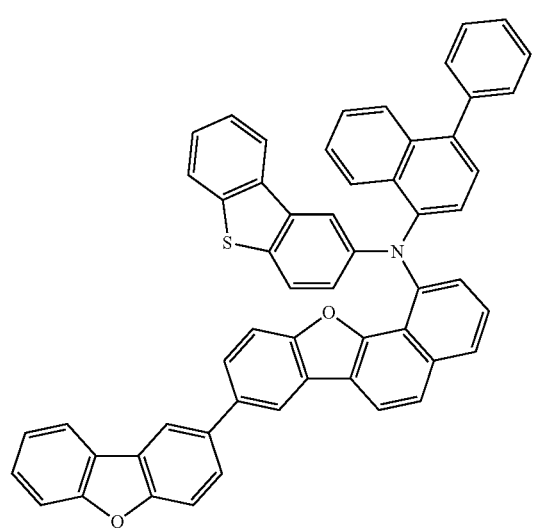

17
-continued
27
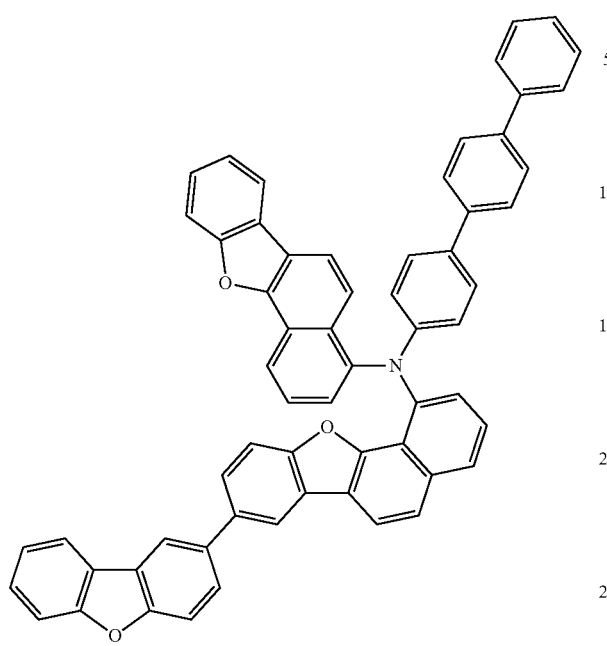
28
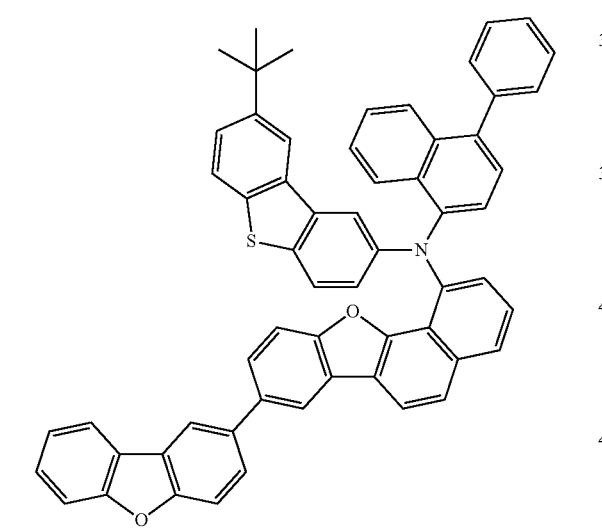
29
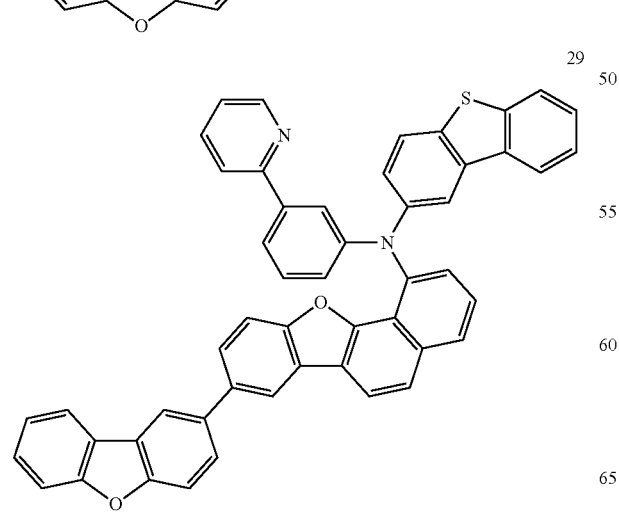
18
-continued
30
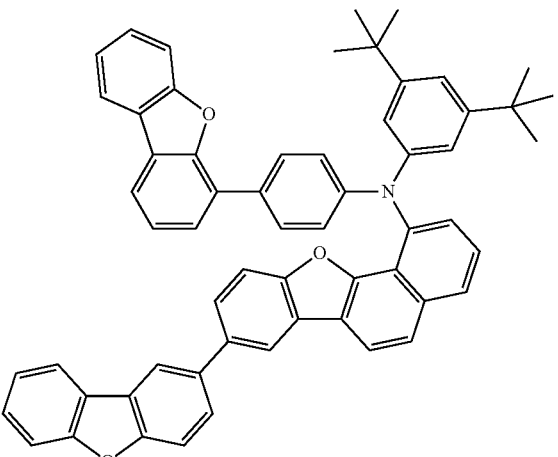
31
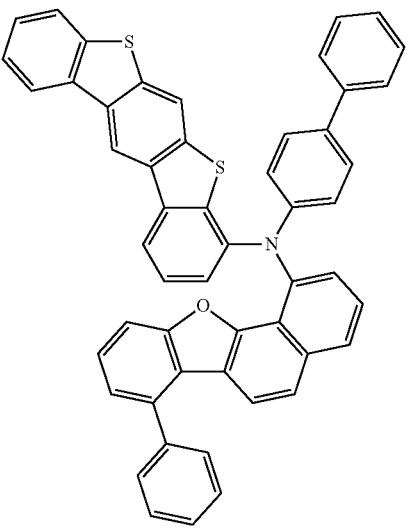
32
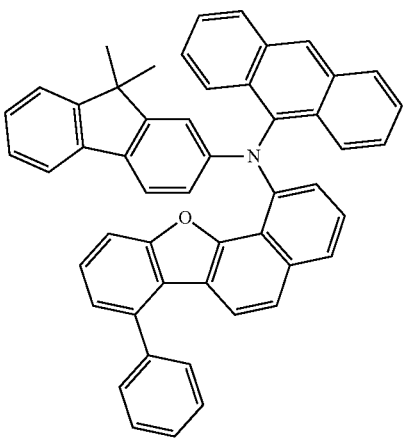

33
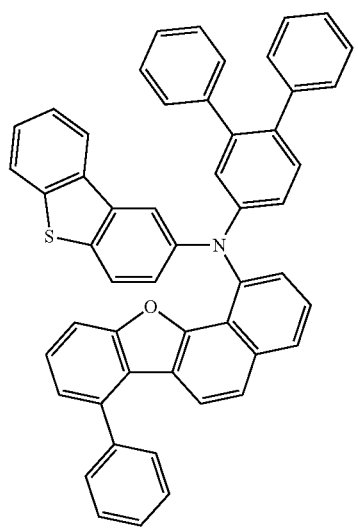
34
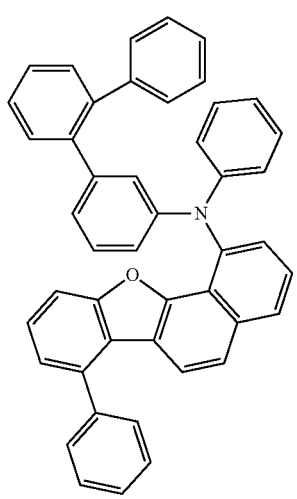
35
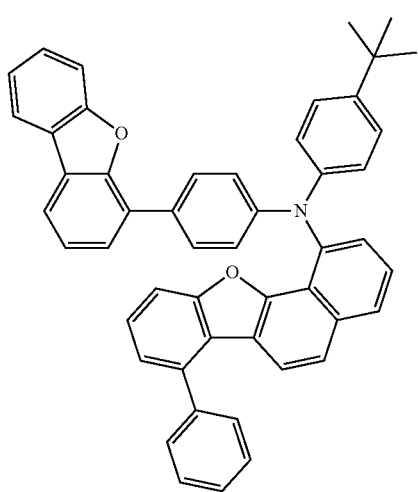
36
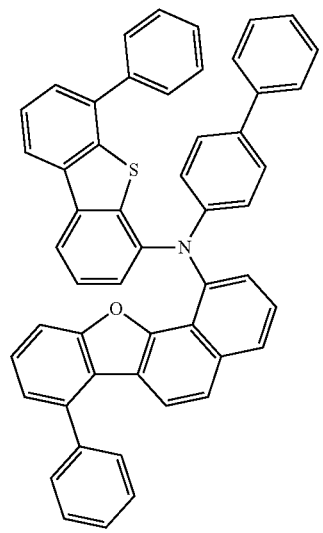
37
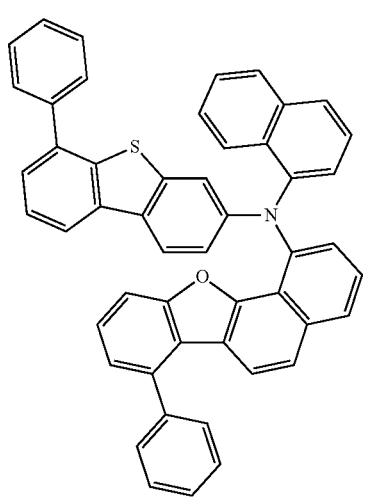
38
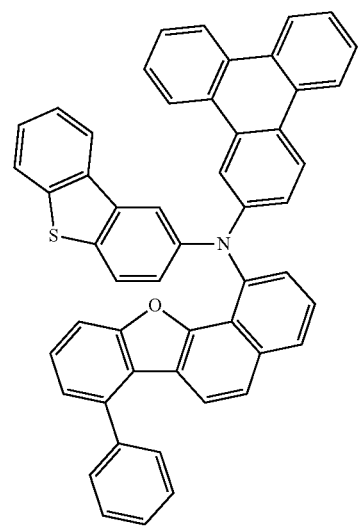

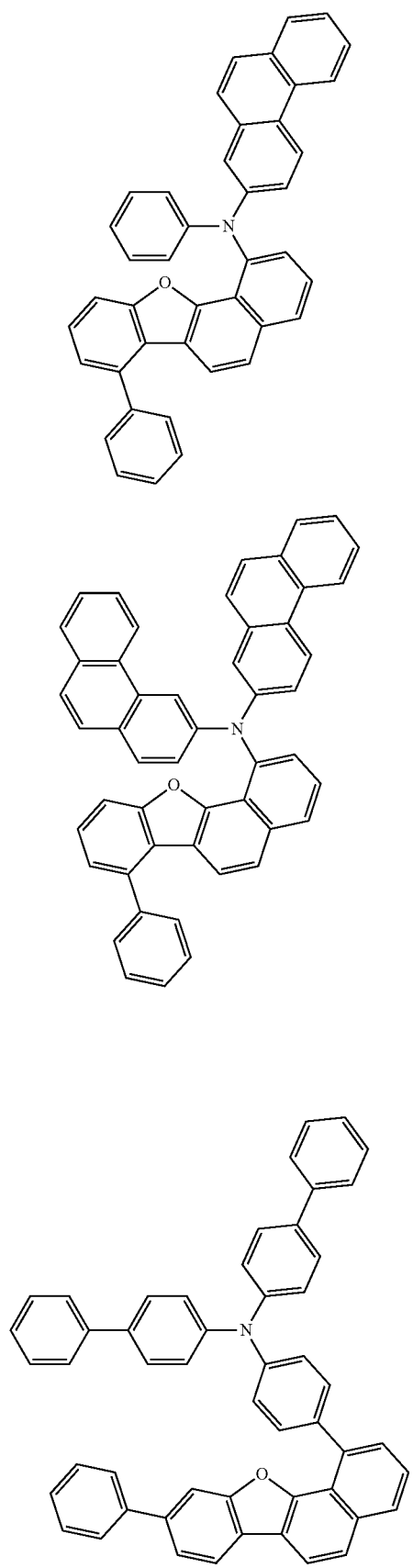

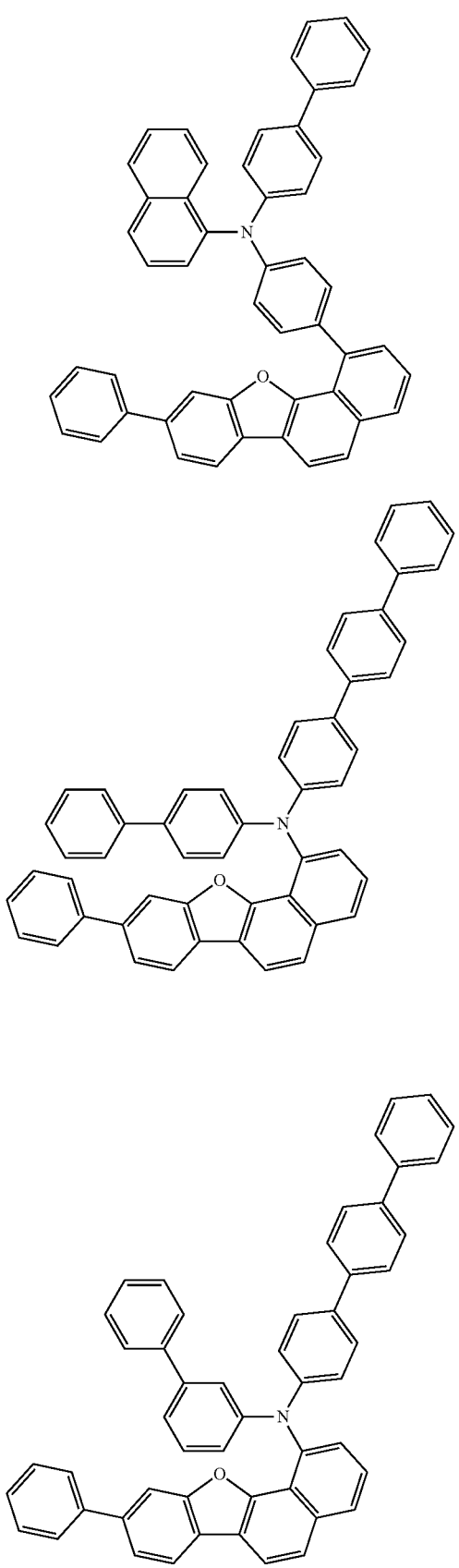
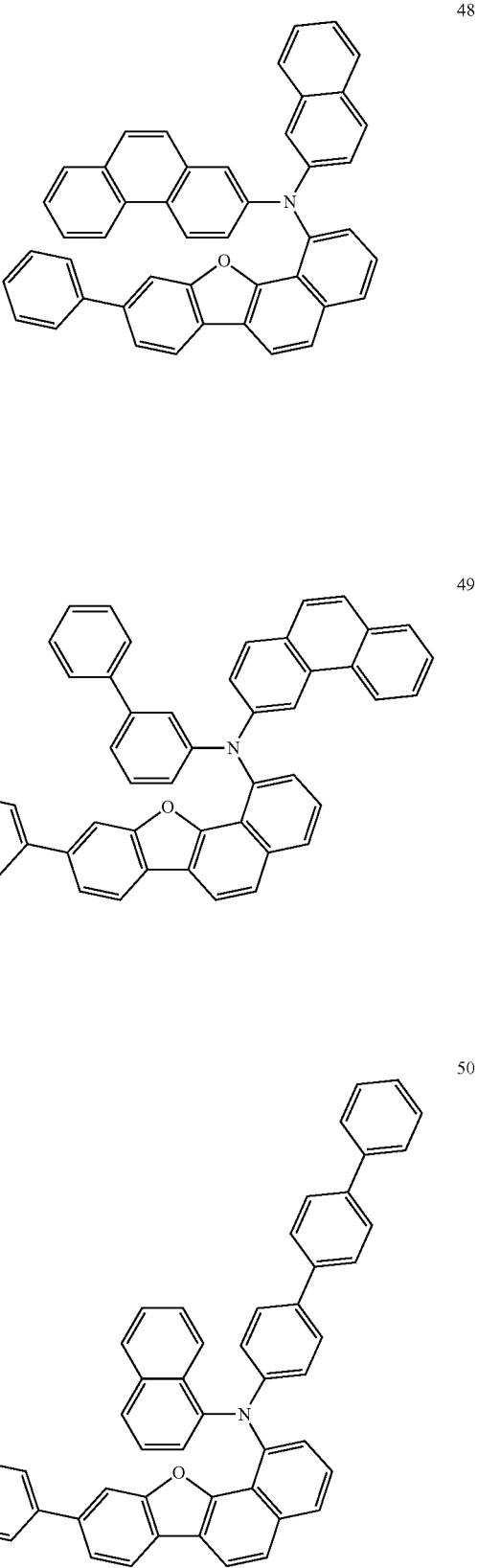

51
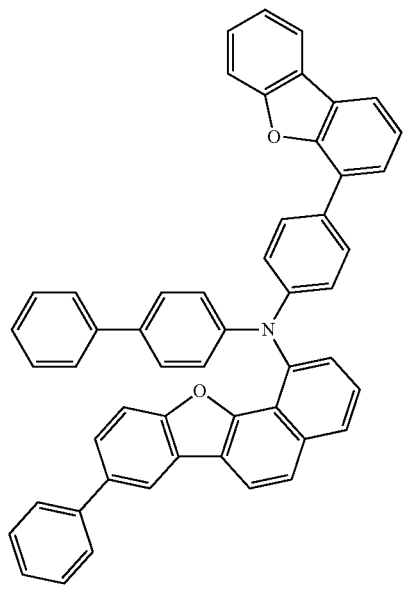
54
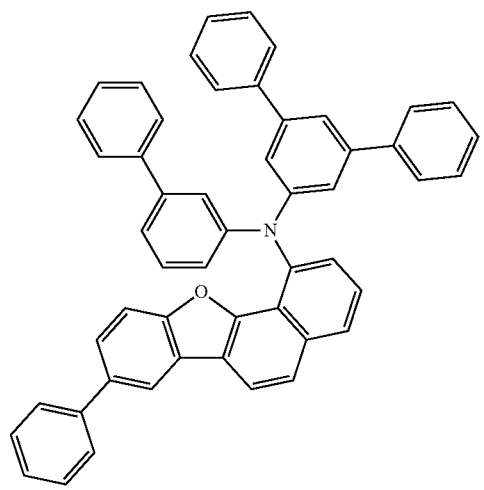
52
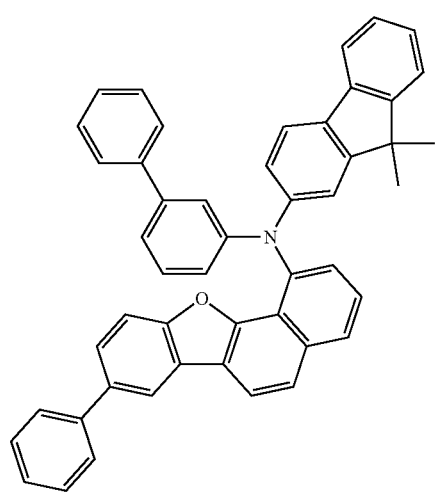
55
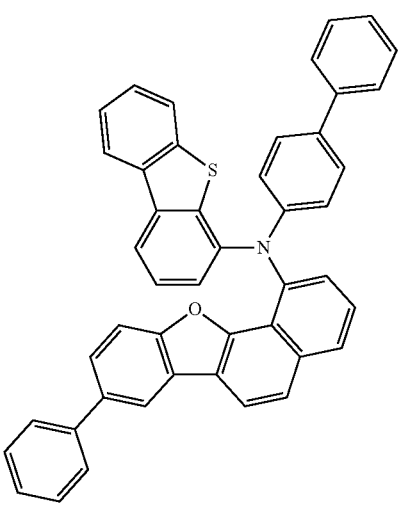
53
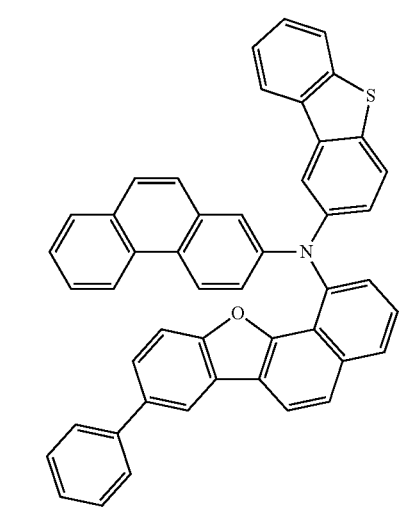
56
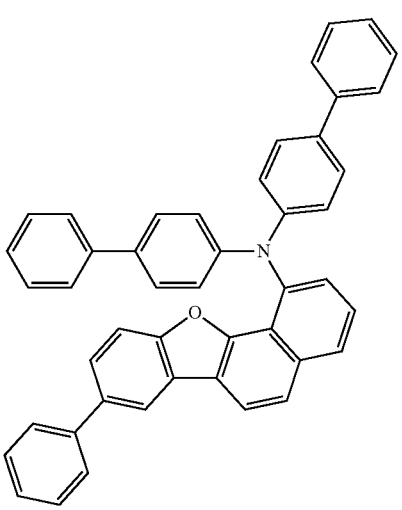

57
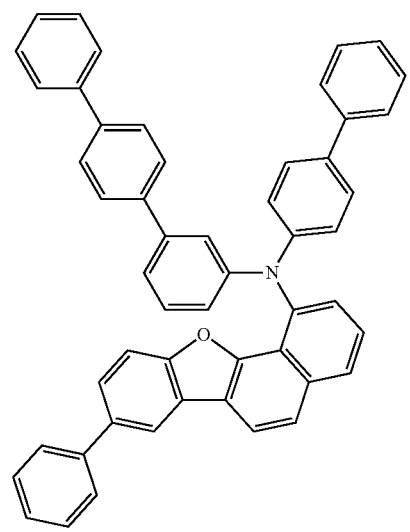
58
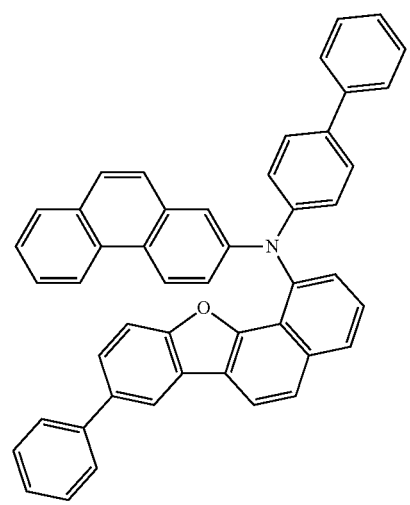
59
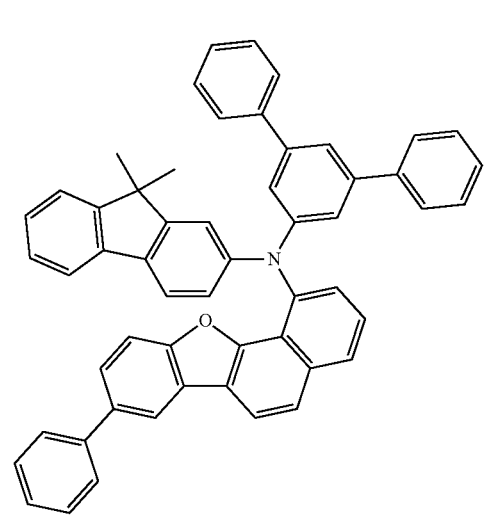
60
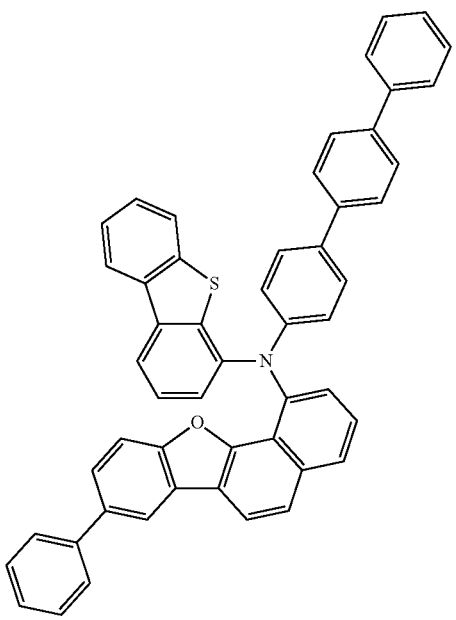
61
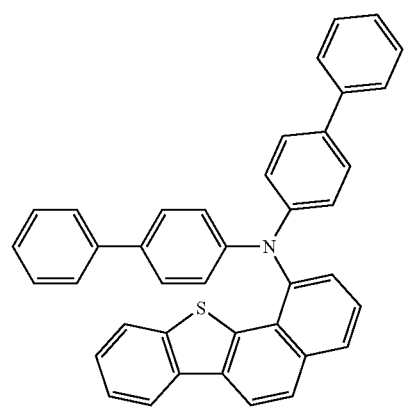
62
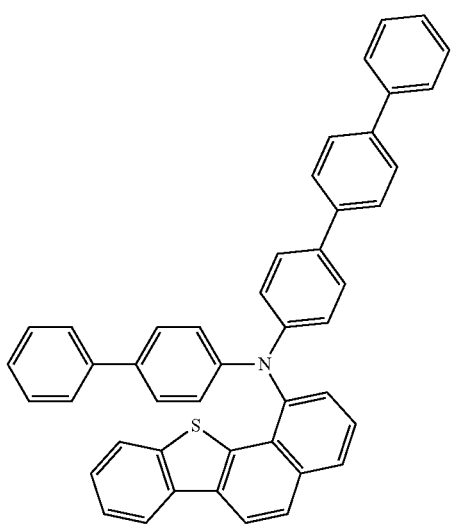

63
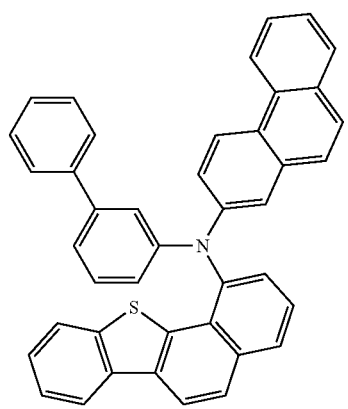
64
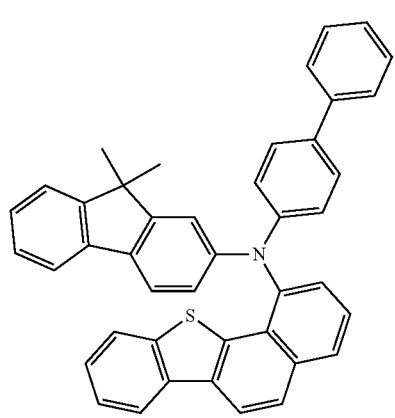
65
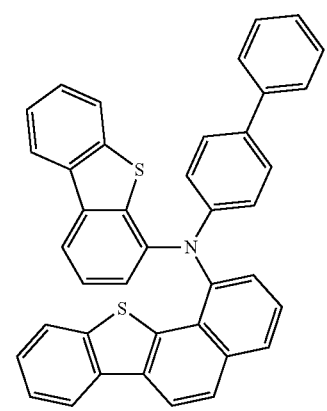
66
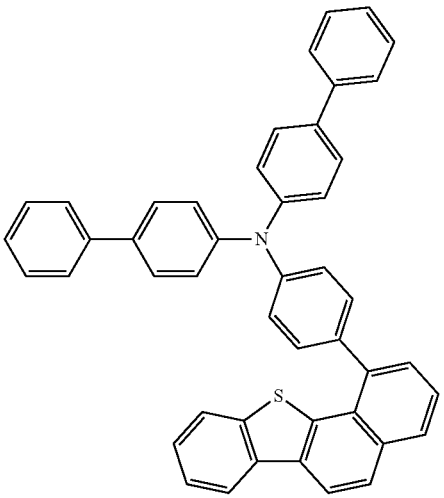
67
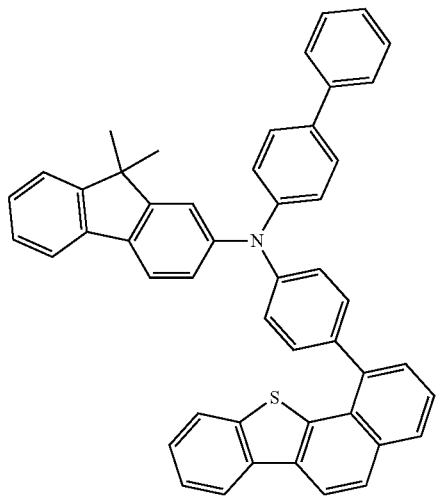
68
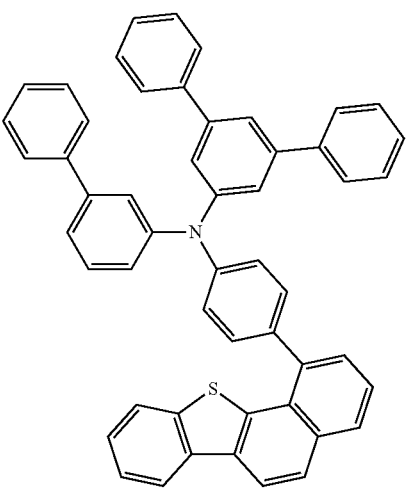

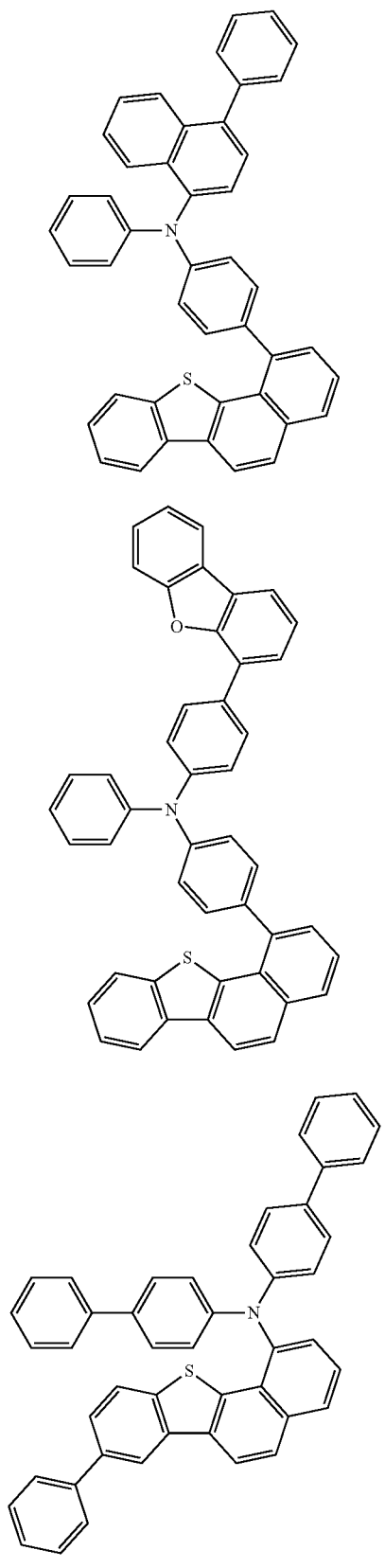
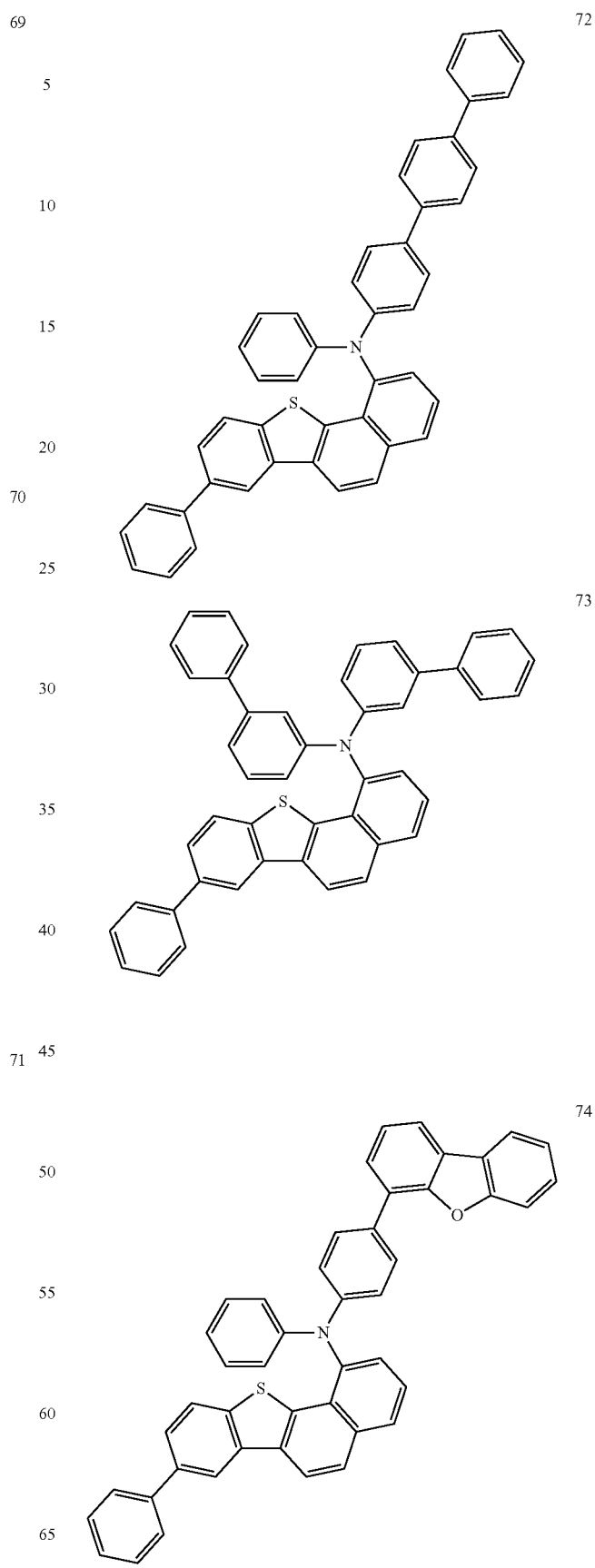

75
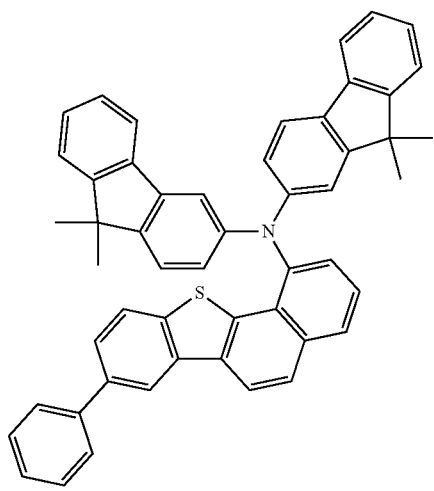
77
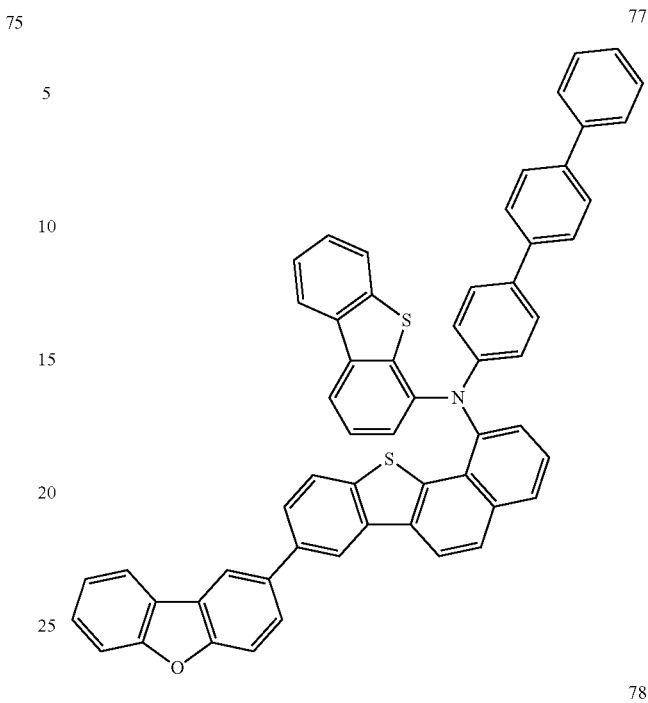
76
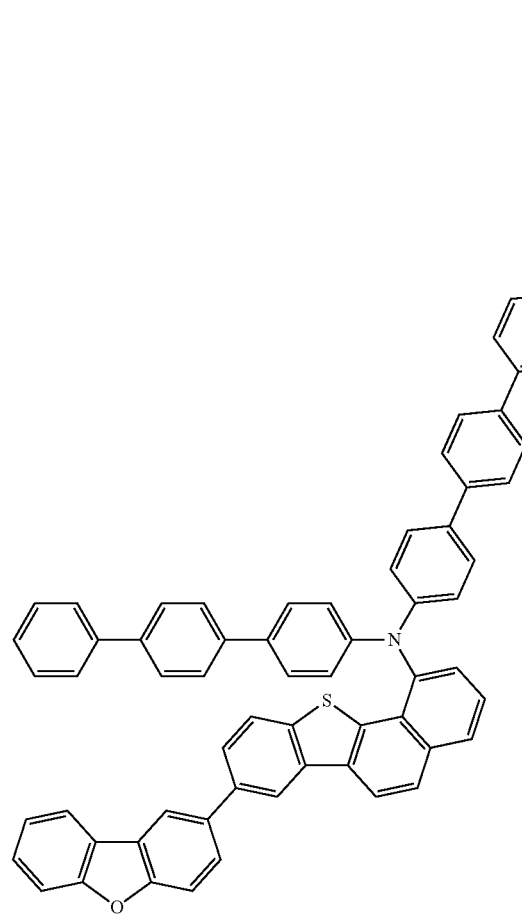
78
79
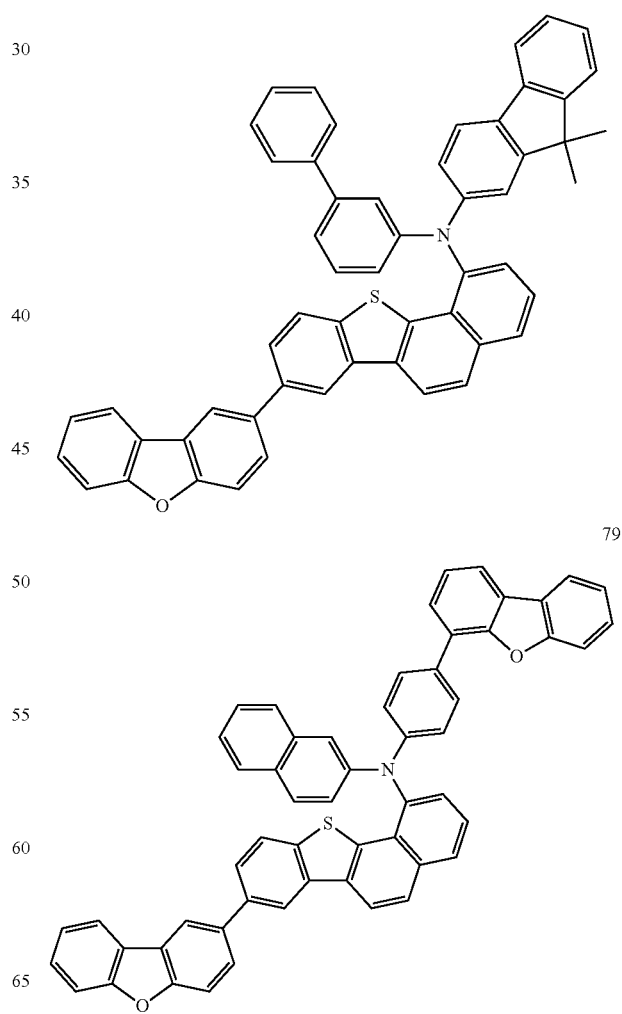

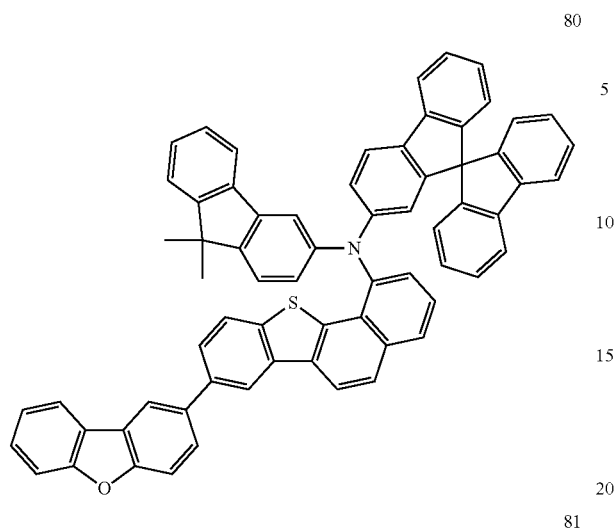
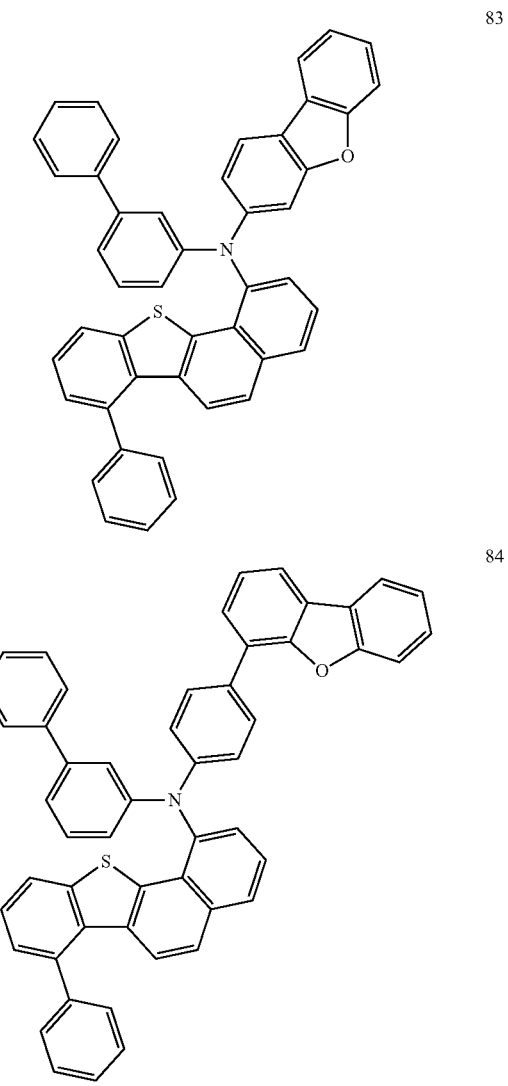
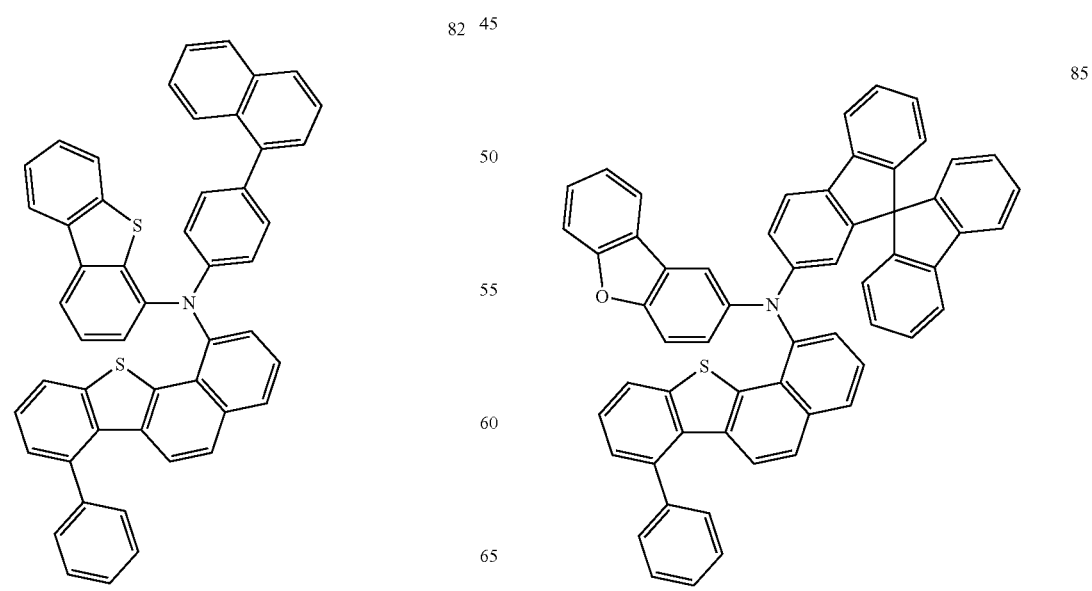

86
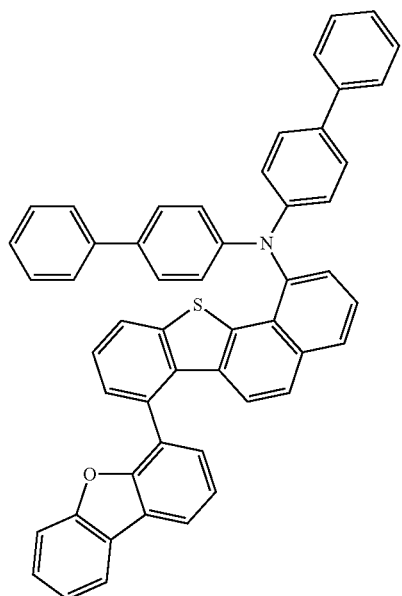
87
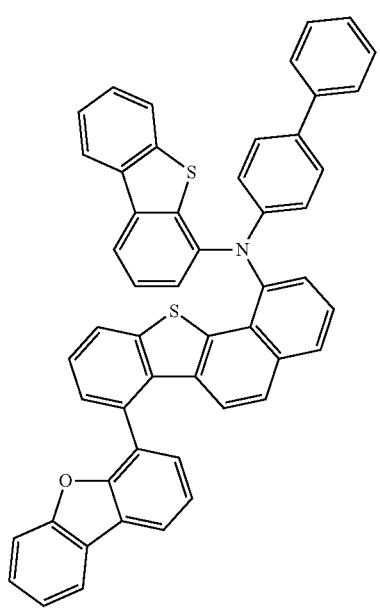
88
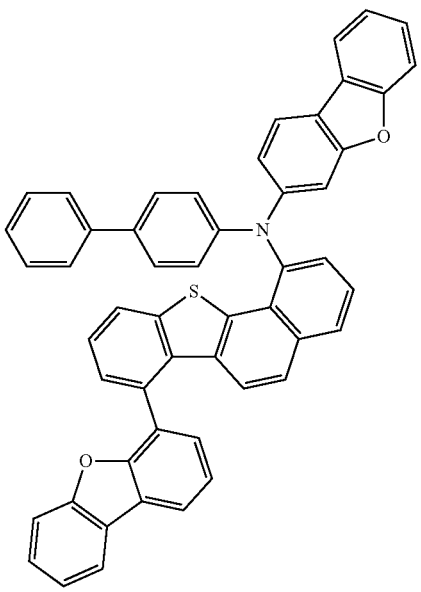
89
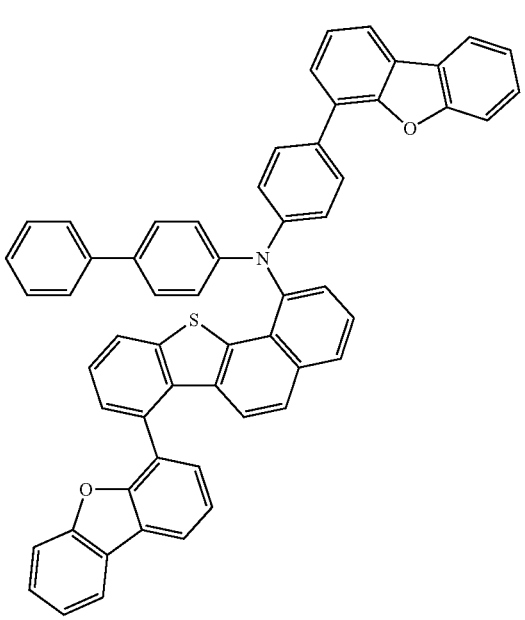

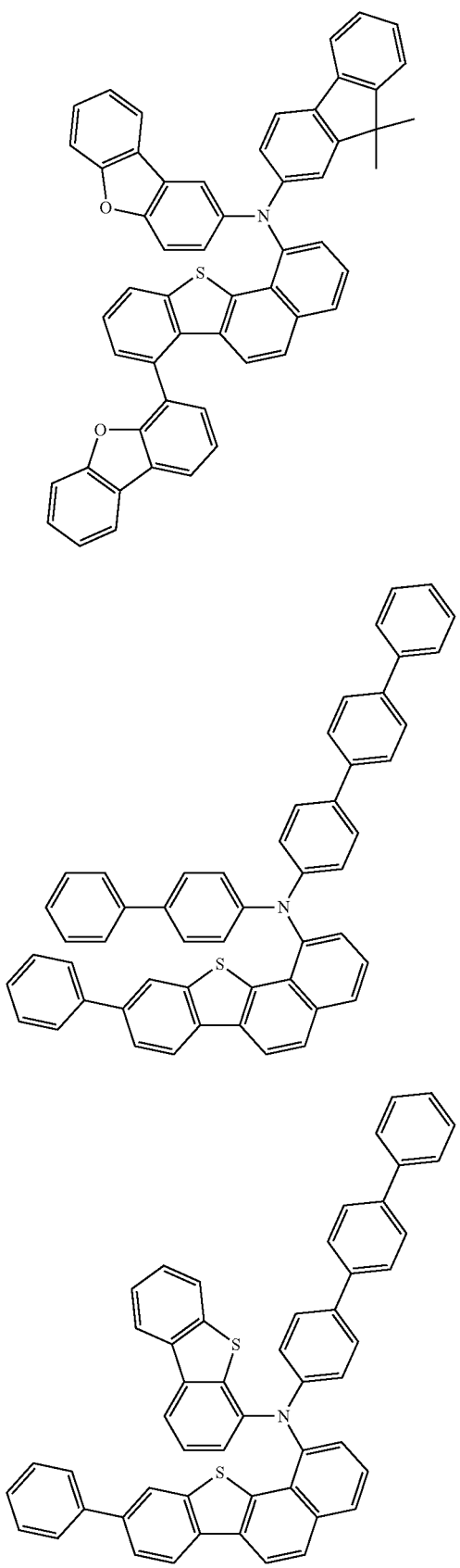
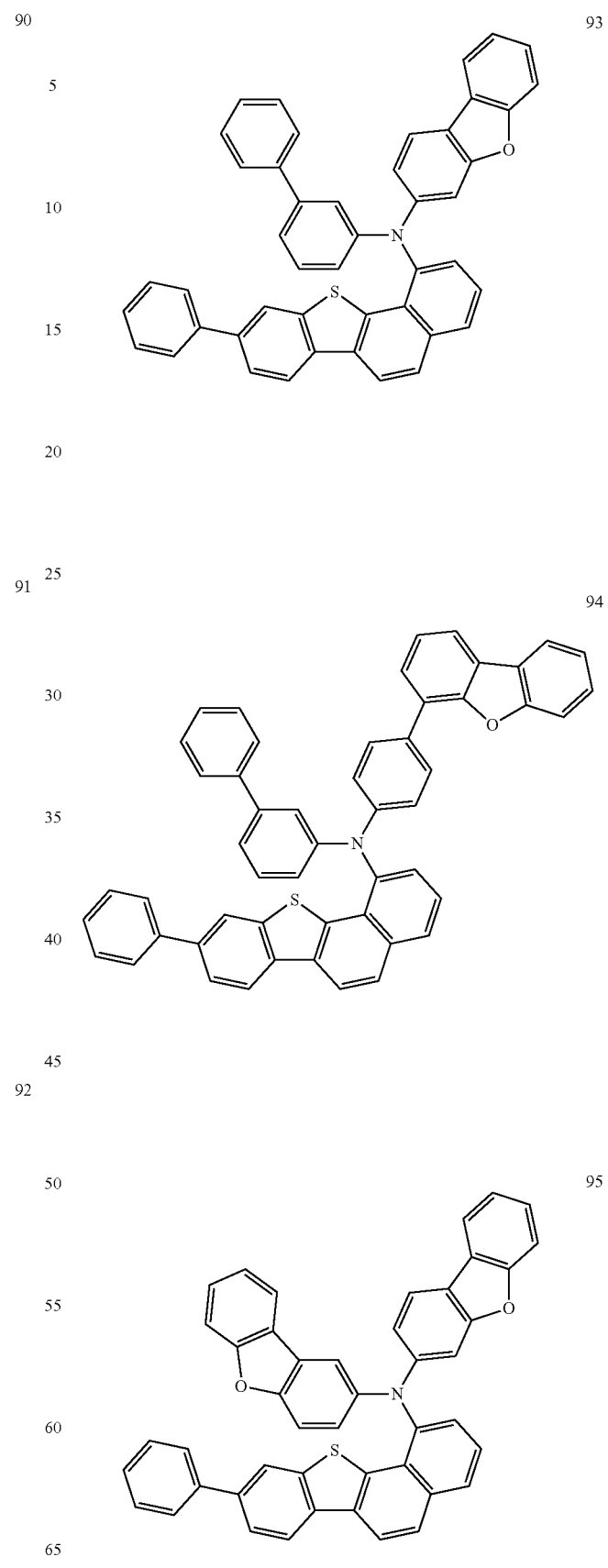

96

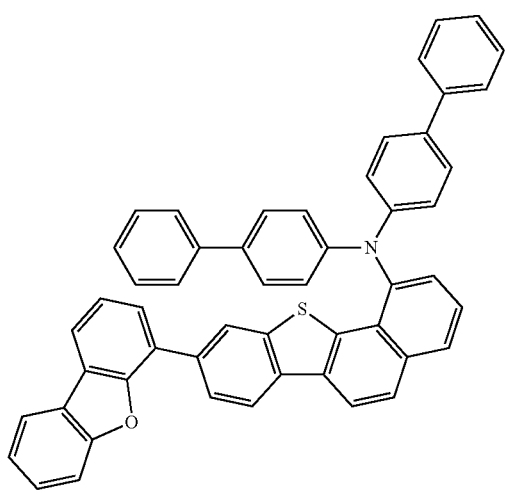

99

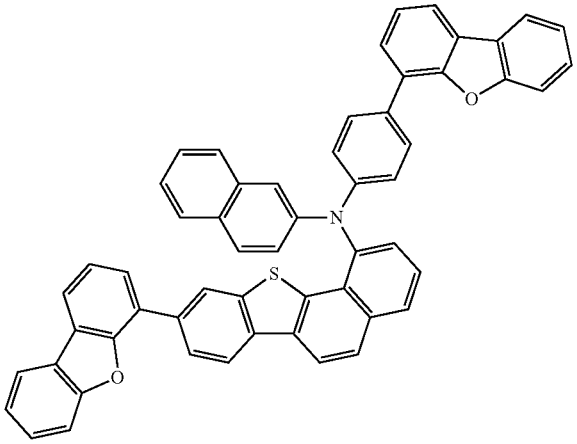

97

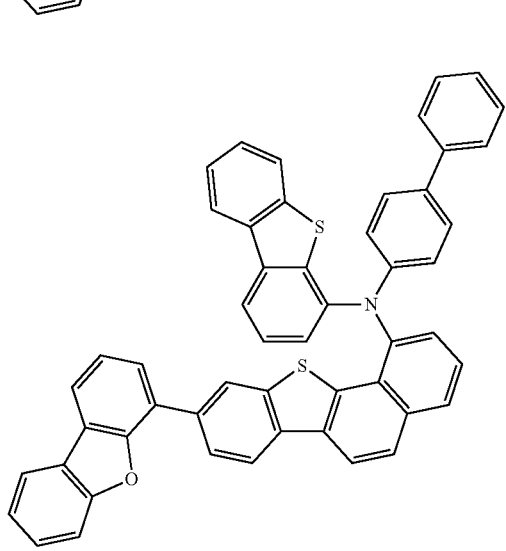

100

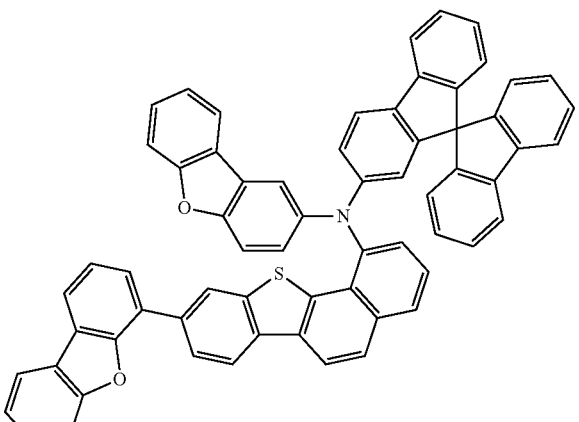

In another implementation of the present disclosure, there is provided an organic light-emitting device that includes a first electrode, a second electrode, and at least one organic material layer between the first and second electrodes, wherein the organic material layer contains the compound represented by the Chemical Formula 1:

[Chemical Formula 1]

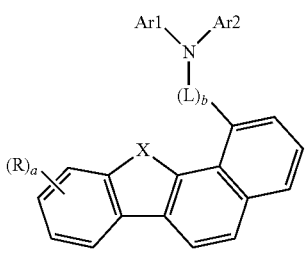

in the Chemical Formula 1,

X is O or S,

R represents one selected from the group consisting of an aryl group having 6 to 30 carbon atoms, an amino group, a heterocyclic group having 3 to 30 carbon atoms and including at least one hetero atom selected from the group consisting of O, N and S, an alkyl group having 1 to 30 carbon atoms, an alkenyl group having 2 to 30 carbon atoms, an

98

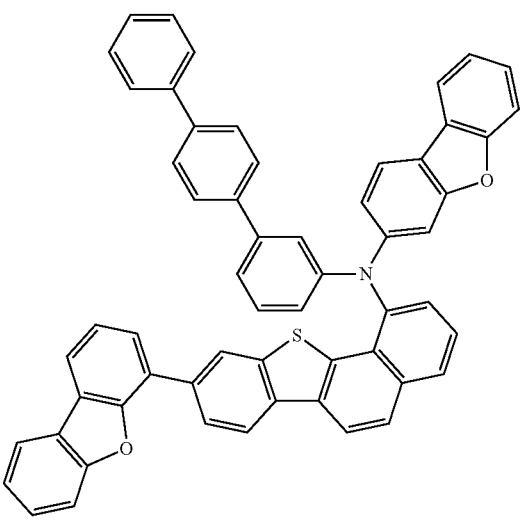

alkynyl group having 2 to 30 carbon atoms, an alkoxy group having 1 to 30 carbon atoms, and an aryloxy group having 6 to 30 carbon atoms, a is an integer from 0 to 4, provided that when a is 2 or greater, each R is the same as or different from each other, or adjacent R groups are bonded to each other to form a ring, L represents a direct bond or represents one selected from the group consisting of substituted or unsubstituted arylene having 6 to 30 carbon atoms and substituted or unsubstituted heteroarylene having 3 to 30 carbon atoms, b is an integer from 0 to 4, and each of Ar1 and Ar2 independently represents one selected from the group consisting of a substituted or unsubstituted C6 to C60 aryl group, a C3 to C30 heteroaromatic ring containing at least one heteroatom selected from the group consisting of O, N and S, an alkyl group having 1 to 30 carbon atoms, an alkenyl group having 2 to 30 carbon atoms, an alkynyl group having 2 to 30 carbon atoms, an alkoxyl group having 1 to 30 carbon atoms, and an aryloxy group having from 6 to 30 carbon atoms.

When the adjacent R groups are bonded to each other to form a ring, the ring may include an alicyclic or aromatic, single or polycyclic ring-based, saturated or unsaturated ring having 5 to 30 carbon atoms.

For example, when R is an aryl group, R may be a fluorenyl group.

A detailed description of the compound represented by the Chemical Formula 1 is as described above.

The organic light-emitting device may include an organic material layer containing the compound represented by the Chemical Formula 1 as described above.

Specifically, the organic material layer containing the compound represented by the Chemical Formula 1 may include a hole transport layer or an auxiliary hole transport layer. In one implementation, the organic material layer includes a hole transport layer or an auxiliary hole transport layer, and contains the compound represented by the Chemical Formula 1.

In one implementation, the organic material layer may include at least two or more compounds represented by the Chemical Formula 1.

The organic material layer may include, in addition to the organic material layer containing the compound represented by Chemical Formula 1, at least one organic material layer selected from the group consisting of a hole injection layer, a hole transport layer, an auxiliary hole transport layer, a light-emitting layer, an auxiliary electron transport layer, an electron transport layer and an electron injection layer.

According to the present disclosure, the hole transport layer may be embodied as a single layer or a stack of a plurality of layers.

According to the present disclosure, the auxiliary hole transport layer may be embodied as a single layer or a stack of a plurality of layers.

FIG. 1 shows an organic light-emitting device according to one implementation of the present disclosure. In FIG. 1, the organic light-emitting device 100 includes an anode 110, a hole injection layer 131, a hole transport layer 132, a light emitting layer 133, an electron transport layer 134, and a cathode 120 in this order. The hole injection layer 131, the hole transport layer 132, the light-emitting layer 133, and the electron transport layer 134 constitute a stack 130.

Figure 2:
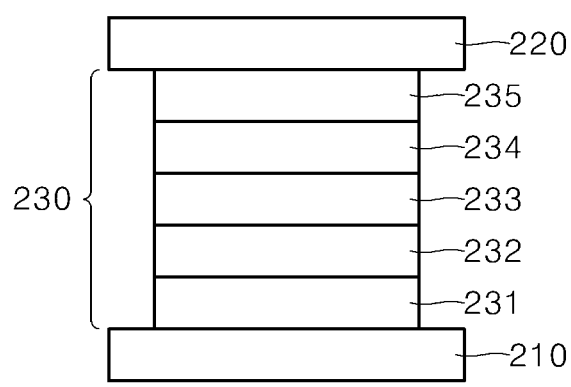
FIG. 2 is a schematic cross-sectional view of an organic light-emitting device incorporating the compound represented by the Chemical Formula 1 according to one implementation of the present disclosure.

FIG. 2 shows an organic light-emitting device according to one implementation of the present disclosure. In FIG. 2, the organic light-emitting device 200 includes an anode 210, a hole injection layer 231, a hole transport layer 232, an auxiliary hole transport layer 233, a light-emitting layer 234, an electron transport layer 235, and a cathode 220 in this order. The hole injection layer 231, the hole transport layer 232, the auxiliary hole transport layer 233, the light-emitting layer 234, and the electron transport layer 235 constitute a stack 230.

The anode 110 or 210 feeds a hole into the light-emitting layer 133 or 234. The anode may contain a conductive material with a high work function to facilitate the feeding of the hole. When the organic light-emitting device is applied to a bottom emission organic light-emitting display device, the anode may be a transparent electrode made of a transparent conductive material. When the organic light-emitting device is applied to a top emission organic light-emitting display device, the anode may be a multilayer structure with a transparent electrode layer and a reflective layer made of a transparent conductive material.

The cathode 120 or 220 feeds electrons to the light-emitting layer 133 or 234. The cathode may contain a conductive material having a low work function to facilitate feeding of electrons. When the organic light-emitting device is applied to a bottom emission organic light-emitting display device, the cathode may be a reflective electrode made of metal. When the organic light-emitting device is applied to a top emission organic light-emitting display device, the cathode may be embodied as a transparent electrode made of a metal and having a small thickness.

Each of the light-emitting layers 133 and 234 may emit red R, green G and blue B light, and may be made of a phosphorescent material or a fluorescent material.

When each of the light-emitting layers 133 and 234 emits red light, and when each of the light-emitting layers 133 and 234 is made of a phosphorescent material, each of the light-emitting layers 133 and 234 may contain: a host material including CBP (carbazole biphenyl) or mCP (1,3-bis (carbazol-9-yl); and dopants doped into the host including at least one selected from the group consisting of PIQIr(acac)(bis(1-phenylisoquinoline)acetylacetonate iridium), PQIr(acac)(bis(1-phenylquinoline)acetylacetonate iridium), PQIr(tris(1-phenylquinoline)iridium), PtOEP(octaethylporphyrin platinum), and combinations thereof. Alternatively, when each of the light-emitting layers 133 and 234 emits red light, and when each of the light-emitting layers 133 and 234 is made of a fluorescent material, each of the light-emitting layers 133 and 234 may contain PBD: Eu (DBM)3(Phen) or perylene. However, the present disclosure is not limited thereto.

When each of the light-emitting layers 133 and 234 emits green light, and when each of the light-emitting layers 133 and 234 is made of a phosphorescent material, each of the light-emitting layers 133 and 234 may contain: a host material that includes CBP or mCP; and dopants doped into the host including Ir(ppy)3(fac tris(2-phenylpyridine) iridium). Alternatively, when each of the light-emitting layers 133 and 234 emits green light, and when each of the light-emitting layers 133 and 234 is made of a fluorescent material, each of the light-emitting layers 133 and 234 may contain Alq3(tris(8-hydroxyquinolino)aluminum). However, the present disclosure is not limited thereto.

When each of the light-emitting layers 133 and 234 emits blue light, and when each of the light-emitting layers 133 and 234 is made of a phosphorescent material, each of the light-emitting layers 133 and 234 may contain: a host material that includes CBP or mCP; and dopants doped into the host including (4,6-F2ppy)2Irpic. Alternatively, when each of the light-emitting layers 133 and 234 emits blue light, and when each of the light-emitting layers 133 and 234 is made of a fluorescent material, each of the light-emitting layers 133 and 234 may contain at least one selected from the group consisting of spiro-DPVBi, spiro-6P, distyrylbenzene (DSB), distyrylarylene (DSA), PFO-based polymer and PPV-based polymer and combinations thereof, or may contain the compound of the Chemical Formula 1 as the blue fluorescent material. However, the present disclosure is not limited thereto.

Each of the hole injection layers 131 and 231 may facilitate the injection of holes.

Each of the hole injection layers 131 and 231 may be made of at least one selected from the group consisting of, for example, CuPc (cupper phthalocyanine), PEDOT (poly (3,4)-ethylenedioxythiophene), PANI (polyaniline), NPD (N,N-dinaphthyl-N,N'-diphenyl benzidine) and combinations thereof. However, the present disclosure is not limited thereto.

Each of the hole transport layers 132 and 232 may contain, as a hole transport material, a material electrochemically stabilized via cationization (i.e., by losing electrons). Alternatively, Each of the hole transport layers 132 and 232 may contain a material that produces a stable radical cation as a hole transport material. Each of the hole transport layers 132 and 232 may contain a known hole transport material or the compound represented by the Chemical Formula 1. The detailed description of the compound represented by the Chemical Formula 1 is as described above.

Each of the hole transport layers 132 and 232 may further contain an additional hole transport material other than the compound represented by the Chemical Formula 1.

The known hole transport material or the additional hole transport material may contain aromatic amine to be easily cationized. In one example, the additional hole transport material may include at least one selected from the group consisting of NPD(N,N-dinaphthyl-N,N'-diphenylbenzidine), TPD (N,N'-bis-(3-methylphenyl)-N,N'-bis-(phenyl)-benzidine), spiro-TAD (2,2',7,7'-tetrakis(N,N-dimethyl-amino)-9,9-spirofluorene), MTDATA (4,4',4-Tris(N-3-methylphenyl-N-phenylamino)-triphenylamine) and combinations thereof. However, the present disclosure is not limited thereto.

The auxiliary hole transport layer 233 may contain the compound represented by the Chemical Formula 1, or may contain a known auxiliary hole transport material. The detailed description of the compound represented by the Chemical Formula 1 is as described above.

The auxiliary hole transport layer 233 may further contain an additional auxiliary hole transport material other than the compound represented by the Chemical Formula 1.

Each of the known auxiliary hole transport material and the additional auxiliary hole transport material may include at least one selected from the group consisting of, for example, TCTA, tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, tri-p-tolylamine, 1,1-bis (4-(N,N'-di(ptolyl)amino)phenyl)cyclohexane (TAPC), MTDATA, mCP, mCBP, CuPc, N,N'-bis[4-[bis(3-methylphenyl)amino]phenyl]-N,N'-diphenyl-[1,1'-biphenyl]-4, 4'-diamine (DNTPD), TDAPB, and combinations thereof. However, the present disclosure is not limited thereto.

The auxiliary electron transport layer (not shown) may be positioned between each of the electron transport layers 134 and 235 and each of the light-emitting layers 133 and 234. The auxiliary electron transport layer may further contain an auxiliary electron transport material.

The auxiliary electron transport material may include at least one selected from the group consisting of, for example, oxadiazole, triazole, phenanthroline, benzoxazole, benzothiazole, benzimidazole, triazine, and combinations thereof. However, the present disclosure is not limited thereto.

Each of the electron transport layers 134 and 235 receive electrons from the cathode. Each of the electron transport layers 134 and 235 may transfer the supplied electrons to the light-emitting layer.

Each of the electron transport layers 134 and 235 may serve to facilitate the transport of electrons. Each of the electron transport layers 134 and 235 contains an electron transport material.

The electron transport material may be electrochemically stabilized by anionization (i.e., by obtaining electrons). Alternatively, the electron transport material may produce the stable radical anion. Alternatively, the electron transport material may contain a heterocyclic ring to be easily anionized by heteroatoms.

In one example, the electron transport material may include at least one selected from the group consisting of, for example, PBD (2-(4-biphenylyl)-5-(4-tert-butylphenyl)-1,3, 4oxadiazole), TAZ (3-(4-biphenyl)4-phenyl-5-tert-butylphenyl-1,2,4-triazole), spiro-PBD, TPBi (2,2',2-(1,3,5-benzinetriyl)-tris(1-phenyl-1-H-benzimidazole), oxadiazole, triazole, phenanthroline, benzoxazole, benzthiazole, and combinations thereof. However, the present disclosure is not limited thereto.

In one example, the electron transport material may include an organic metal compound such as an organic aluminum compound, or an organic lithium compound including at least one selected from the group consisting of, for example, Alq3(tris(8-hydroxyquinolino)aluminum), Liq (8-hydroxyquinolinolatolithium), BAlq (bis(2-methyl-8-quinolinolate)-4-(phenylphenolato)aluminium), and SAlq, etc. However, the present disclosure is not limited thereto.

Specifically, the organometallic compound may be an organic lithium compound.

More specifically, a ligand bound to the lithium of the organolithium compound may be a hydroxyquinoline based ligand.

The organic material layer may further include an electron injection layer (not shown).

The electron injection layer serves to facilitate the injection of electrons and contains an electron injection material. The electron injection material may include, but is not limited to, at least one selected from the group consisting of Alq3(tris(8-hydroxyquinolino)aluminum), PBD, TAZ, Spiro-PBD, BAlq, SAlq and combinations thereof. Alternatively, the electron injection layer may be made of a metal compound. The metal compound may include, but is not limited to, at least one selected from the group consisting of, for example, LiQ, LiF, NaF, KF, RbF, CsF, FrF, $BeF_2$, $MgF_2$, $CaF_2$, $SrF_2$, $BaF_2$ and $RaF_2$.

The organic material layer may further include at least one selected from the group consisting of the hole injection layer, the hole transport layer, the auxiliary hole transport layer, the light-emitting layer, the auxiliary electron transport layer, the electron transport layer and the electron injection layer. Each of the hole injection layer, hole transport layer, auxiliary hole transport layer, light-emitting layer, auxiliary electron transport layer, electron transport layer and electron injection layer may be embodied as a single layer or a stack of multiple layers.

The organic light-emitting device according to the present disclosure may be applied to organic light emitting display devices such as a mobile phone and TV. For example, FIG. 3 is a schematic cross-sectional view of an organic light emitting display device applicable to a mobile phone according to an exemplary embodiment of the present disclosure.

Figure 3:
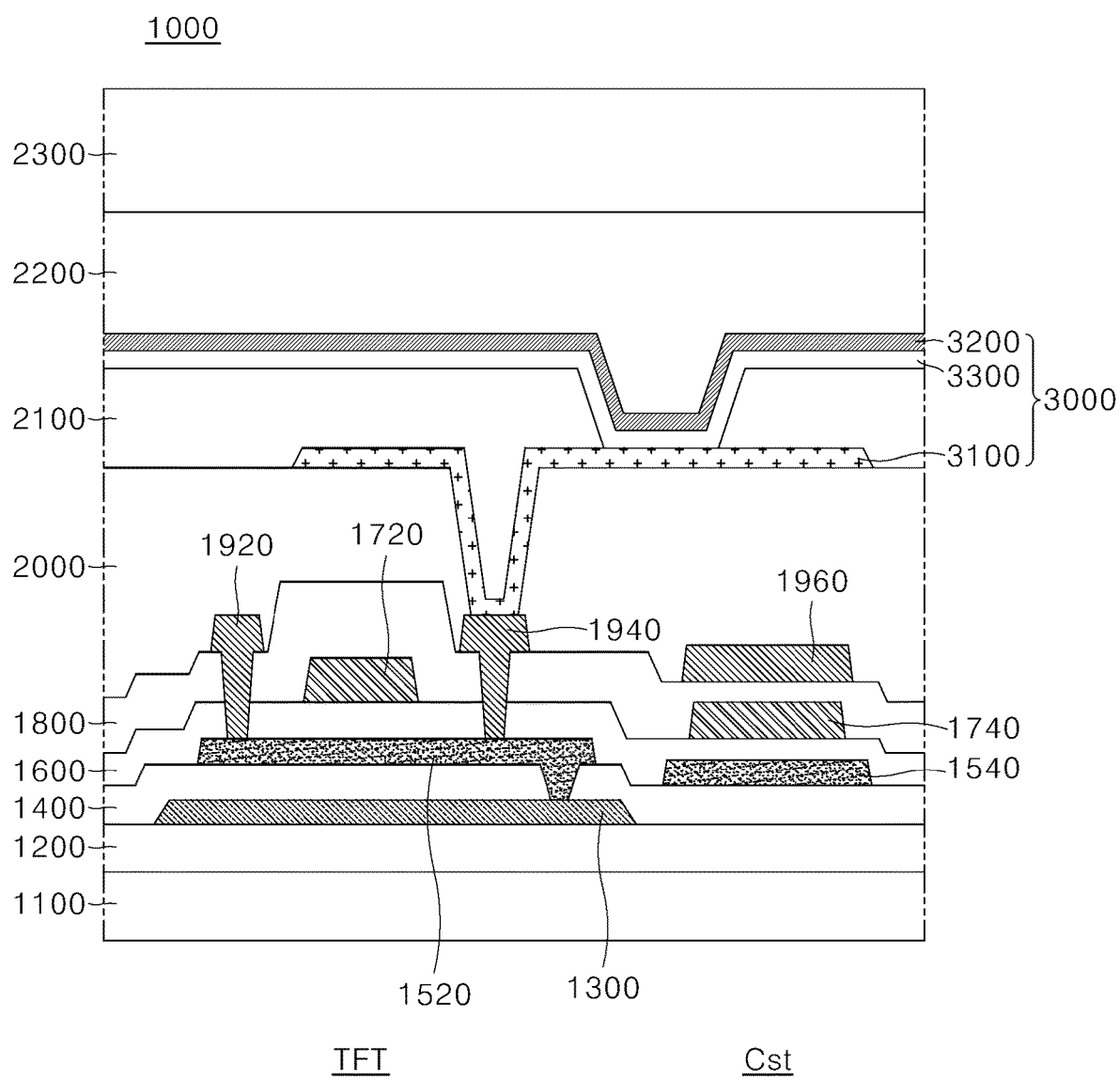
FIG. 3 is a schematic cross-sectional view of an organic light-emitting display device employing the organic light-emitting device according to another implementation of the present disclosure.

As shown in FIG. 3, the organic light-emitting display device 1000 may include a substrate 1100, an organic light-emitting device 3000, and an encapsulating layer 2200 covering the organic light-emitting device 3000.

On the substrate 1100, a drive thin-film transistor TFT, which is a drive device, and the organic light-emitting device 3000, which is connected to the drive thin-film transistor TFT, are positioned.

Although not shown, on the substrate 1100, a gate line and a data line, which define a pixel region, a power line extending parallel to and spaced from either the gate line or the data line, and a switching thin-film transistor connected to the gate line and data line are formed.

The driving thin-film transistor TFT is connected to the switching thin-film transistor, and includes an active layer 1520, a gate electrode 1720, a source electrode 1920 and a drain electrode 1940. A gate insulating film 1600 and an inter-layer insulating film 1800 are interposed therebetween. As shown in FIG. 3, the source electrode 1920 and the drain electrode 1940 are electrically connected to the active layer 1520 via a contact hole formed in the gate insulating film 1600 and the inter-layer insulating film 1800. The drain electrode 1940 is connected to a first electrode 3100 of the organic light-emitting device 3000.

A storage capacitor Cst is connected to a power line and one electrode of the switching thin-film transistor and includes a storage first electrode 1540, a storage second electrode 1740 and a storage third electrode 1960. As shown in FIG. 3, the gate insulating film 1600 and the inter-layer insulating film 1800 are interposed between the storage first electrode 1540 and the storage second electrode 1740, and between the storage second electrode 1740 and the storage third electrode 1960, respectively.

The substrate 1100 may be made of a flexible material such as polyimide, or may be made of rigid material such as glass.

A multi-buffer layer 1200 made of an insulating material such as silicon oxide or silicon nitride is formed on the entire surface over an entire face of the substrate 1100. The multi-buffer layer 1200 is embodied as a stack of multiple layers, for example, at least two layers or more.

A light-blocking layer 1300 is formed on the multi-buffer layer 1200, is made of molybdenum titanium alloy (MoTi) in one example. The light-blocking layer 1300 prevents light from being incident on the active layer 1520, thereby preventing the active layer 1520 from being deteriorated by light. An insulating film 1400 made of an insulating material such as silicon oxide or silicon nitride is formed on the light-blocking layer 1300 over an entire face of the substrate 1100. Alternatively, a contact hole may be formed to connect the active layer 1520 to the light-blocking layer 1300. In order to minimize change in a threshold voltage of the thin film transistor, which may occur when the light-blocking layer 1300 is in a floating state, the light-blocking layer 1300 may be electrically connected to the active layer 1520.

The active layer 1520 embodied as a semiconductor film is formed on the insulating film 1400. The semiconductor film may be made of an oxide semiconductor material, or a single crystal silicon. Alternatively, the active layer 1520 may be made of polycrystalline silicon. In this case, the active layer 1520 may be doped with impurities into both edges thereof.

The storage first electrode 1540 is formed together with the active first layer 1520 on the insulating film 1400. In this connection, the storage first electrode 1540 may be made of polycrystalline silicon in the same manner as the active layer 1520. The storage first electrode 1540 made of polycrystalline silicon is doped with impurities to have conductance.

A gate insulating film 1600 is formed on the insulating film 1400 so that the active layer 1520 and the storage first electrode 1540 are covered with the gate insulating film 1600. The gate insulating film 1600 is formed over an entire face of the substrate 1100. The gate insulating film 1600, for example, may be made of silicon oxide.

A gate electrode 1720 and a storage second electrode 1740 may be formed together on the gate insulating film 1600. The gate electrode 1720 and a storage second electrode 1740 overlap the active layer 1520 and the storage first electrode 1540 respectively. Each of the gate electrode 1720 and the storage second electrode 1740 may be formed of a stack of double metal layers, a first layer made of Cu and a second layer made of MoTi alloy.

An inter-layer insulating film 1800 of insulating material is formed on an entire face of the gate insulating film 1600 to cover the gate electrode 1720 and the storage second electrode 1740. The inter-layer insulating film 1800 may be made of an inorganic insulating material such as silicon oxide or silicon nitride, or made of an organic insulating material such benzocyclobutene or photo-acryl.

As shown in FIG. 3, the gate insulating film 1600 and the inter-layer insulating film 1800 have two active layer contact holes defined therein for exposing both sides of the active layer 1520. The two active layer contact holes are respectively located to be spaced from both sides of the gate electrode 1720.

On the inter-layer insulating film 1800, a source electrode 1920 and a drain electrode 1940 made of a conductive material such as a metal are formed. The source electrode 1920 and the drain electrode 1940 are disposed around the gate electrode 1720 and are spaced from each other. The source electrode 1920 and the drain electrode 1940 are electrically connected to both sides of the active layer 1520 via the two active layer contact holes as described above respectively. The source electrode 1920 is connected to the power line (not shown).

Further, on the inter-layer insulating film 1800, a storage third electrode 1960 defining the storage capacitor Cst and made of a conductive material such as a metal together is formed together with the source electrode 1920 and the drain electrode 1940.

The active layer 1520, the gate electrode 1720, the source electrode 1920, and the drain electrode 1940 constitute the drive thin-film transistor TFT. The drive thin-film transistor TFT has a coplanar structure in which the gate electrode 1720, the source electrode 1920 and the drain electrode 1940 are positioned above the active layer 1520.

Alternatively, the drive thin-film transistor TFT may have an inverted staggered structure where the gate electrode is positioned below the active layer, while the source and drain electrodes are positioned above the active layer. In this case, the active layer may be made of amorphous silicon. In one example, the switching thin-film transistor (not shown) may have substantially the same structure as the drive thin-film transistor TFT.

A planarization layer 2000 having a drain contact-hole defined therein for exposing the drain electrode 1940 of the driving thin-film transistor TFT is formed to cover the drive thin-film transistor TFT and the storage capacitor Cst. The planarization layer 2000 may be made of an inorganic insulating material or an organic insulating material.

A first electrode 3100 is formed on the planarization layer 2000 such that the first electrode 3100 is connected to the drain electrode 1940 of the drive thin-film transistor TFT via the drain contact-hole defined in the planarization layer 2000. Accordingly, the active layer 1520 of the drive thin-film transistor TFT is electrically connected to the first electrode 3100.

The first electrode 3100 may act as an anode, and may be made of a conductive material having a relatively large work function value. For example, the first electrode 3100 may be made of transparent conductive material such as ITO, IZO or ZnO.

In one example, when the organic light-emitting display device 1000 is of a top emission type, a reflective electrode or reflective layer may be further formed below the first electrode 3100. For example, the reflective electrode or reflective layer may be made of any one of aluminum (Al), silver (Ag), nickel (Ni), aluminum-palladium-copper (APC alloy).

A bank layer 2100 is formed on the planarization layer 2000 to define each pixel region. The bank layer 2100 may allow a bank hole corresponding to each pixel region to be defined to partially expose the first electrode 3100.

An organic material layer 3300 is formed on the bank layer 2100 and a portion of the first electrode 3100 exposed by the bank hole. A portion of the organic material layer 3300 that is in contact with the first electrode 3100 corresponds to each pixel region, and more specifically to a light-emission region.

A second electrode 3200 is formed on the organic material layer 3300 over an entire face of the substrate 1100. The second electrode 3200 is positioned on an entirety of the display region and may be made of a conductive material having a relatively small work function value and thus may act as a cathode. For example, the second electrode 3200 may be made of any one of aluminum Al, magnesium Mg, and aluminum-magnesium alloy AlMg.

The first electrode 3100, organic material layer 3300 and second electrode 3200 constitute the organic light-emitting device 3000.

The encapsulating layer 2200 (also refer to as protective film) is formed on the organic light-emitting device 3000 to prevent external moisture from penetrating the organic light-emitting device 3000.

The encapsulating layer 2200 may have, but is not limited to, a triple layer structure (not shown) sequentially composed of a first inorganic layer, and an organic layer, and a second inorganic layer.

The device may comprise a first protective film formed on the second electrode 3200, and a second protective film formed on the first protective film. The first protective film is formed on entire faces of the organic material layer 3300 and second electrode 3200.

On top of the encapsulating layer 2200, a barrier layer 2300 (also refer to as encapsulation film) may be formed to more effectively prevent external moisture or oxygen from invading the organic light-emitting device 3000.

The barrier layer 2300 may be manufactured in a form of a film and adhered to the encapsulating layer 2200 via an adhesive.

The device may comprise an encapsulation film formed on the second protective film, the encapsulation film is bonded to the second protective film via an adhesive film.

Hereinafter, Examples and Comparative Examples will be set forth. The Examples may be only an example of the present disclosure. Thus, the present disclosure is not limited to the Examples.

EXAMPLES

Hereinafter, compounds used in Examples and Comparative Examples were synthesized as follows.

Synthesis Example 1

Compound A

Production of Compound A-1

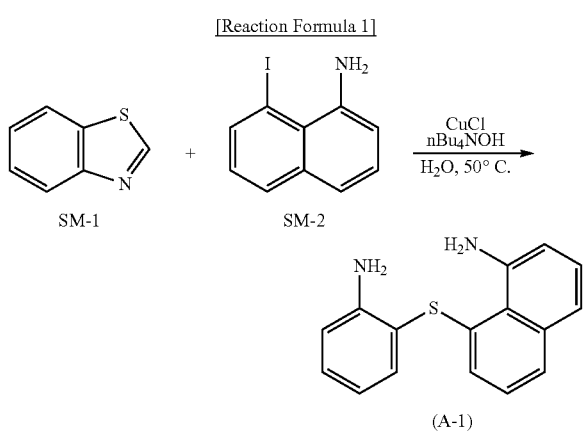

SM-1 (6.8 g, 50 mmol), SM-2 (13.5 g, 50 mmol), CuCl (0.25 g, 2.5 mmol) and nBu$_4$NOH (39 g, 150 mmol) were dissolved into 200 ml water in a 500 ml round bottom flask under a nitrogen atmosphere to form a mixture. Then, the mixture was heated and stirred at 50° C. while being refluxed for 12 hours. After completion of reaction of the mixture, the reacted mixture was cooled to a room temperature, was subjected to extraction using chloroform, and washed with water. Then, water was removed from the washed extracted product using anhydrous magnesium sulfate. Then, the extracted product was concentrated under a reduced pressure. The, the concentrated extracted product was subjected to column chromatography using tetrahydrofuran:hexane=1:5, thereby to prepare the compound A-1 (12.3 g, yield: 92%).

Production of Compound A-2

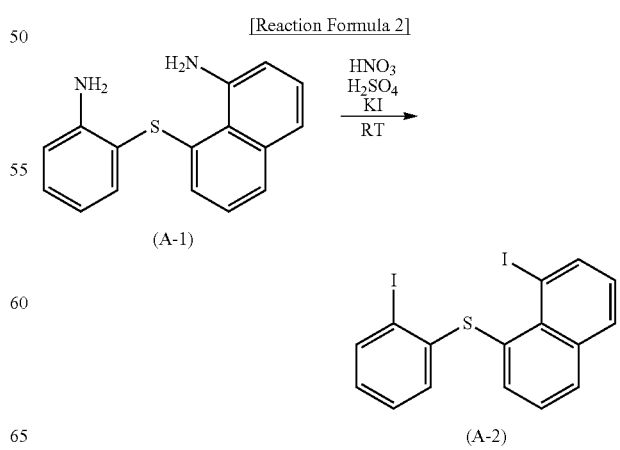

After dissolving A-1 (5.3 g, 20 mmol) in HNO₃ (70%, 50 ml) at 0° C. to form a mixture, H₂SO₄ (95%, 30 ml) was added to the mixture and stirring thereof was continued for 30 minutes at 0° C. KI (8.3 g, 50 mmol) was slowly added dropwise thereto, followed by stirring for 1 hour. The mixture was neutralized with aqueous NaHCO₃ solution at a room temperature. Thus produced precipitate was filtered using a filter and was dried to obtain the compound A-2 (8.1 g, yield: 83%).

Production of Compound A

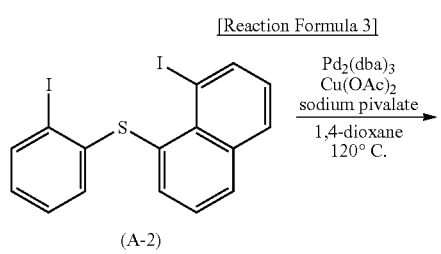

The compound A-2 (7.3 g, 15 mmol), Pd₂(dba)₃ (0.69 g, 0.75 mmol), Cu(OAc)₂ (0.27 g, 1.5 mmol) and sodium pivalate (1.9 g, 15 mmol) were dissolved in 150 ml of 1,4-dioxane, and thus a mixture was obtained. Then, the mixture was heated and stirred while being refluxed for 10 hours. After completion of reaction, the reacted mixture was cooled to a room temperature, and subjected to extracting with chloroform, and an extracted product was washed with water. Water was removed from the extracted product with anhydrous magnesium sulfate. The extracted product was filtered. Then, an organic solvent was distilled under a reduced pressure and was removed from the extracted product, thereby to obtain the compound A (4.2 g, yield: 78%).

Synthesis Example 2

Compound 61

Production of Compound 61

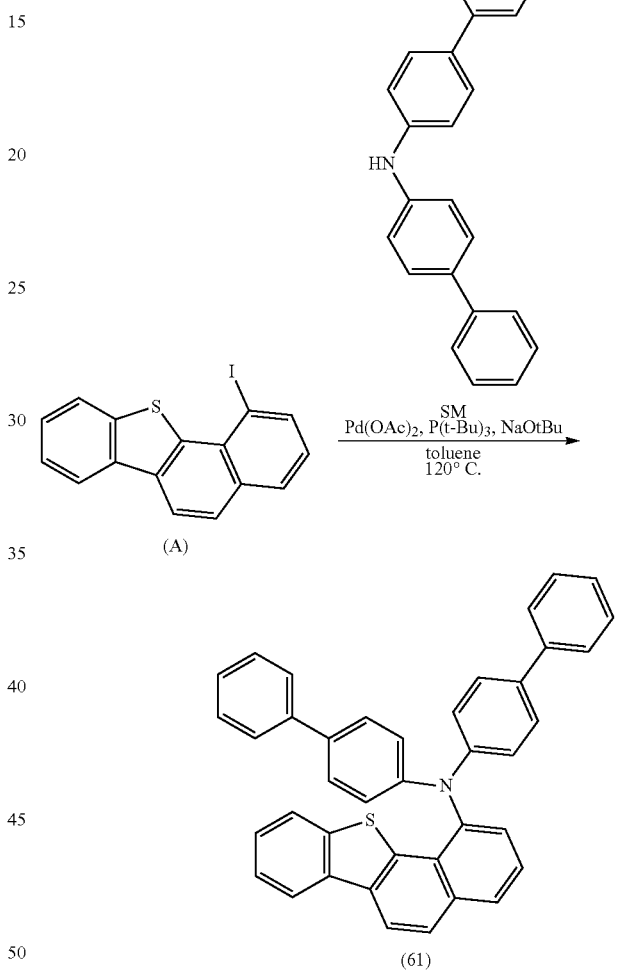

A compound A (7.2 g, 20 mmol), SM (6.4 g, 20 mmol), Pd(OAc)₂ (0.45 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, thereby to obtain the compound 61 (12.5 g, yield: 95%).

Synthesis Example 3

Compound 64

Production of Compound 64

Synthesis Example 4

Compound 67

Production of Compound 67-1

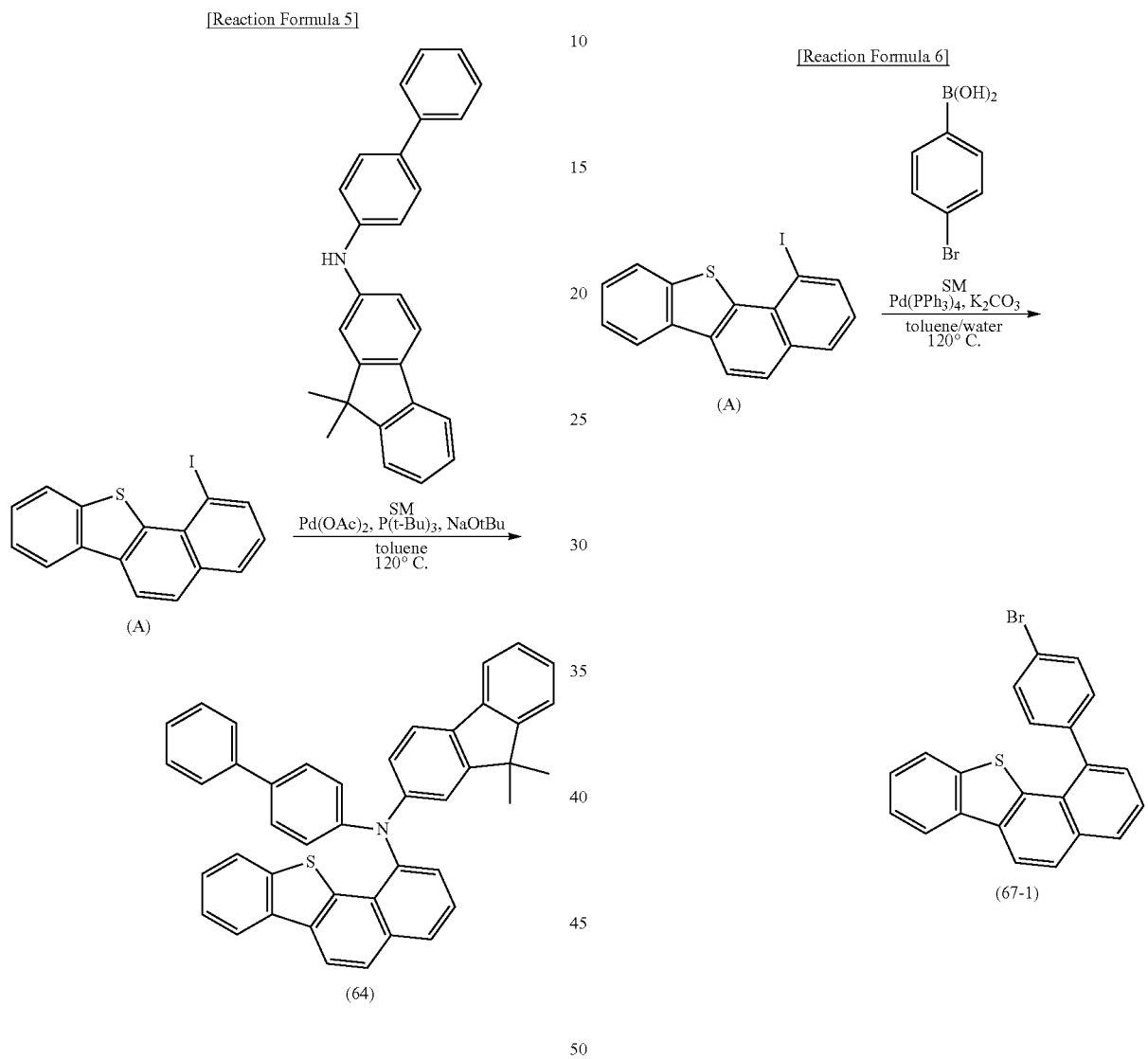

The compound A (7.2 g, 20 mmol), SM (7.2 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 64 (12.5 g, yield: 93%).

The compound A (7.2 g, 20 mmol), SM (4.0 g, 20 mmol), Pd(PPh$_3$)$_4$ (1.2 g, 1 mmol), and K$_2$CO$_3$ (8.3 g, 60 mmol) were dissolved into a mixed solution of toluene 200 ml and water 50 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 67-1 (6.9 g, yield: 89%).

Production of Compound 67

[Reaction Formula 7]

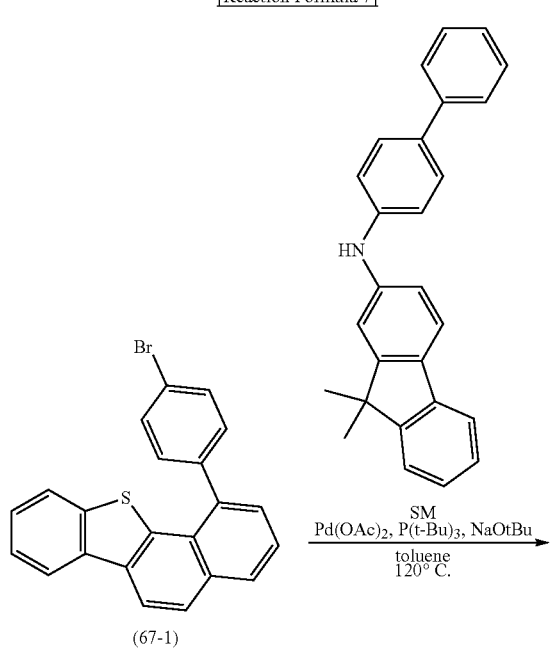

The compound 67-1 (7.8 g, 20 mmol), SM (7.2 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 67 (12.7 g, yield: 95%).

Synthesis Example 5

Compound B

Production of Compound B-1

[Reaction Formula 8]

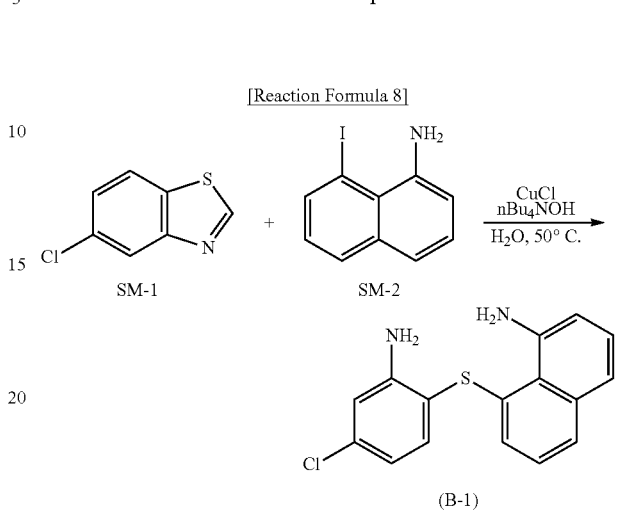

A SM-1 (8.5 g, 50 mmol), SM-2 (13.5 g, 50 mmol), CuCl (0.25 g, 2.5 mmol), and nBu$_4$NOH (39 g, 150 mmol) were dissolved into 200 ml water in a 500 ml round bottom flask under a nitrogen atmosphere to form a mixture. Then, the mixture was heated and stirred at 50° C. while being refluxed for 12 hours. After completion of reaction of the mixture, the reacted mixture was cooled to a room temperature, was subjected to extraction using chloroform, and washed with water. Then, water was removed from the washed extracted product using anhydrous magnesium sulfate. Then, the extracted product was concentrated under a reduced pressure. The, the concentrated extracted product was subjected to column chromatography using tetrahydrofuran:hexane=1:5, thereby to prepare the compound B-1 (13.2 g, yield: 88%).

Production of Compound B-2

[Reaction Formula 9]

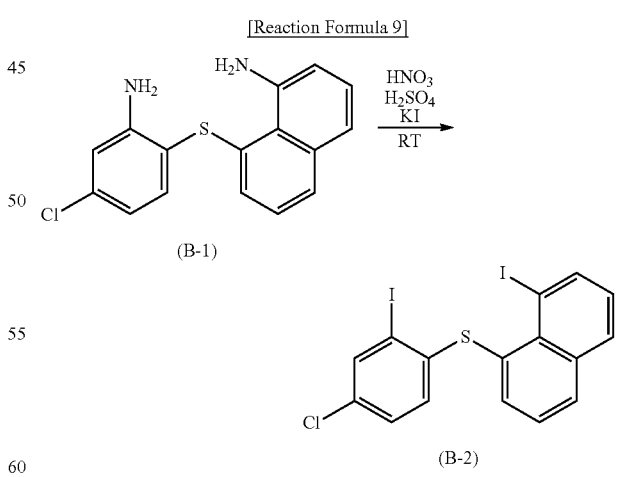

After dissolving B-1 (6.0 g, 20 mmol) in HNO$_3$ (70%, 50 ml) at 0° C. to form a mixture, H$_2$SO$_4$ (95%, 30 ml) was added to the mixture and stirring thereof was continued for 30 minutes at 0° C. KI (8.3 g, 50 mmol) was slowly added dropwise thereto, followed by stirring for 1 hour. The mixture was neutralized with aqueous NaHCO$_3$ solution at a room temperature. Thus produced precipitate was filtered using a filter and was dried to obtain the compound B-2 (8.4 g, yield: 80%).

Production of Compound B

[Reaction Formula 10]

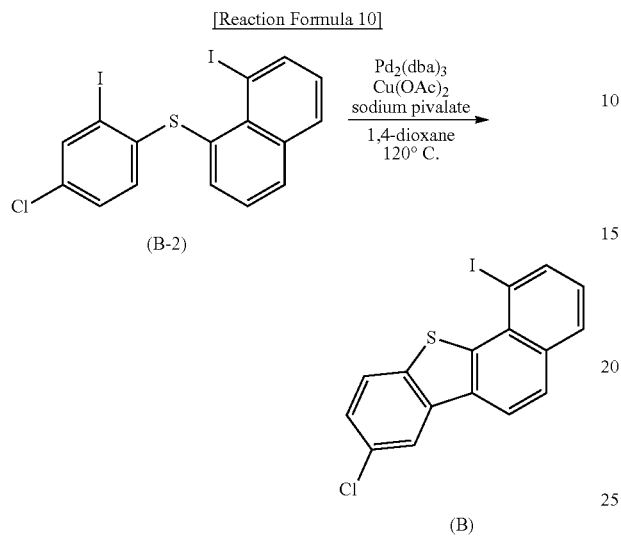

The compound B-2 (7.8 g, 15 mmol), Pd$_2$(dba)$_3$ (0.69 g, 0.75 mmol), Cu(OAc)$_2$ (0.27 g, 1.5 mmol) and sodium pivalate (1.9 g, 15 mmol) were dissolved in 150 ml of 1,4-dioxane, and thus a mixture was obtained. Then, the mixture was heated and stirred while being refluxed for 10 hours. After completion of reaction, the reacted mixture was cooled to a room temperature, and subjected to extracting with chloroform, and an extracted product was washed with water. Water was removed from the extracted product with anhydrous magnesium sulfate. The extracted product was filtered. Then, an organic solvent was distilled under a reduced pressure and was removed from the extracted product, thereby to obtain the compound B (4.4 g, yield: 75%).

Synthesis Example 6

Compound 78

Production of Compound 78-1

[Reaction Formula 11]

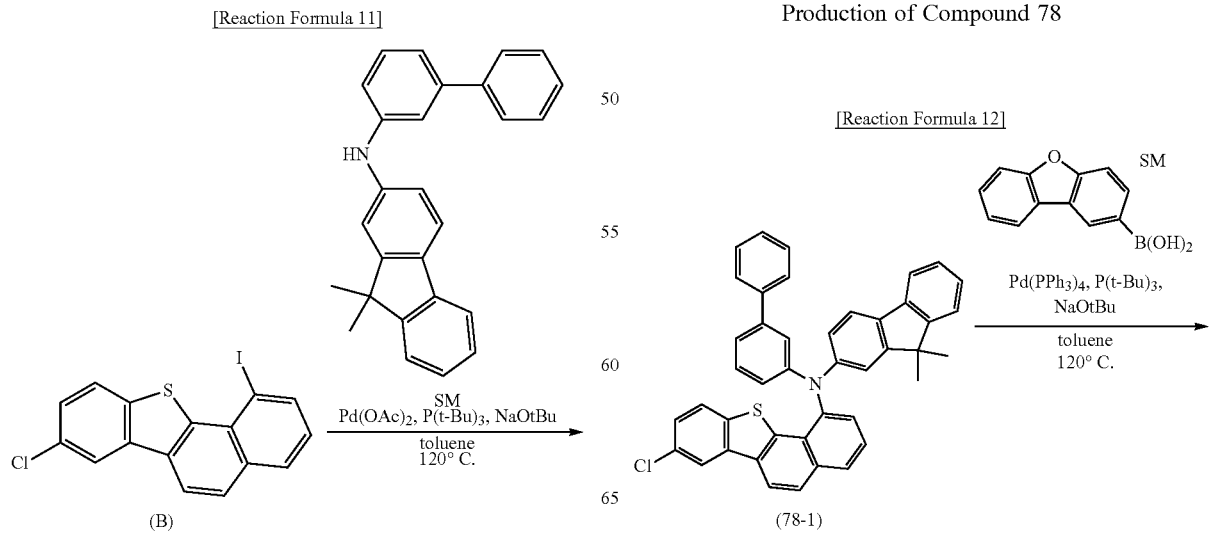

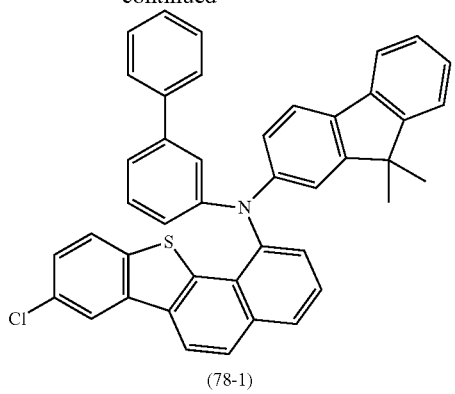

The compound B (7.9 g, 20 mmol), SM (7.2 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 78-1 (11.4 g, yield: 91%).

Production of Compound 78

[Reaction Formula 12]

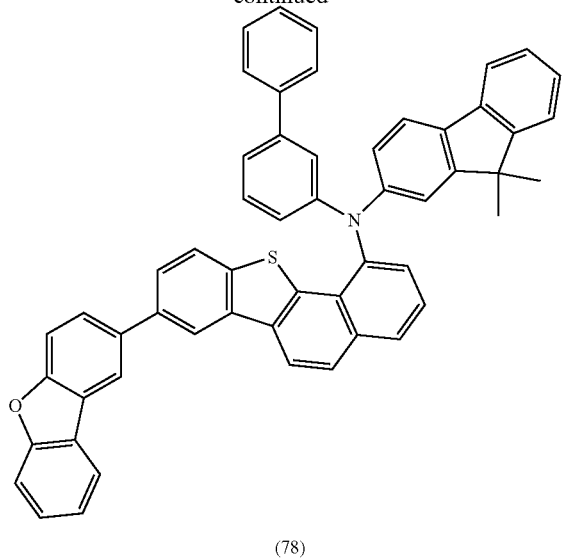

(78)

The compound 78-1 (12.6 g, 20 mmol), SM (4.3 g, 20 mmol), Pd(PPh₃)₄ (2.3 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 78 (12.5 g, yield: 82%).

Synthesis Example 7

Compound C

Production of Compound C-1

[Reaction Formula 13]

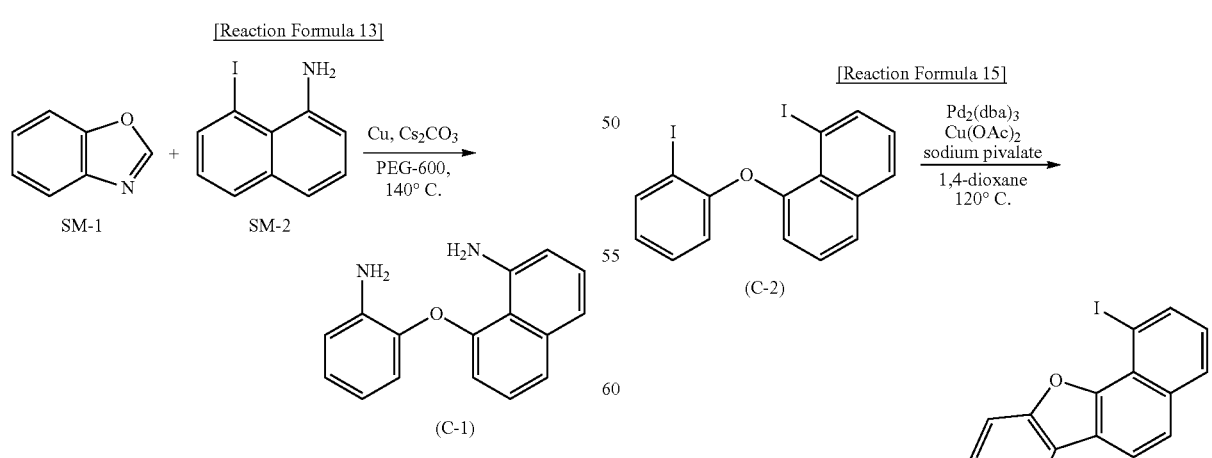

(C-1)

A SM-1 (6.0 g, 50 mmol), SM-2 (13.5 g, 50 mmol), Cu (0.32 g, 5 mmol) and Cs₂CO₃ (32.6 g, 100 mmol) were added to PEG-600 100 g in a 500 ml round bottom flask under a nitrogen atmosphere to form a mixture. Then, the mixture was heated and stirred while being refluxed at 140 degrees C. for 12 hours. After completion of reaction, the reacted mixture was cooled to room temperature, was subjected to extraction with ethyl acetate (EA), and the extracted product was washed with aqueous NaCl solution. Water was removed from the extracted product with anhydrous magnesium sulfate. The extracted product was concentrated under a reduced pressure and was subjected to column chromatography with petroleum ether:diethyl ether:triethylamine=30:1:1. Thus, the compound C-1 (11 g, yield: 88%) was produced.

Production of Compound C-2

[Reaction Formula 14]

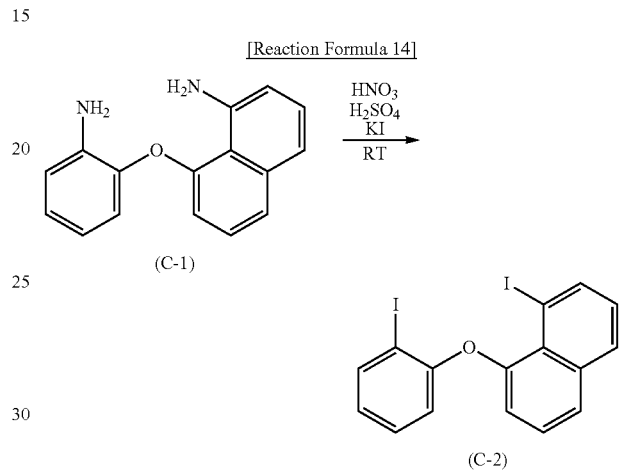

After dissolving C-1 (5.0 g, 20 mmol) in HNO₃ (70%, 50 ml) at 0° C. to form a mixture, H₂SO₄ (95%, 30 ml) was added to the mixture and stirring thereof was continued for 30 minutes at 0° C. KI (8.3 g, 50 mmol) was slowly added dropwise thereto, followed by stirring for 1 hour. The mixture was neutralized with aqueous NaHCO₃ solution at a room temperature. Thus produced precipitate was filtered using a filter and was dried to obtain the compound C-2 (8.2 g, yield: 87%).

Production of Compound C

[Reaction Formula 15]

The compound C-2 (7.1 g, 15 mmol), Pd$_2$(dba)$_3$ (0.69 g, 0.75 mmol), Cu(OAc)$_2$ (0.27 g, 1.5 mmol) and sodium pivalate (1.9 g, 15 mmol) were dissolved in 150 ml of 1,4-dioxane, and thus a mixture was obtained. Then, the mixture was heated and stirred while being refluxed for 10 hours. After completion of reaction, the reacted mixture was cooled to a room temperature, and subjected to extracting with chloroform, and an extracted product was washed with water. Water was removed from the extracted product with anhydrous magnesium sulfate. The extracted product was filtered. Then, an organic solvent was distilled under a reduced pressure and was removed from the extracted product, thereby to obtain the compound C (4.1 g, yield: 80%).

Synthesis Example 8

Compound 6

Production of Compound 6

The compound C (6.9 g, 20 mmol), SM (8.8 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 6 (11.9 g, yield: 91%).

[Production of Organic Light-Emitting Device 1]

<Compound Used in Organic Light-Emitting Device 1>

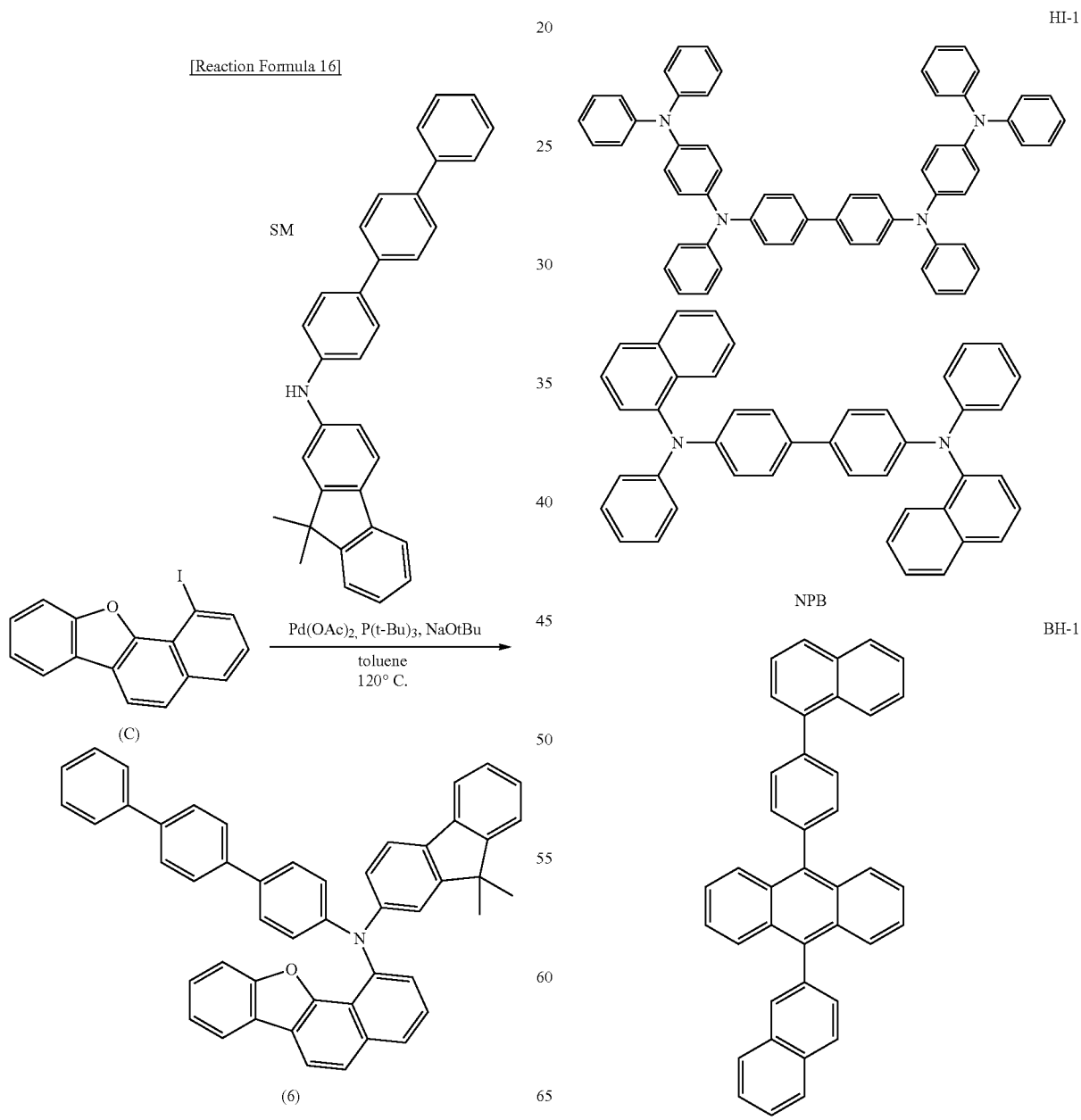

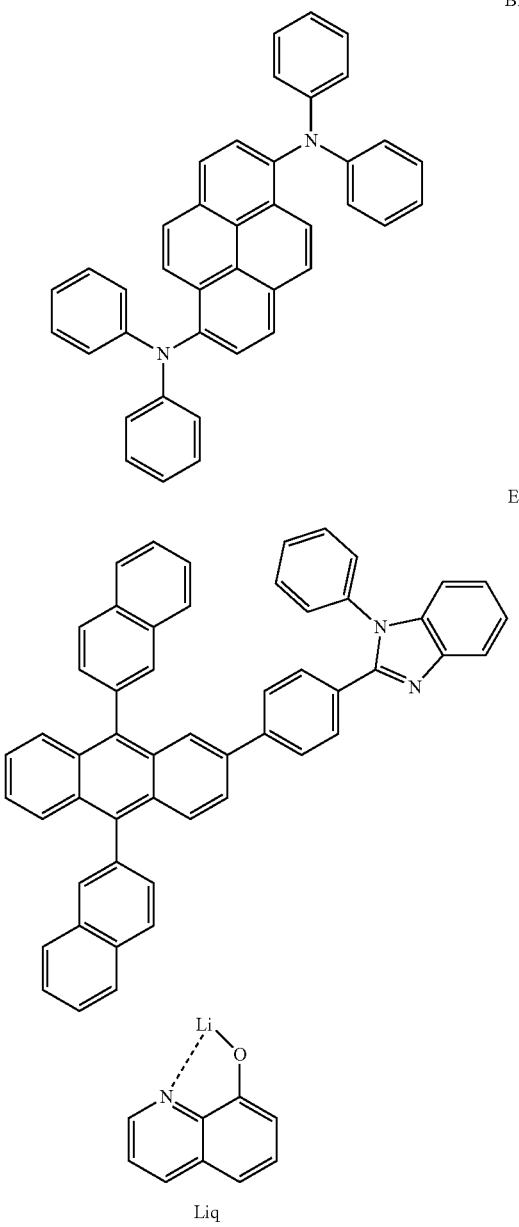

BD-1

ET-1

Liq

Example 1

After cleaning a glass substrate having a ITO (indium tin oxide) thin film coated thereon to a thickness of 1,000 Å, the substrate was ultrasonically washed with a solvent such as isopropyl alcohol, acetone, or methanol and dried. Then, HI-1 as a hole injection material was deposited to a thickness of 60 nm on the ITO transparent electrode via thermal vacuum deposition. Then, the Compound 3 as a hole transport material was thermally vacuum deposited to 80 nm thickness on the hole injection material. Subsequently, BH-1 and BD-1 was used as a host material and a dopant material (5 wt %) in a light-emitting layer respectively. Thus, the host material was thermally vacuum-deposited to a thickness of 30 nm on the hole transport material while the dopants were doped into the host material, thus form the light-emitting layer.

Then, a ET-1:Liq (1:1) compound was thermally vacuum deposited at 30 nm thickness as each of electron transport layer material and electron injection layer material on the light-emitting layer. Then, depositing aluminum as cathode material at a thickness of 100 nm on the electron injection layer resulted in an organic light-emitting device 1.

Examples 2 to 14

Organic light-emitting devices 1 were fabricated in the same manner as in Example 1 except that compounds shown in Table 1 were used in place of the compound 3 in the Example 1.

Comparative Example 1

An organic light-emitting device 1 was fabricated in the same manner as in Example 1 except that NPB compound was used instead of the compound 3 in the Example 1.

The organic light-emitting devices produced in Examples 1 to 14 and Comparative Example 1 were analyzed in terms of optical characteristic of the device at a constant current of 10 mA/cm$^2$. The organic light-emitting devices produced in Examples 1 to 14 and Comparative Example 1 were analyzed in terms of a lifespan under a driving condition of 20 mA/cm$^2$. Results thereof are shown in Table 1 below.

TABLE 1

| Examples | Hole transport material | Drive voltage (V) | mA/cm$^2$ | Cd/A | lm/W | CIEx | CIEy | LT95 (hrs) |
|---|---|---|---|---|---|---|---|---|
| Comparative Example 1 | NPB | 4.52 | 100% | 100% | 100% | 0.141 | 0.110 | 100% |
| Example 1 | Compound 3 | 4.09 | 108% | 106% | 101% | 0.141 | 0.110 | 124% |
| Example 2 | Compound 6 | 4.03 | 110% | 108% | 103% | 0.141 | 0.110 | 128% |
| Example 3 | Compound 7 | 4.01 | 115% | 111% | 106% | 0.140 | 0.110 | 135% |
| Example 4 | Compound 8 | 4.02 | 116% | 113% | 109% | 0.141 | 0.111 | 141% |
| Example 5 | Compound 14 | 4.08 | 107% | 105% | 102% | 0.140 | 0.111 | 127% |
| Example 6 | Compound 19 | 4.03 | 110% | 108% | 105% | 0.141 | 0.110 | 139% |
| Example 7 | Compound 24 | 4.02 | 119% | 115% | 109% | 0.141 | 0.110 | 149% |
| Example 8 | Compound 61 | 4.08 | 109% | 107% | 106% | 0.140 | 0.111 | 134% |
| Example 9 | Compound 64 | 4.16 | 114% | 110% | 111% | 0.139 | 0.110 | 138% |
| Example 10 | Compound 65 | 4.05 | 118% | 113% | 115% | 0.140 | 0.110 | 147% |
| Example 11 | Compound 67 | 4.21 | 122% | 119% | 118% | 0.141 | 0.110 | 146% |
| Example 12 | Compound 70 | 4.11 | 127% | 121% | 120% | 0.141 | 0.111 | 148% |

TABLE 1-continued
| Examples | Hole transport material | Drive voltage (V) | mA/cm² | Cd/A | lm/W | CIEx | CIEy | LT95 (hrs) |
|---|---|---|---|---|---|---|---|---|
| Example 13 | Compound 77 | 4.04 | 120% | 116% | 116% | 0.141 | 0.110 | 149% |
| Example 14 | Compound 78 | 4.38 | 128% | 122% | 120% | 0.141 | 0.111 | 152% |
[Production of Organic Light-Emitting Device 2]
<Compound Used in Organic Light-Emitting Device 2>
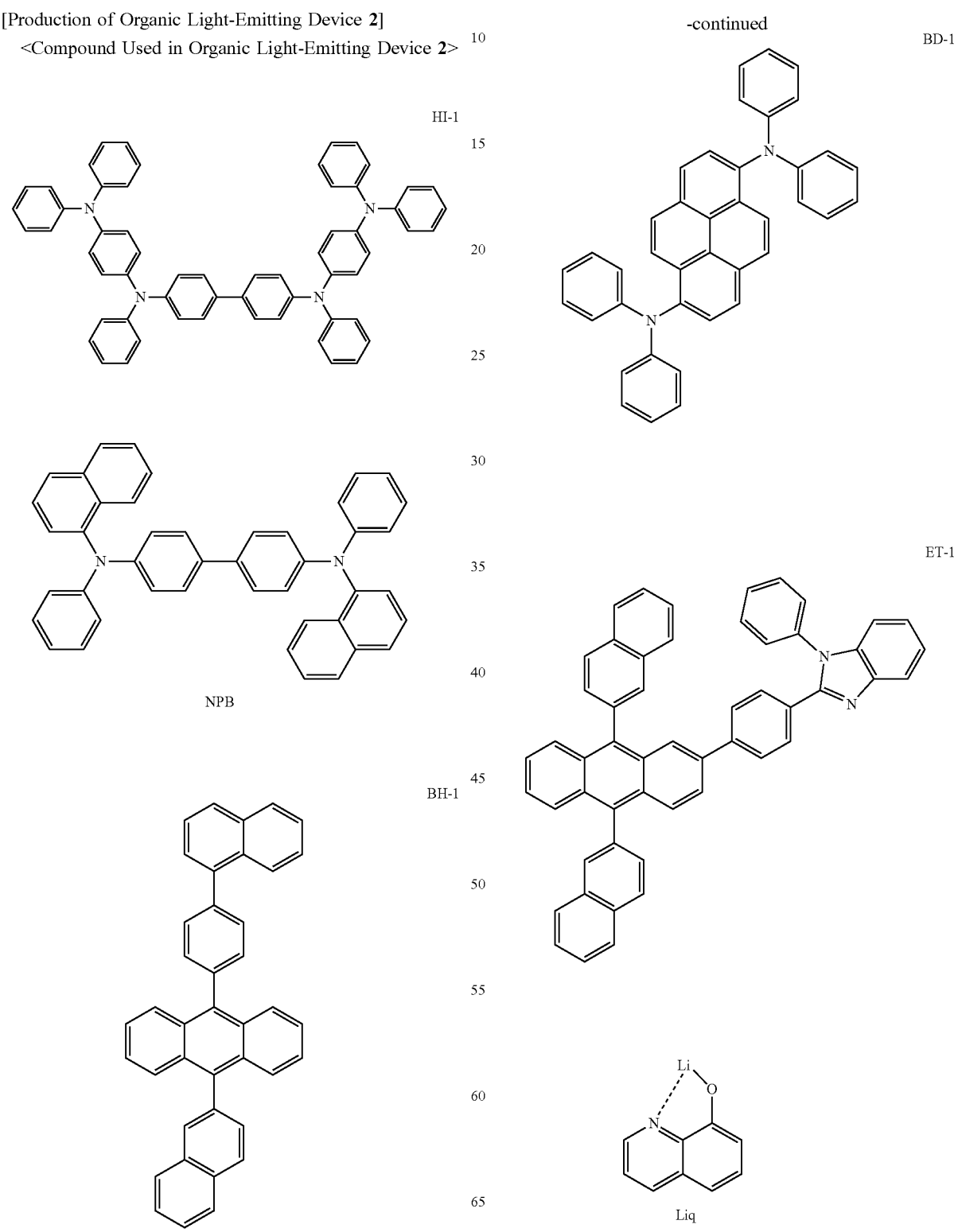

-continued

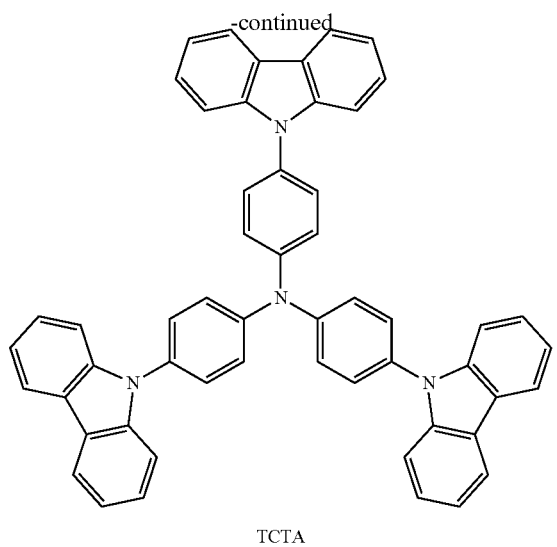

TCTA

Examples 16 to 17

Organic light-emitting devices 2 were fabricated in the same manner as in Example 15 except that compounds shown in Table 2 were used in place of the compound 34 in the Example 15.

Comparative Example 2

An organic light-emitting device 2 was fabricated in the same manner as in Example 15 except that the TCTA compound was used instead of the compound 34 in the Example 15.

The organic light-emitting devices produced in Examples 15 to 17 and Comparative Example 2 were analyzed in terms of optical characteristic of the device at a constant current of 10 mA/cm$^2$. The organic light-emitting devices produced in Examples 15 to 17 and Comparative Example 2 were analyzed in terms of a lifespan under a driving condition of 20 mA/cm$^2$. Results thereof are shown in Table 2 below.

TABLE 2

| Examples | Electron blocking layer material | Drive voltage (V) | mA/Cm$^2$ | Cd/A | lm/W | CIEx | CIEy | LT95 (hrs) |
|---|---|---|---|---|---|---|---|---|
| Comparative Example 2 | TCTA | 4.58 | 100% | 100% | 100% | 0.141 | 0.110 | 100% |
| Example 15 | Compound 34 | 4.42 | 120% | 119% | 117% | 0.141 | 0.110 | 110% |
| Example 16 | Compound 84 | 4.45 | 126% | 122% | 120% | 0.141 | 0.111 | 121% |
| Example 17 | Compound 85 | 4.41 | 129% | 126% | 120% | 0.140 | 0.111 | 122% |

Example 15

After cleaning a glass substrate having a ITO (indium tin oxide) thin film coated thereon to a thickness of 1,000 Å, the substrate was ultrasonically washed with a solvent such as isopropyl alcohol, acetone, or methanol and dried. Then, HI-1 as a hole injection material was deposited to a thickness of 60 nm on the ITO transparent electrode via thermal vacuum deposition. Then, the NPB compound as a hole transport material was thermally vacuum deposited to 80 nm thickness on the hole injection material. Subsequently, the Compound 34 as an electron blocking layer material was thermally vacuum deposited to a thickness of 10 nm on the hole injection material layer. Subsequently, BH-1 and BD-1 was used as a host material and a dopant material (5 wt %) in a light-emitting layer respectively. Thus, the host material was thermally vacuum-deposited to a thickness of 30 nm on the hole transport material while the dopants were doped into the host material, thus form the light-emitting layer. Then, a ET-1:Liq (1:1) compound was thermally vacuum deposited at 30 nm thickness as each of electron transport layer material and electron injection layer material on the light-emitting layer. Then, depositing aluminum as cathode material at a thickness of 100 nm on the electron injection layer resulted in an organic light-emitting device 2.

As described above, the present disclosure is described with reference to the drawings. However, the present disclosure is not limited by the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

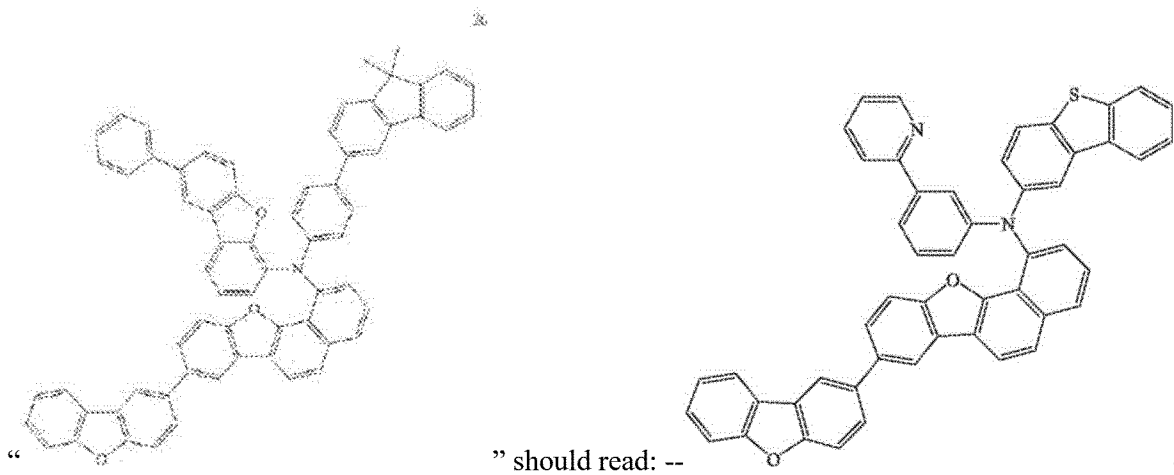

What is claimed is:

1. An organic light-emitting device comprising:
   a first electrode;
   a second electrode;
   at least one organic material layer between the first and second electrodes;
   a first protective film on the second electrode;
   a second protective film on the first protective film; and
   a driving thin-film transistor including an active layer electrically connected to the first electrode,
   wherein:
   the active layer comprises an oxide semiconductor layer; and
   the organic material layer comprises a compound represented by the following Chemical Formula 1:

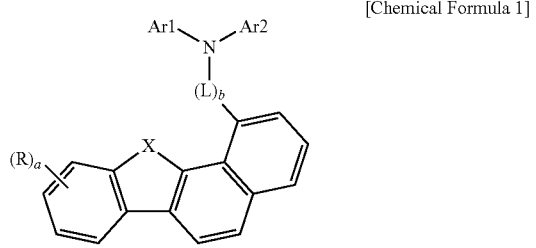

[Chemical Formula 1]

wherein:
X is O or S,
R represents one selected from the group consisting of an aryl group having 6 to 30 carbon atoms, an amino group, a heterocyclic group having 3 to 30 carbon atoms and including at least one hetero atom selected from the group consisting of O, N and S, an alkyl group having 1 to 30 carbon atoms, an alkenyl group having 2 to 30 carbon atoms, an alkynyl group having 2 to 30 carbon atoms, an alkoxy group having 1 to 30 carbon atoms, and an aryloxy group having 6 to 30 carbon atoms,
a is an integer from 0 to 4, provided when a is 2 or greater, each R is the same as or different from each other, or adjacent R groups are bonded to each other to form a ring,
L represents a direct bond or represents one selected from the group consisting of substituted or unsubstituted arylene having 6 to 30 carbon atoms and substituted or unsubstituted heteroarylene having 3 to 30 carbon atoms,
b is an integer from 0 to 4, and
each of Ar1 and Ar2 independently represents one selected from the group consisting of a substituted or unsubstituted C6 to C60 aryl group, a C3 to C30 heteroaryl group containing at least one heteroatom selected from the group consisting of O, N and S, an alkyl group having 1 to 30 carbon atoms, an alkenyl group having 2 to 30 carbon atoms, an alkynyl group having 2 to 30 carbon atoms, an alkoxyl group having 1 to 30 carbon atoms, and an aryloxy group having from 6 to 30 carbon atoms.

2. The organic light-emitting device of claim 1, wherein the at least one organic material layer comprises at least one layer selected from the group consisting of a hole transport layer and an auxiliary hole transport layer.

3. The organic light-emitting device of claim 2, wherein the at least one organic material layer comprises at least two compounds represented by Chemical Formula 1.

4. The organic light-emitting device of claim 1, wherein the at least one organic material layer comprises at least one layer selected from the group consisting of a hole injection layer, a hole transport layer, an auxiliary hole transport layer, a light-emitting layer, an auxiliary electron transport layer, an electron transport layer, and an electron injection layer.

5. The organic light-emitting device of claim 1, wherein the first protective film is on entire faces of the at least one organic material layer and the second electrode.

6. The organic light-emitting device of claim 1, further comprising an encapsulation film on the second protective film, wherein the encapsulation film is bonded to the second protective film via an adhesive film.

7. The organic light-emitting device of claim 1, wherein the driving thin-film transistor further comprises a gate insulating film on the active layer, and a gate electrode on the gate insulating film.

8. The organic light-emitting device of claim 1, wherein each of R, L, Ar1 and Ar2 is independently free of carbazole.

9. The organic light-emitting device of claim 1, wherein each of Ar1 and Ar2 is independently selected from the following substituents:

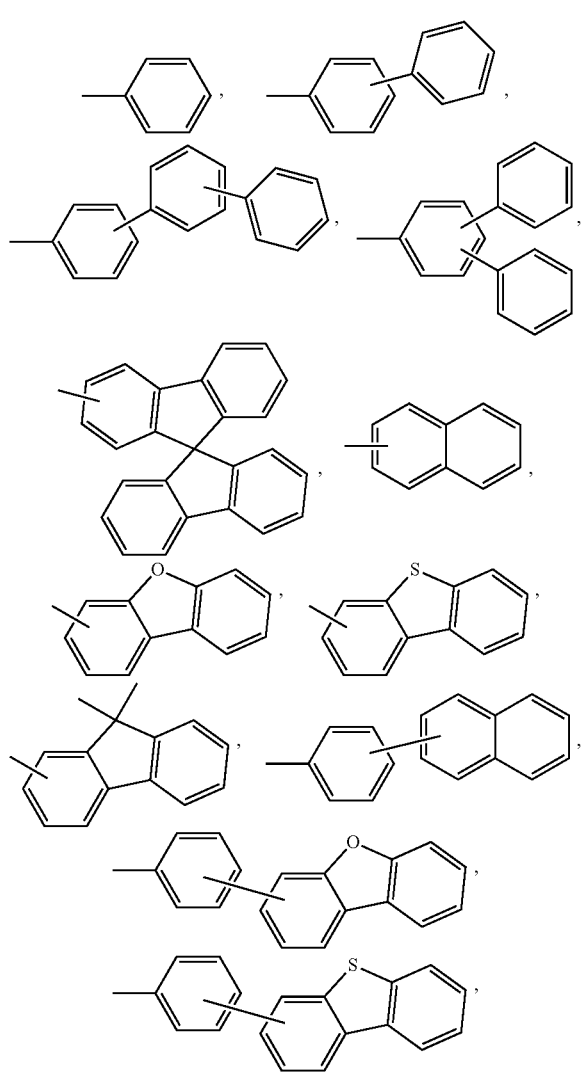

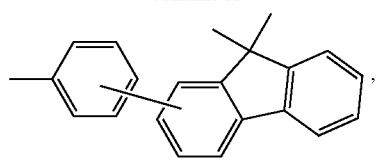
10. The organic light-emitting device of claim 1, wherein the compound is represented by one of the following compounds:
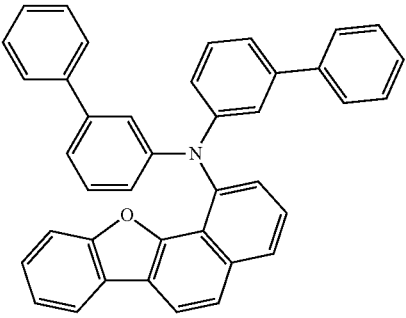
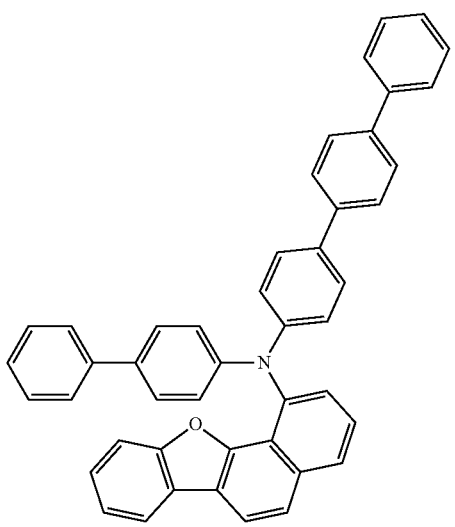
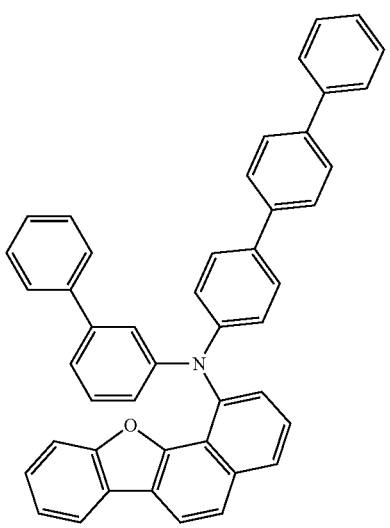

-continued
6
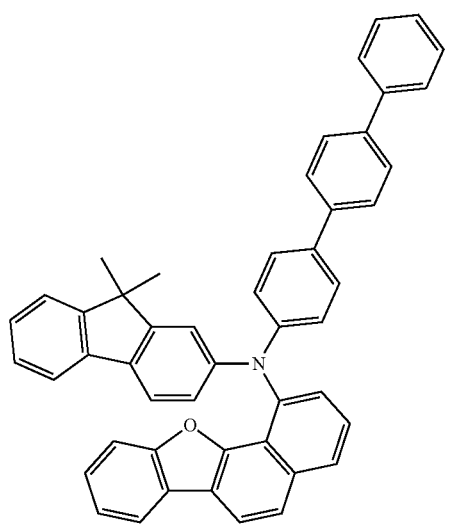
7
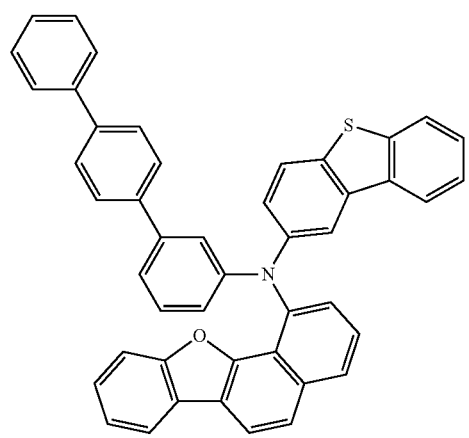
8
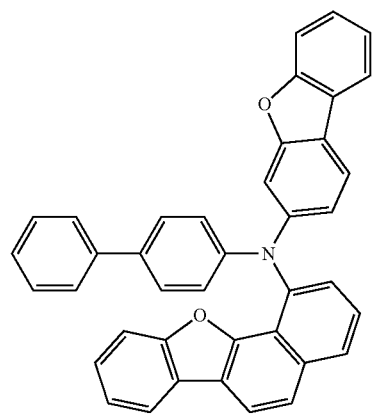
-continued
9
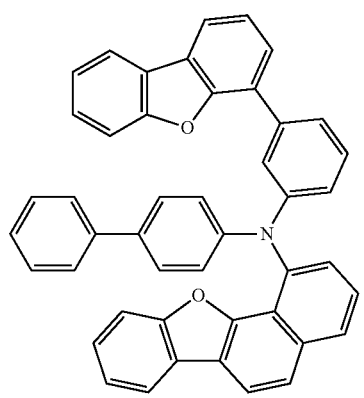
10
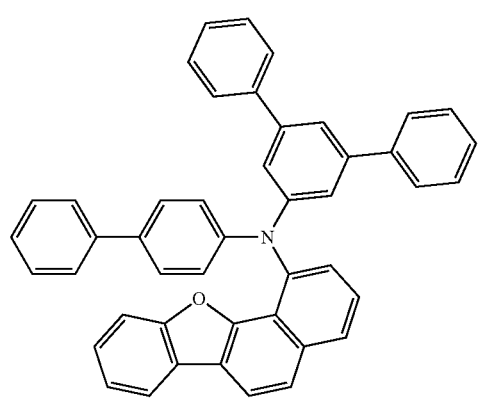
11
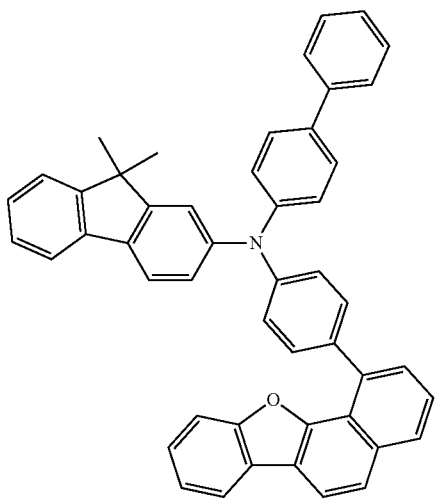

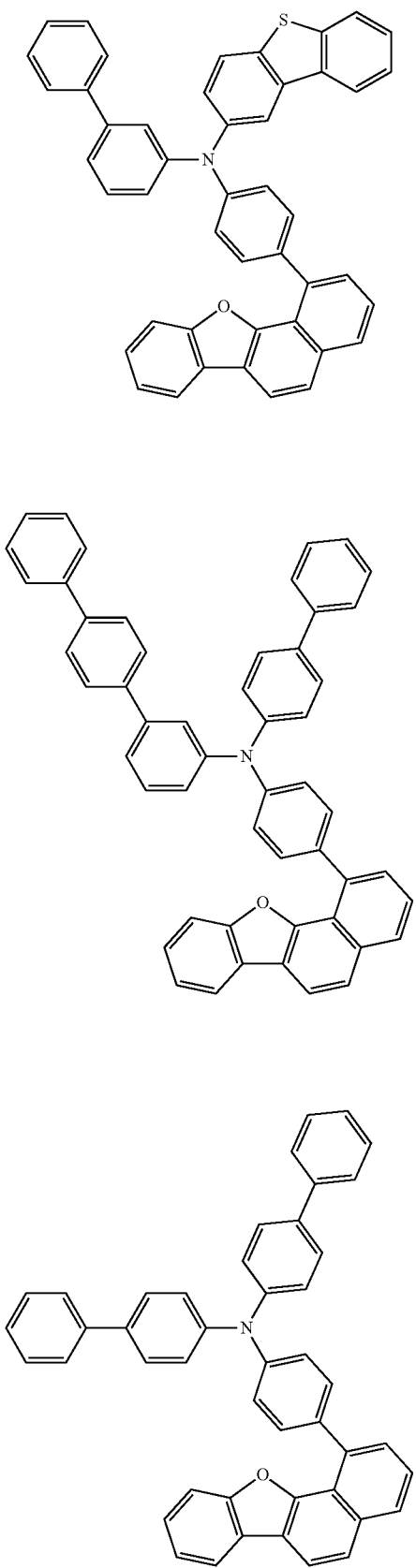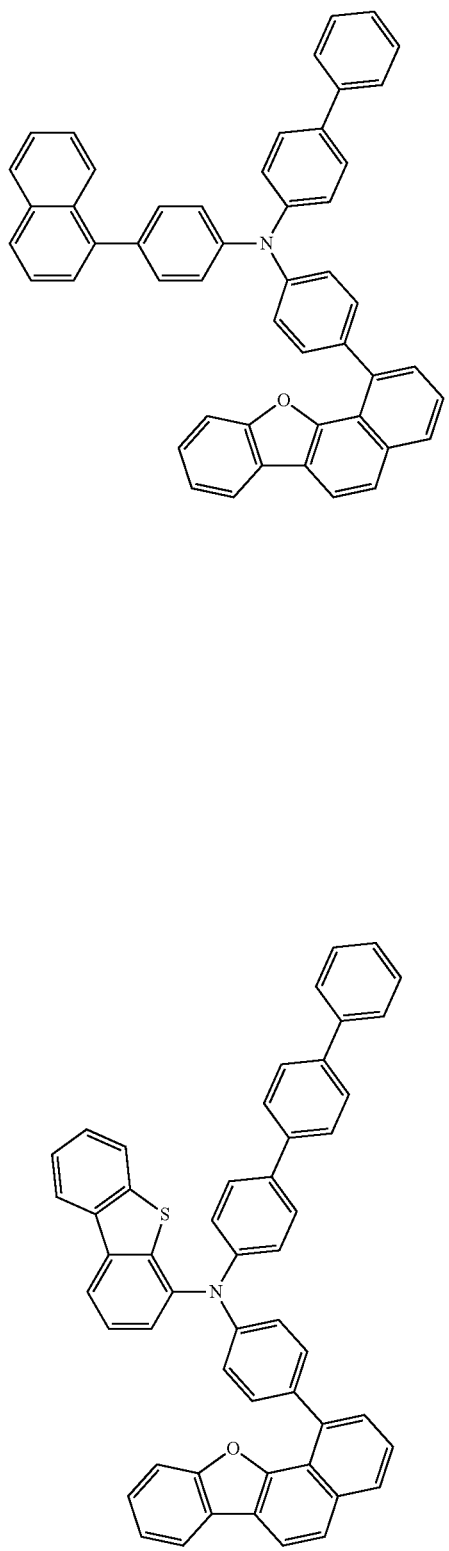

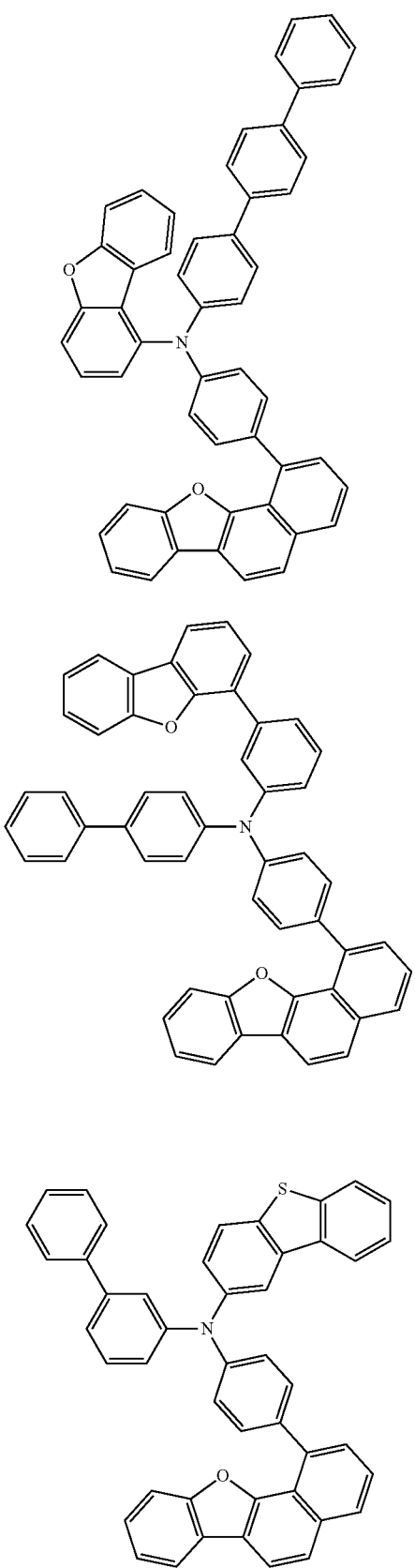
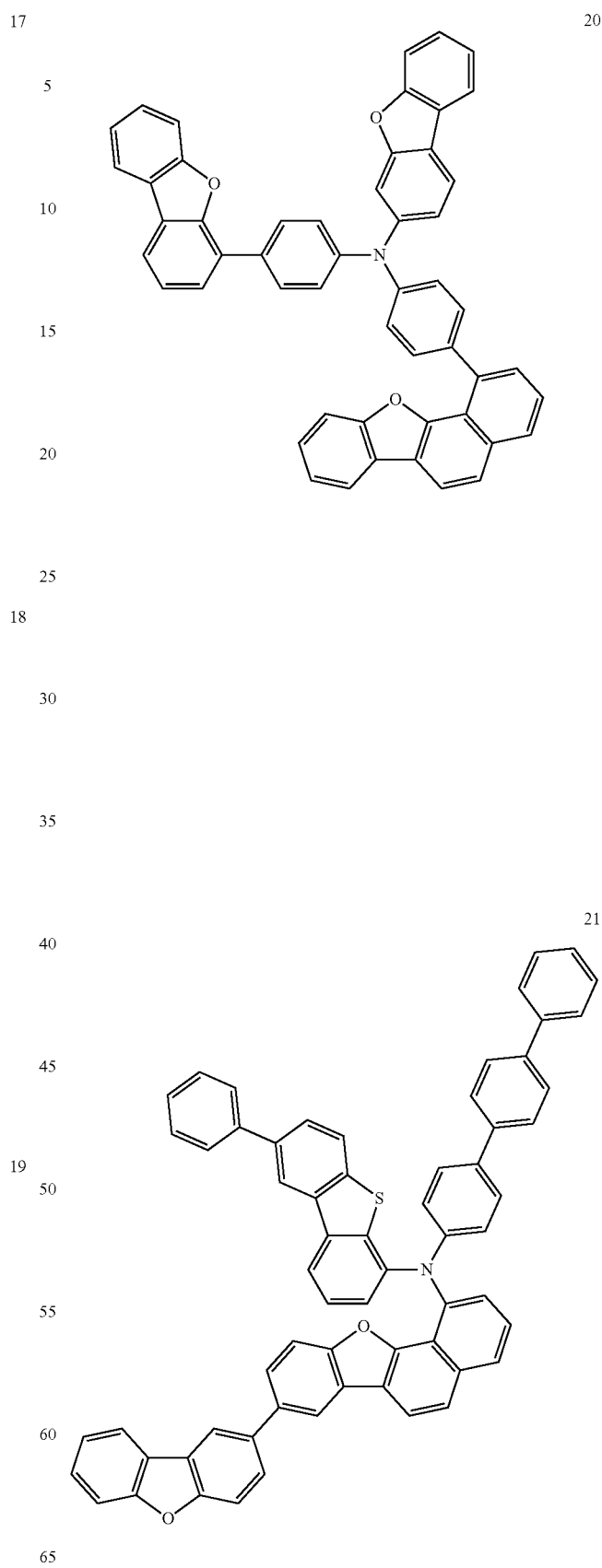

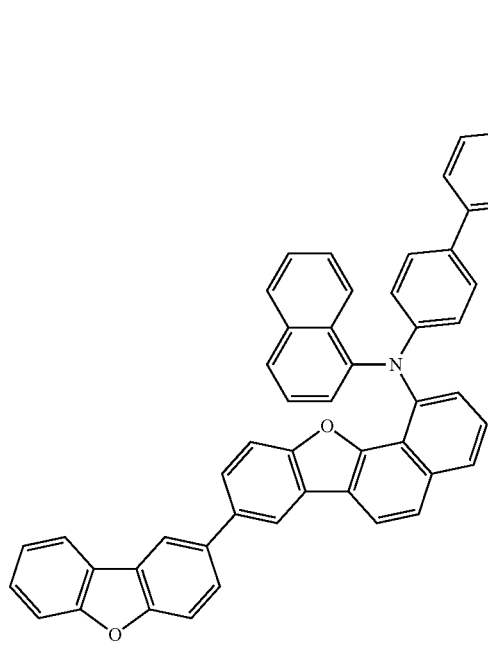
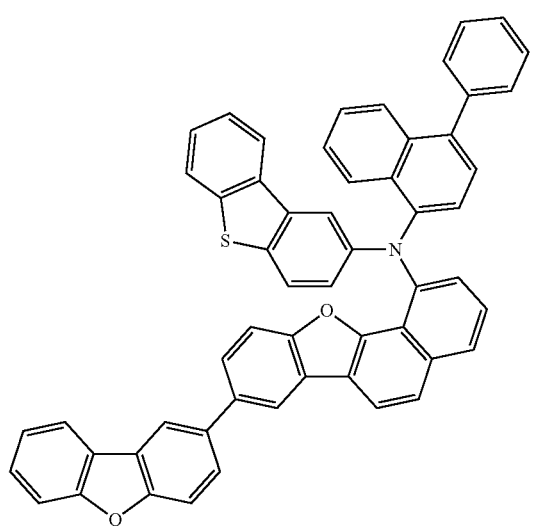
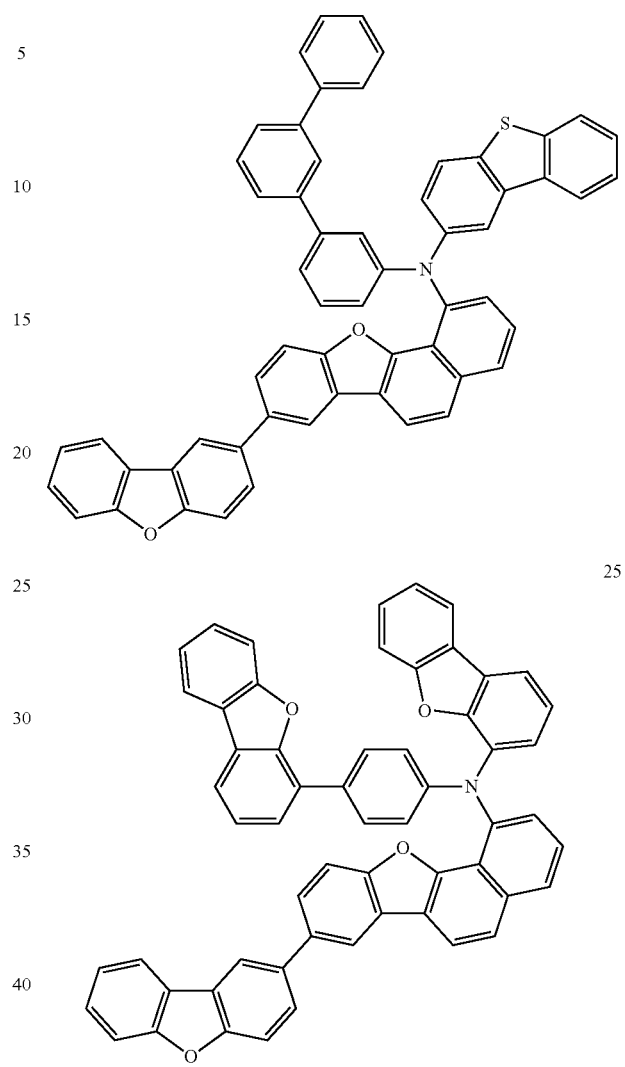

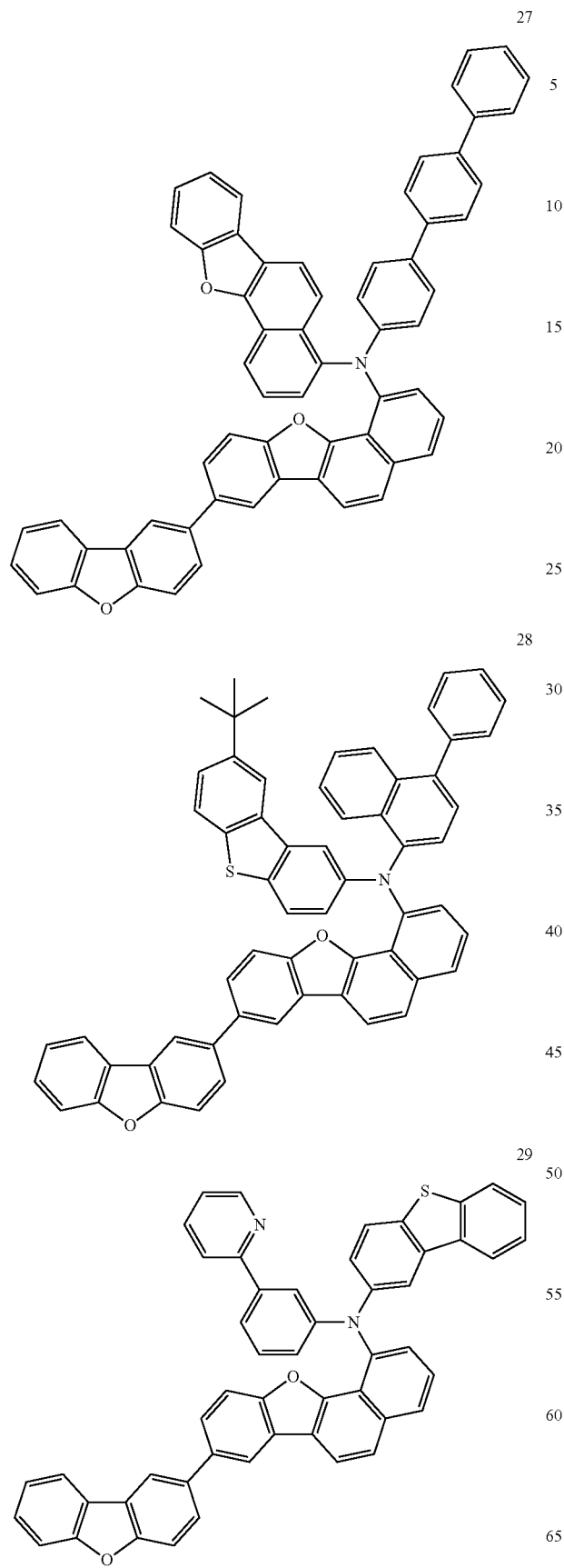
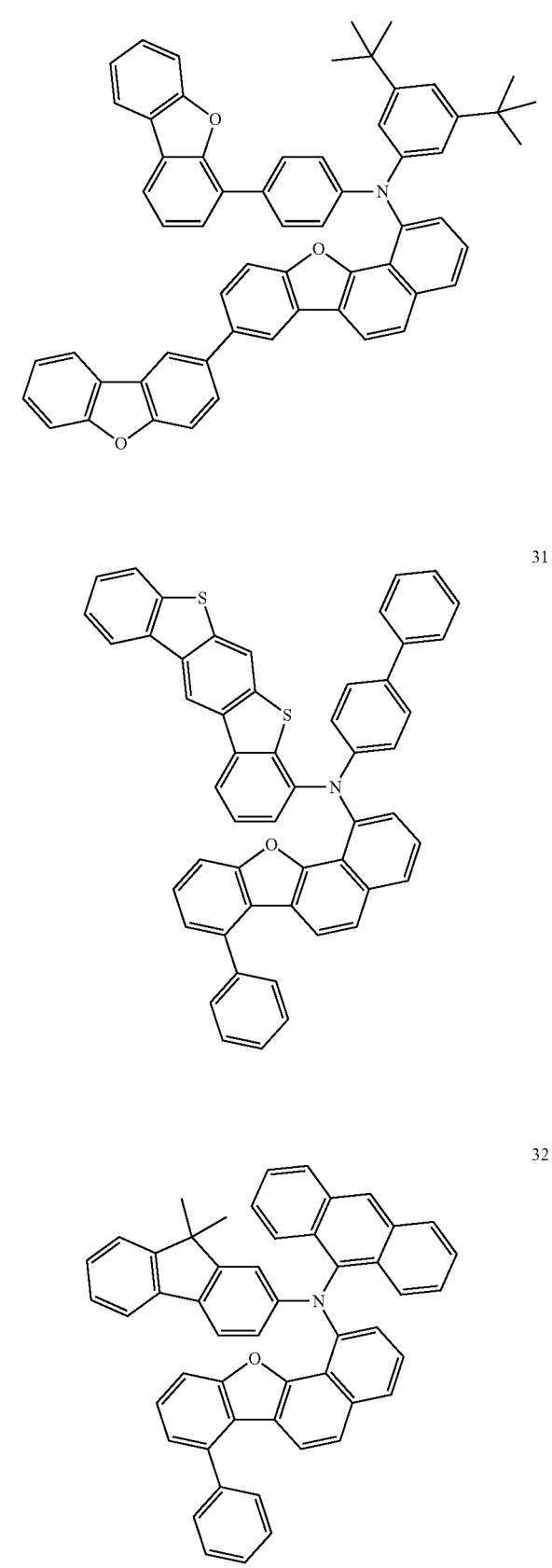

33
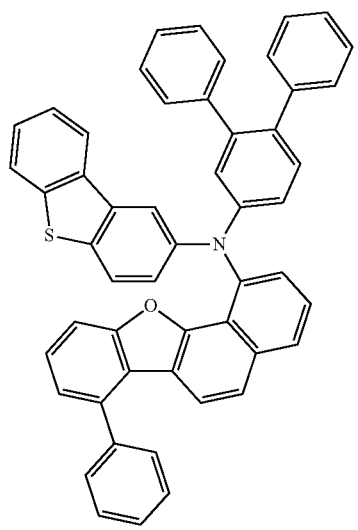
34
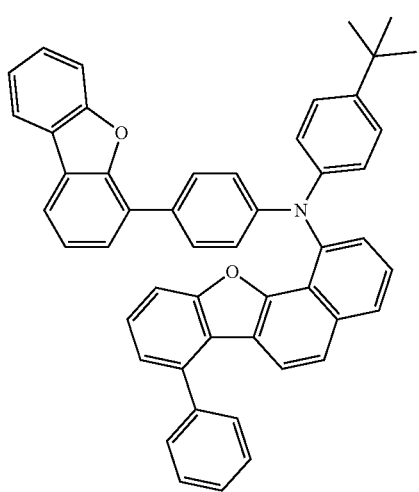
35
36
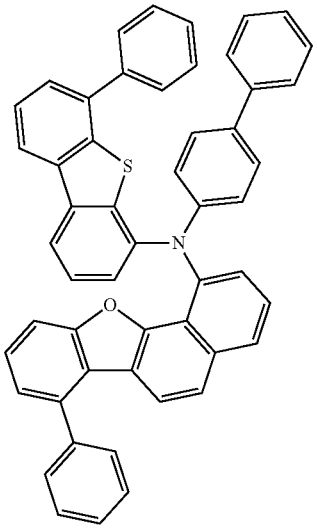
37
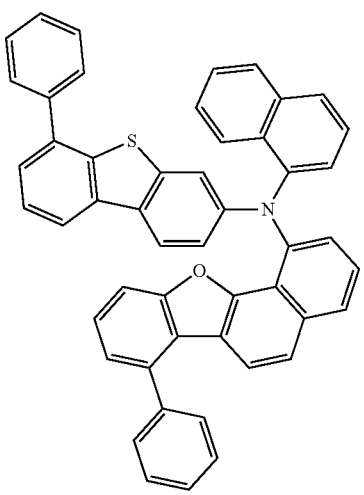
38

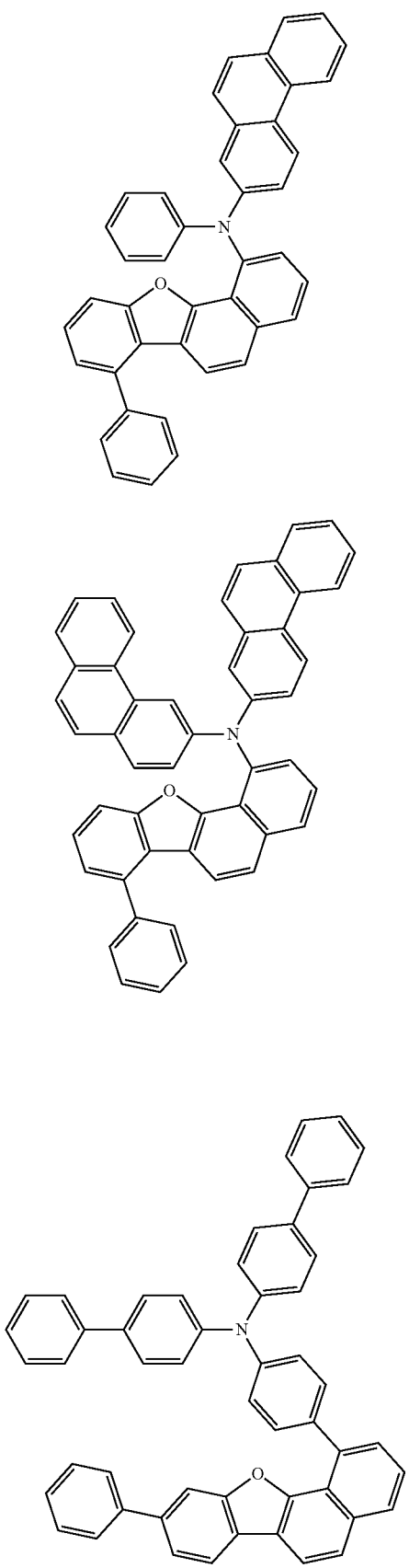
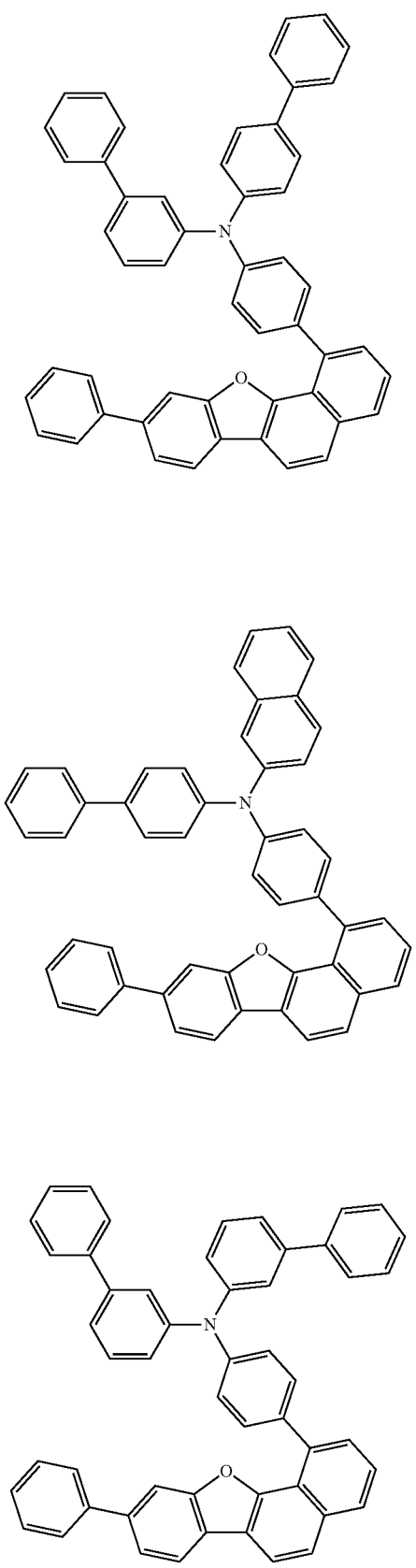

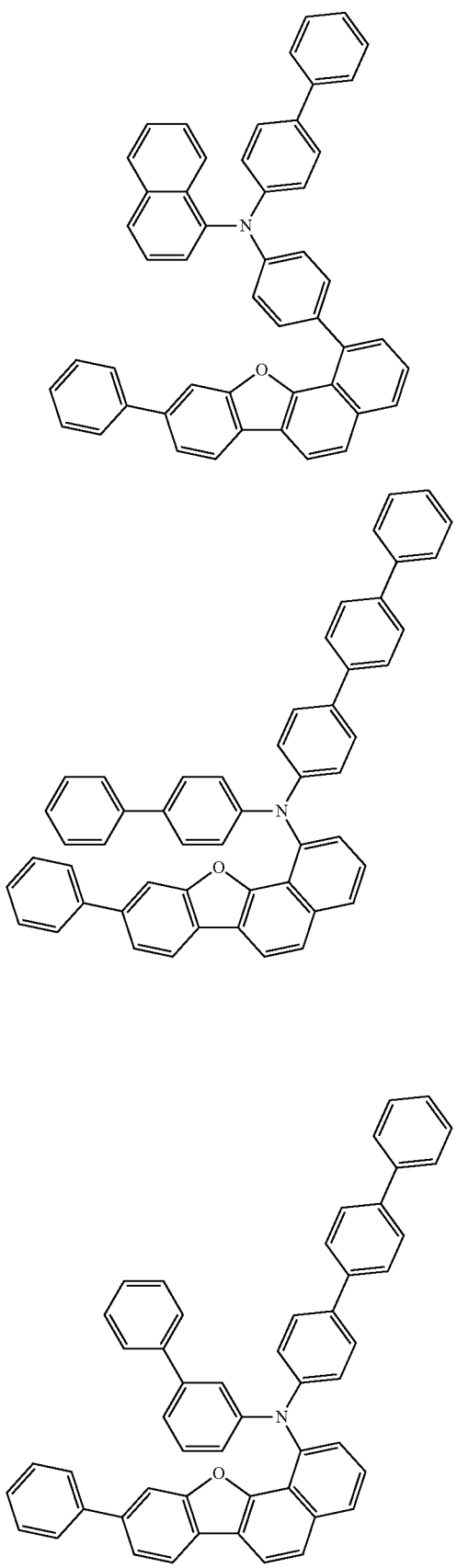
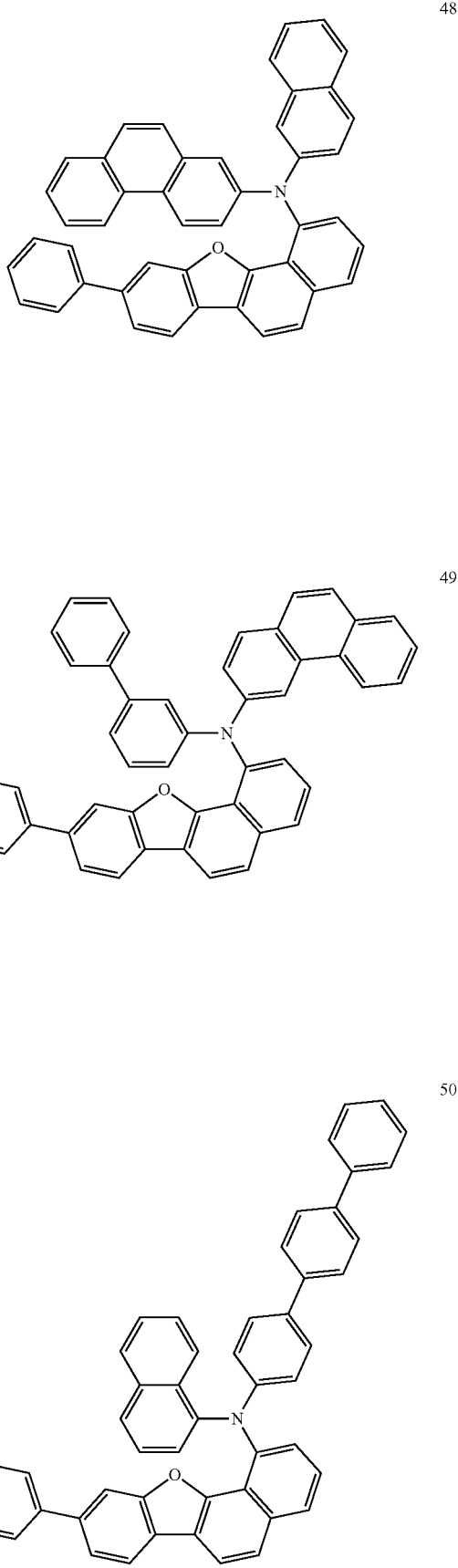

51
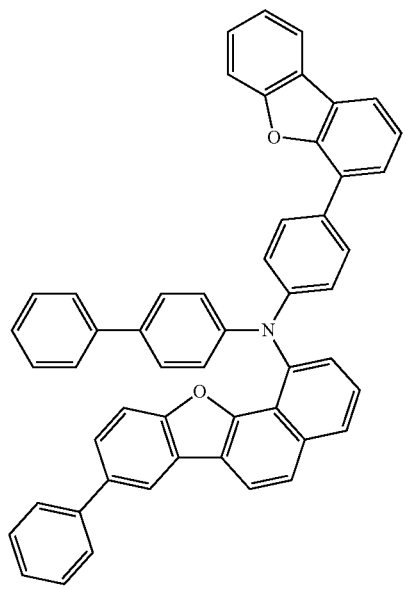
52
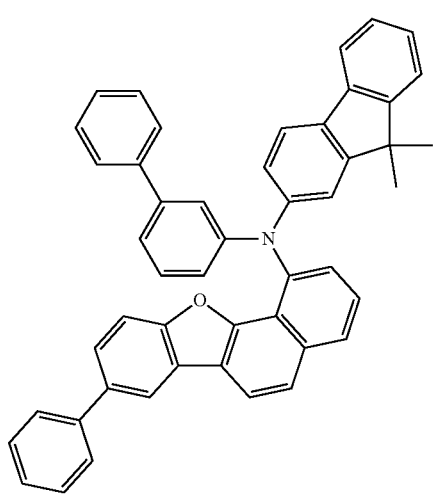
53
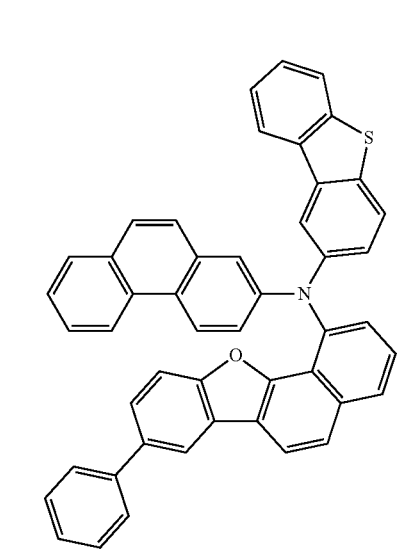
54
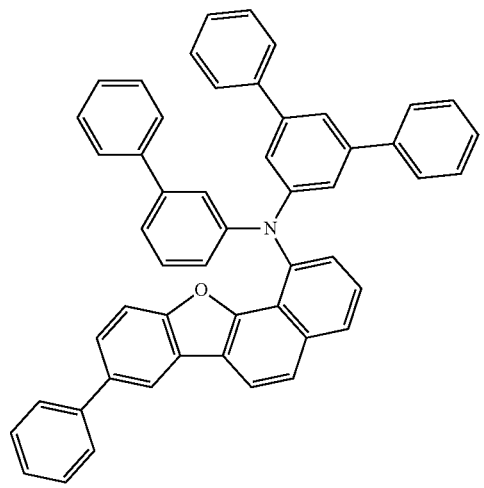
55
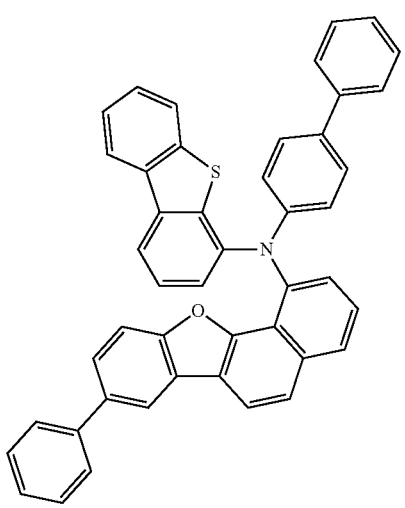
56
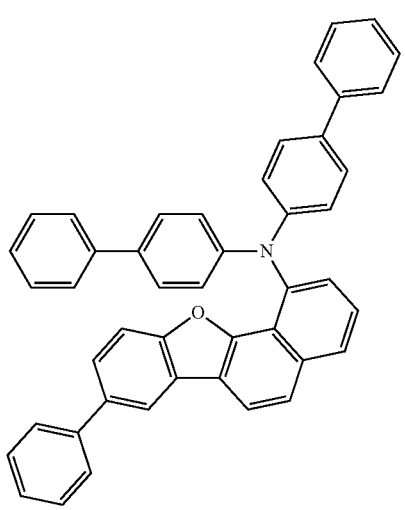

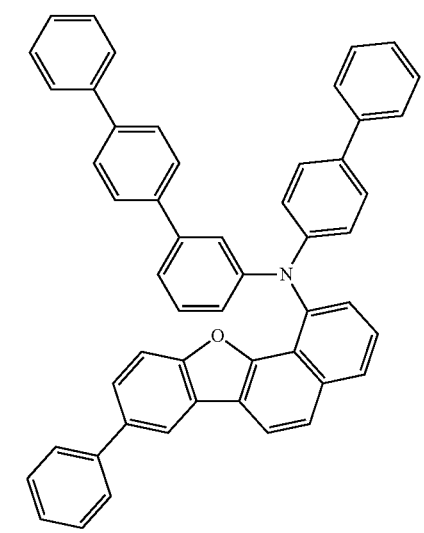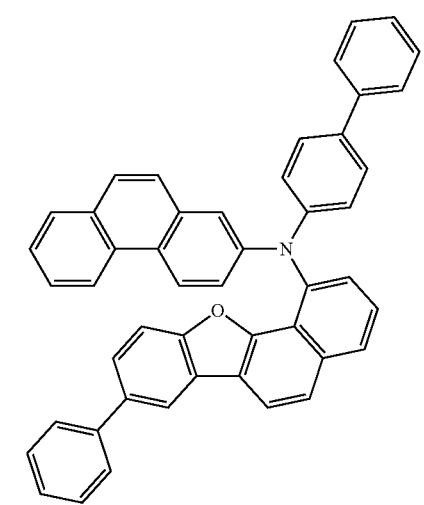

63
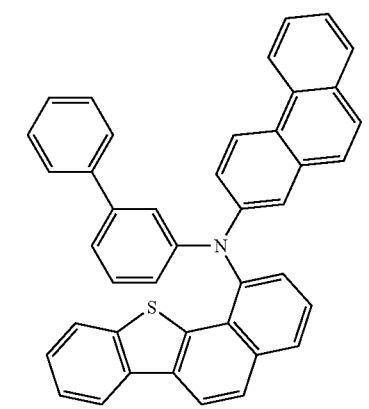
64
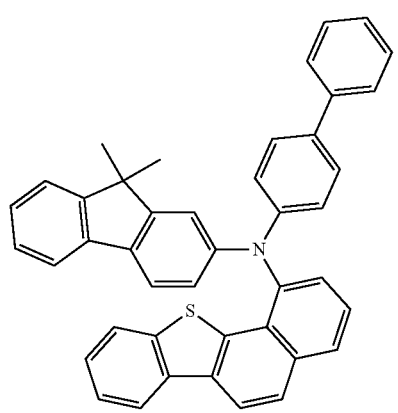
65
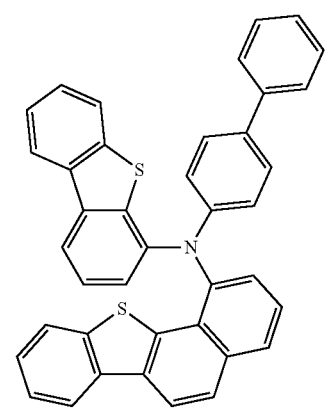
66
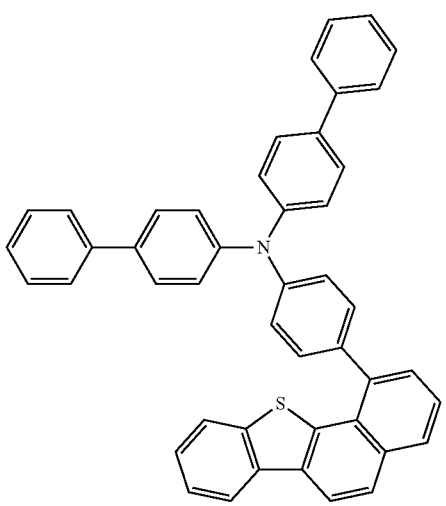
67
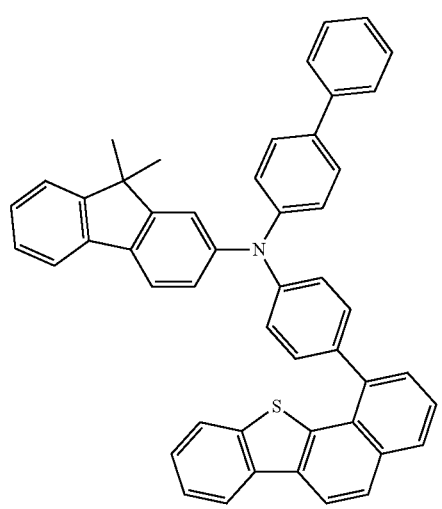
68
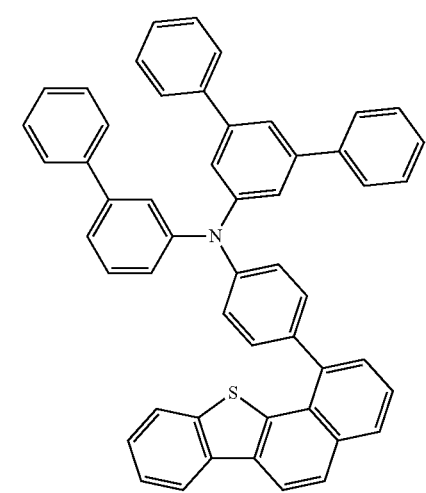

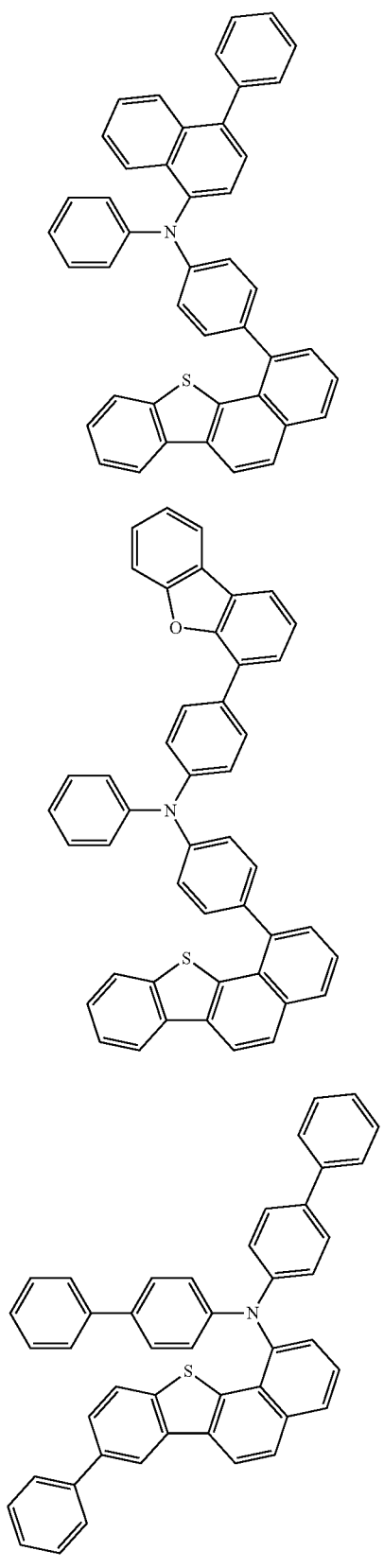
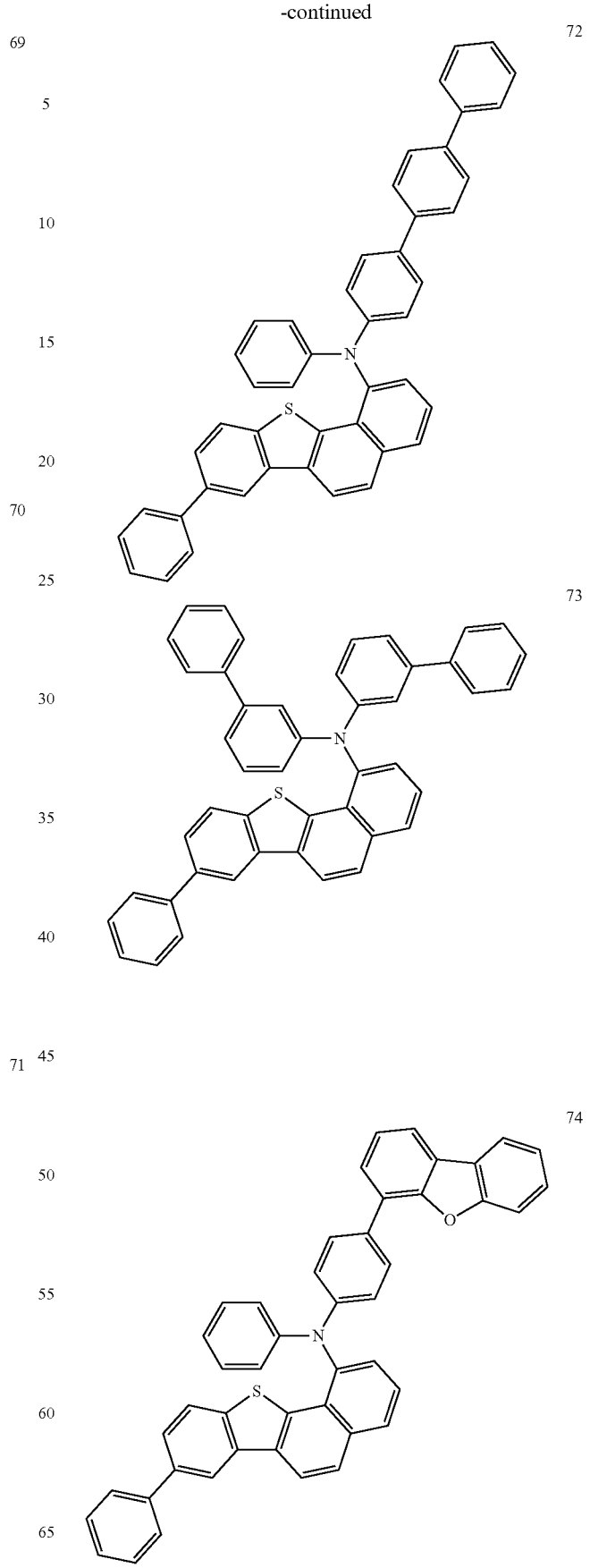

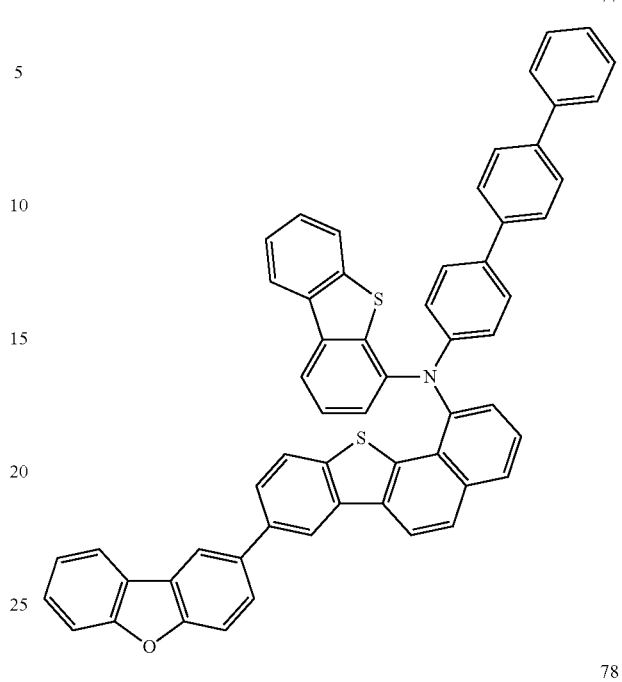
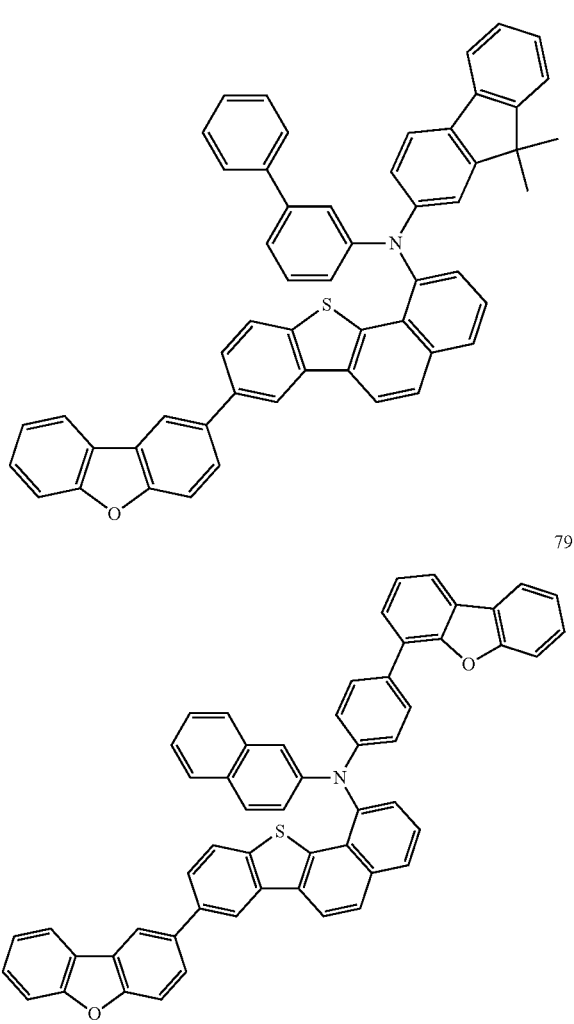

99
-continued
80
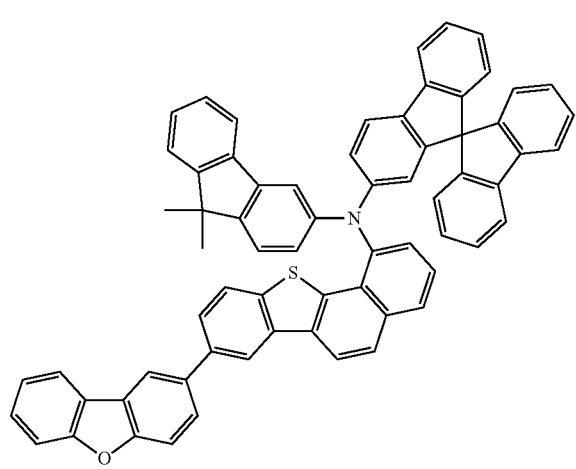
81
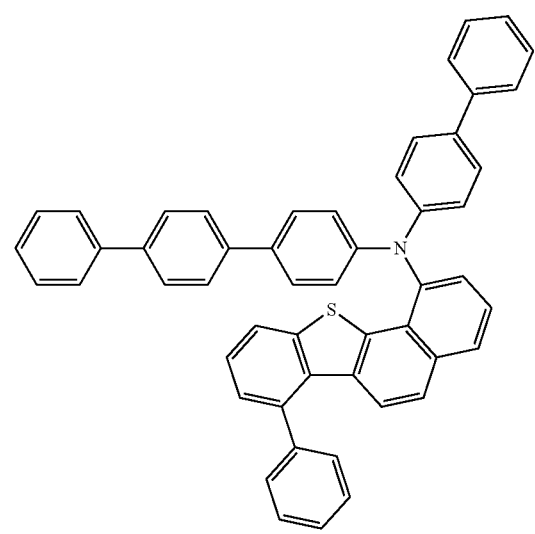
82
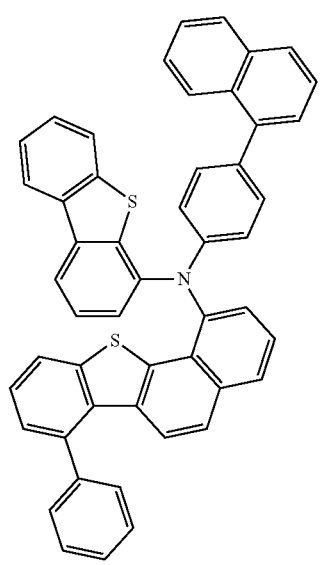
100
-continued
83
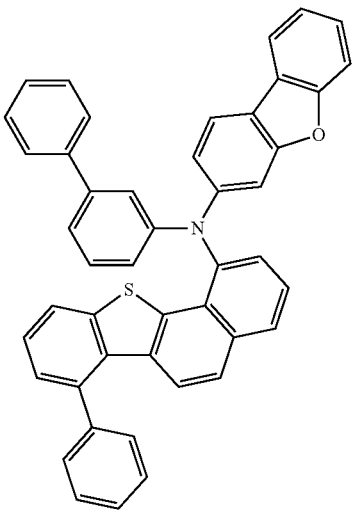
84
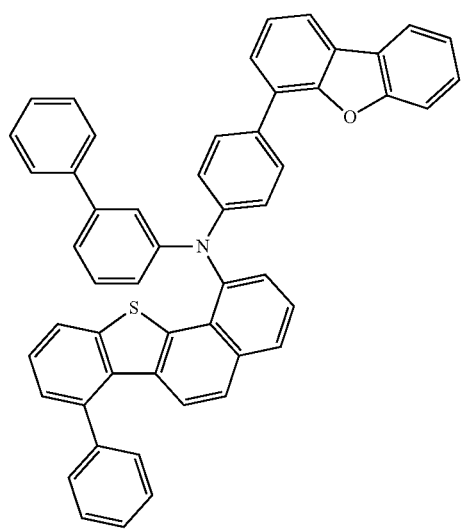
85
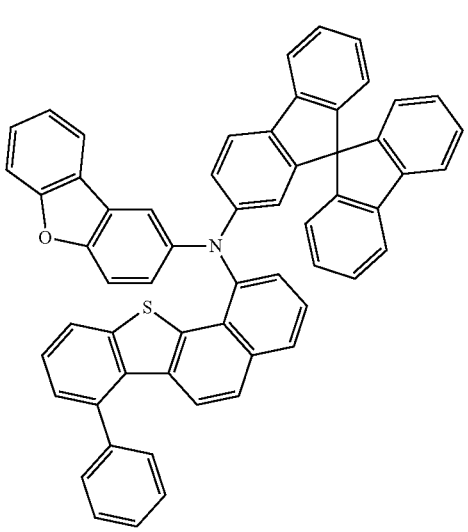

86
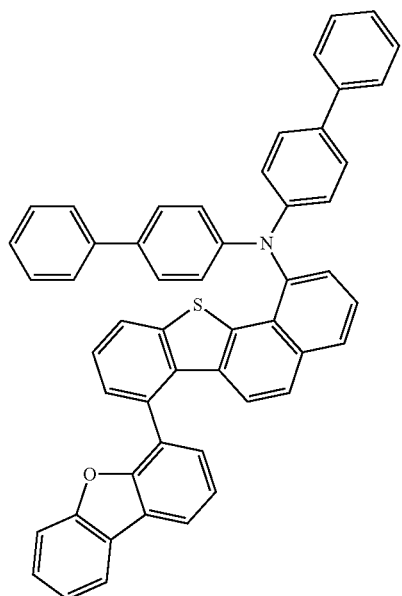
87
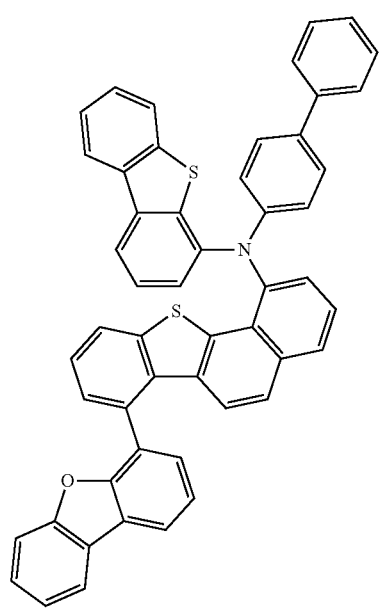
88
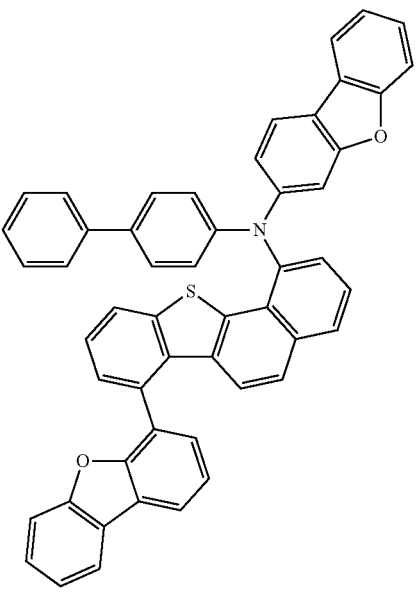
89
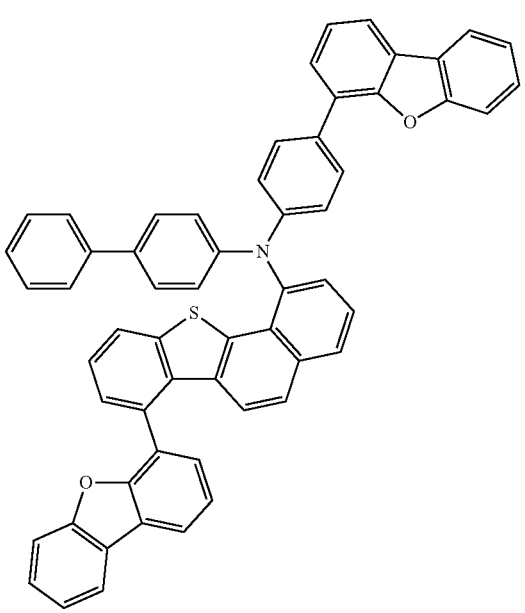

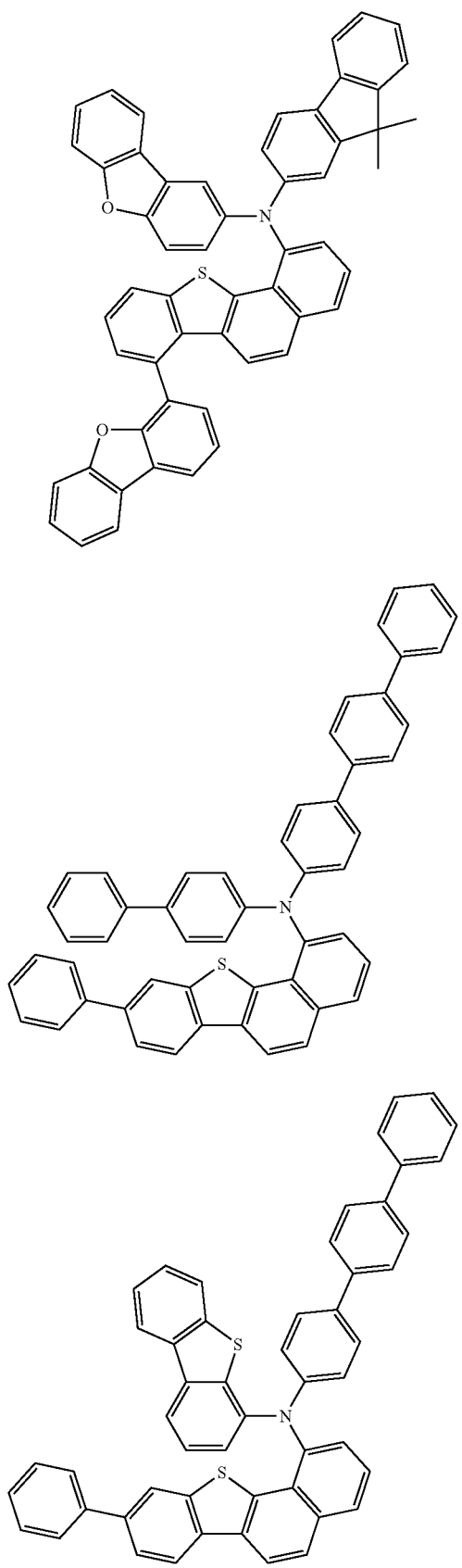
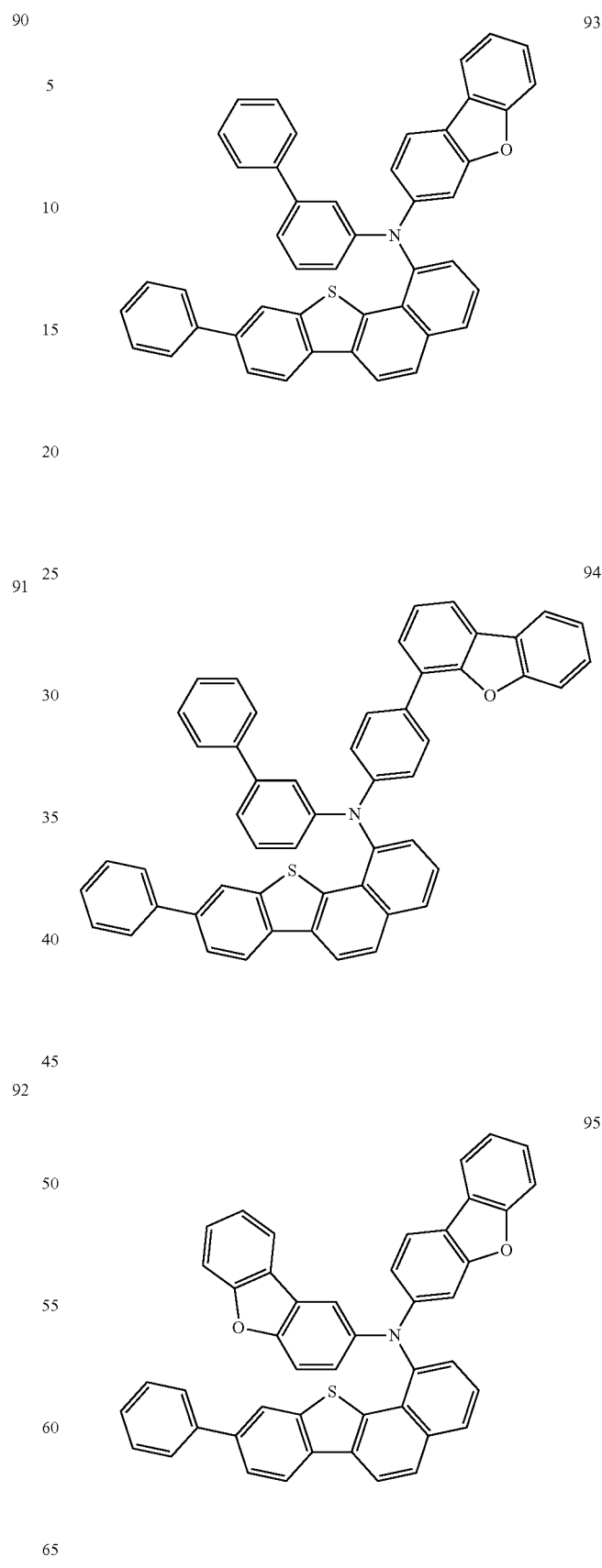

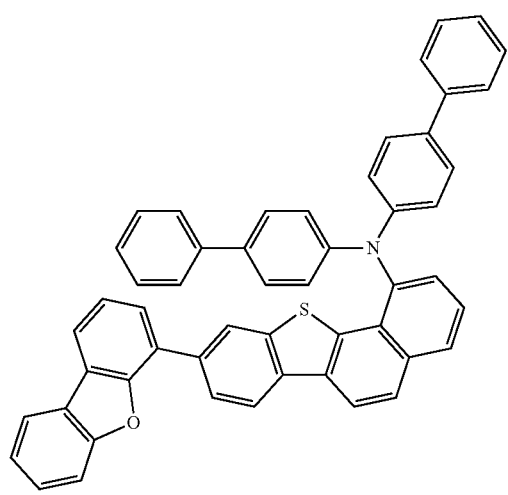

96

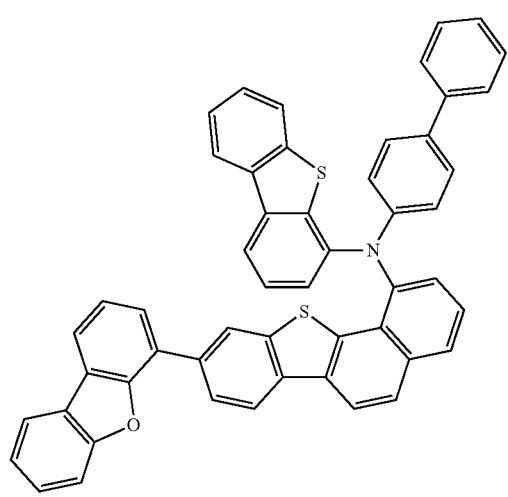

97

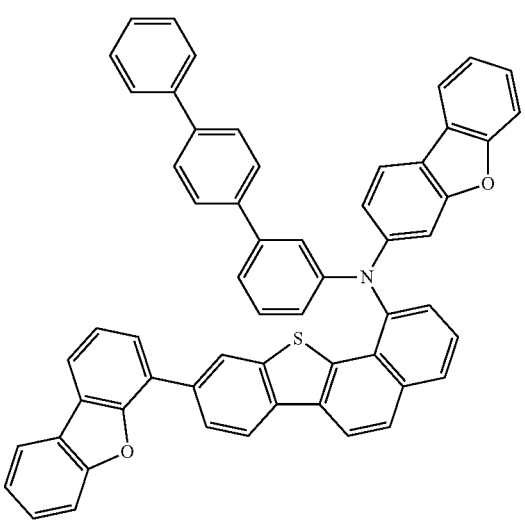

98

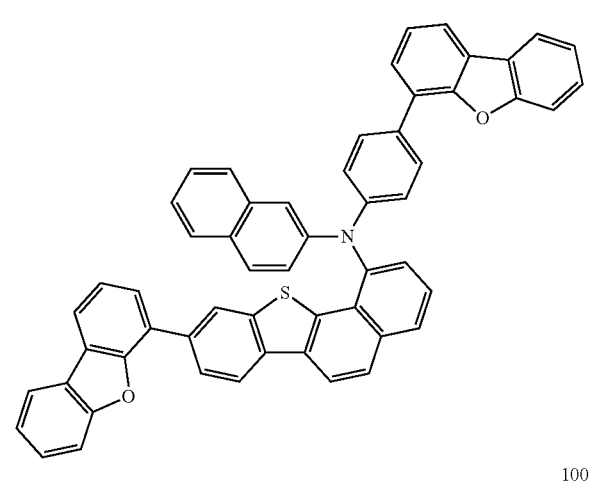

99

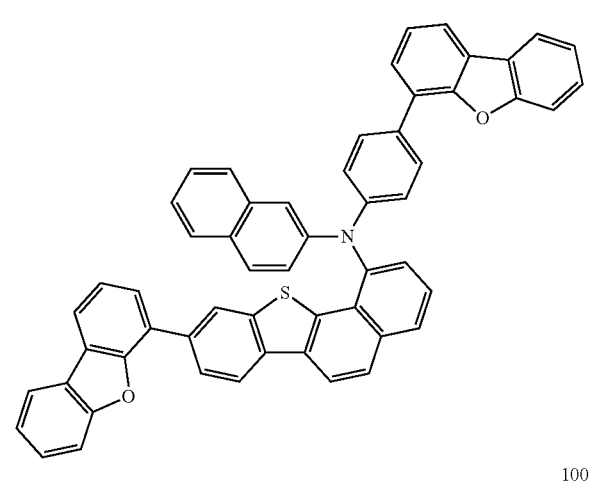

100

11. An organic light-emitting device comprising:
   a first electrode;
   a second electrode;
   at least one organic material layer between the first and second electrodes;
   a first protective film on the second electrode;
   a second protective film on the first protective film; and
   an encapsulation film on the second protective film,
wherein:
   the encapsulation film is bonded to the second protective film via an adhesive film; and
   the organic material layer comprises a compound represented by the following Chemical Formula 1:

[Chemical Formula 1]

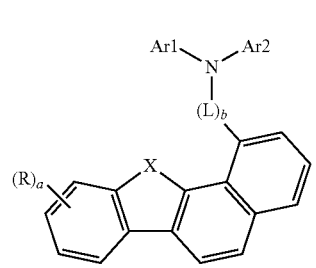

wherein:

X is O or S,

R represents one selected from the group consisting of an aryl group having 6 to 30 carbon atoms, an amino group, a heterocyclic group having 3 to 30 carbon atoms and including at least one hetero atom selected from the group consisting of O, N and S, an alkyl group having 1 to 30 carbon atoms, an alkenyl group having 2 to 30 carbon atoms, an alkynyl group having 2 to 30 carbon atoms, an alkoxy group having 1 to 30 carbon atoms, and an aryloxy group having 6 to 30 carbon atoms, a is an integer from 0 to 4, provided when a is 2 or greater, each R is the same as or different from each other, or adjacent R groups are bonded to each other to form a ring, L represents a direct bond or represents one selected from the group consisting of substituted or unsubstituted arylene having 6 to 30 carbon atoms and substituted or unsubstituted heteroarylene having 3 to 30 carbon atoms, b is an integer from 0 to 4, and each of Ar1 and Ar2 independently represents one selected from the group consisting of a substituted or unsubstituted C6 to C60 aryl group, a C3 to C30 heteroaryl group containing at least one heteroatom selected from the group consisting of O, N and S, an alkyl group having 1 to 30 carbon atoms, an alkenyl group having 2 to 30 carbon atoms, an alkynyl group having 2 to 30 carbon atoms, an alkoxyl group having 1 to 30 carbon atoms, and an aryloxy group having from 6 to 30 carbon atoms.

12. The organic light-emitting device of claim 11, wherein the at least one organic material layer comprises at least two compounds represented by Chemical Formula 1.

13. The organic light-emitting device of claim 11, wherein the at least one organic material layer comprises at least one layer selected from the group consisting of a hole injection layer, a hole transport layer, an auxiliary hole transport layer, a light-emitting layer, an auxiliary electron transport layer, an electron transport layer, and an electron injection layer.

14. The organic light-emitting device of claim 11, wherein the first protective film is on entire faces of the at least one organic material layer and the second electrode.

15. The organic light-emitting device of claim 11, further comprising a driving thin-film transistor including an active layer electrically connected to the first electrode.

16. The organic light-emitting device of claim 15, wherein the active layer comprises an oxide semiconductor layer.

17. The organic light-emitting device of claim 15, wherein the driving thin-film transistor further comprises a gate insulating film on the active layer, and a gate electrode on the gate insulating film.

18. The organic light-emitting device of claim 11, wherein each of R, L, Ar1 and Ar2 is independently free of carbazole.

19. The organic light-emitting device of claim 11, wherein each of Ar1 and Ar2 is independently selected from the following substituents:

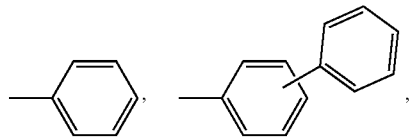

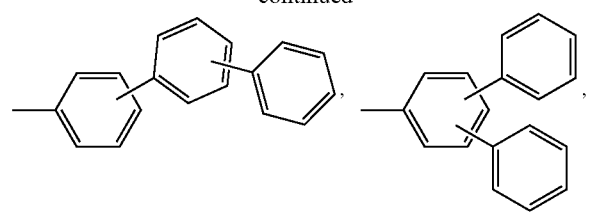

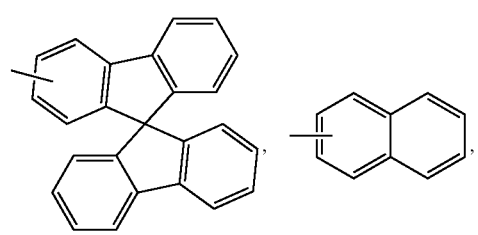

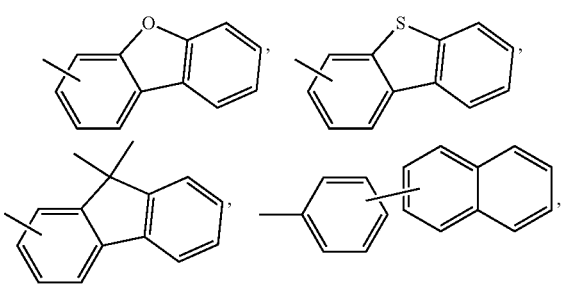

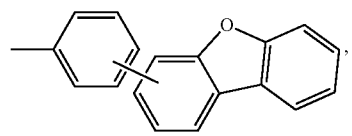

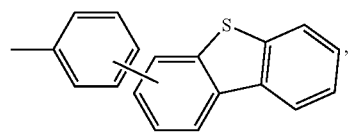

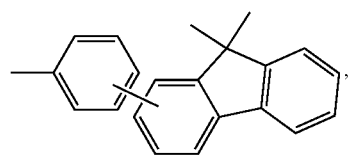

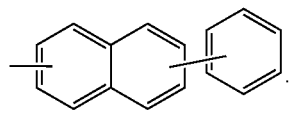

20. The organic light-emitting device of claim 11, wherein the compound is represented by one of the following compounds:

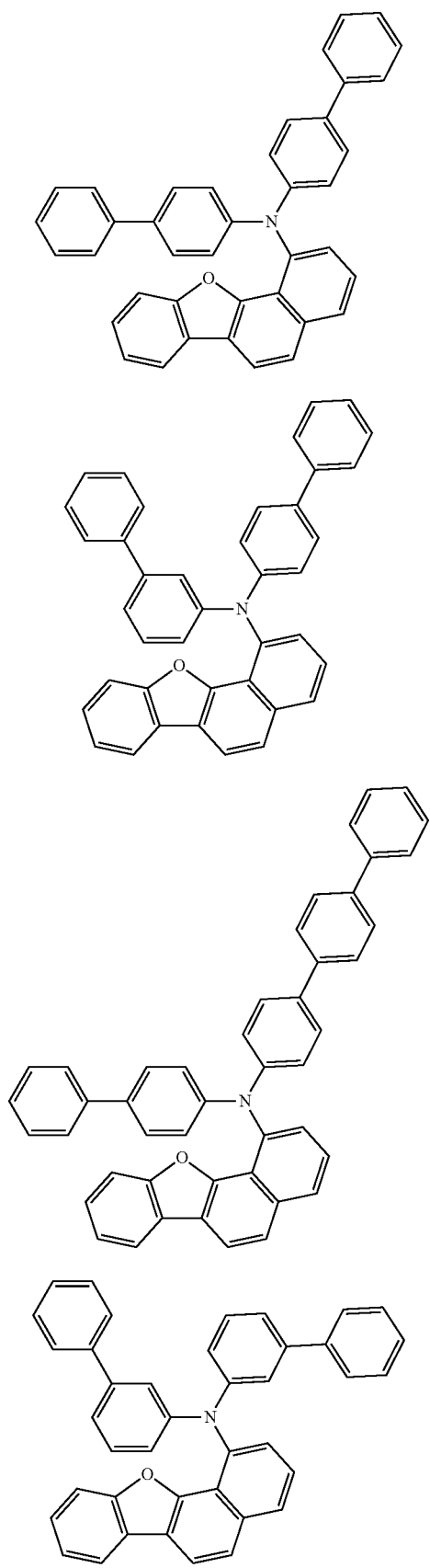
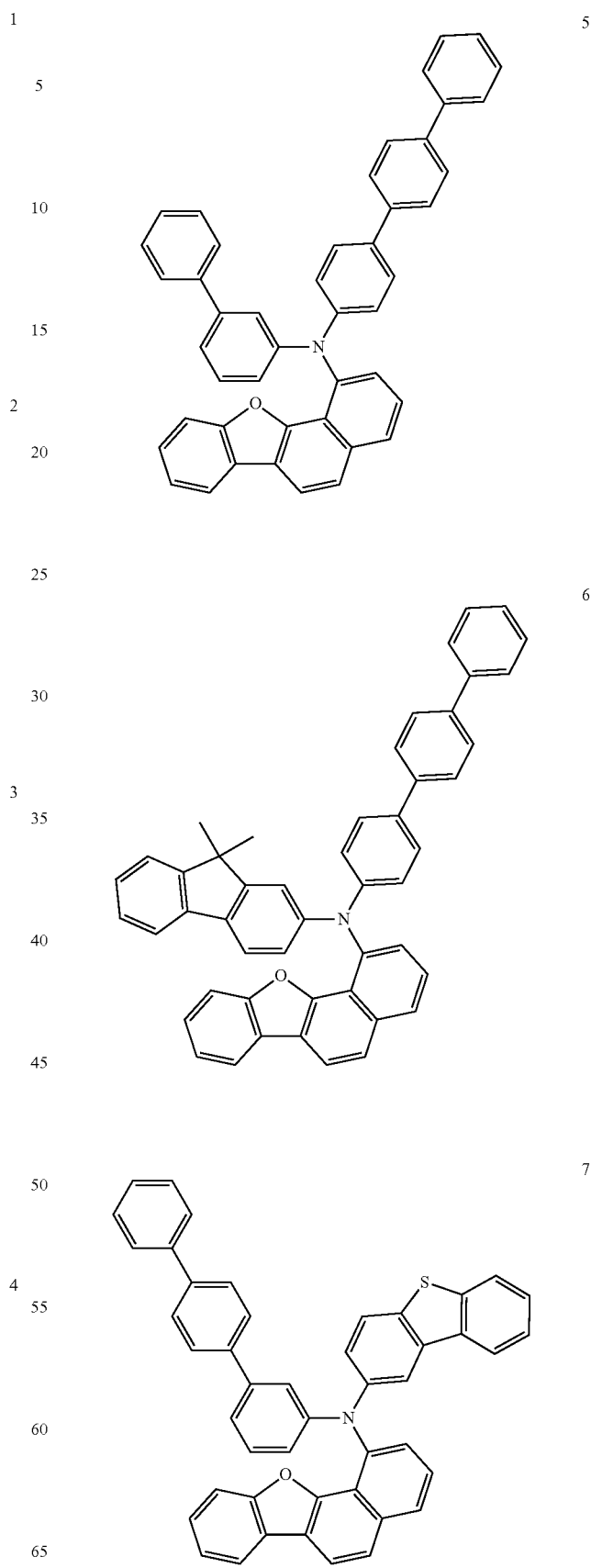

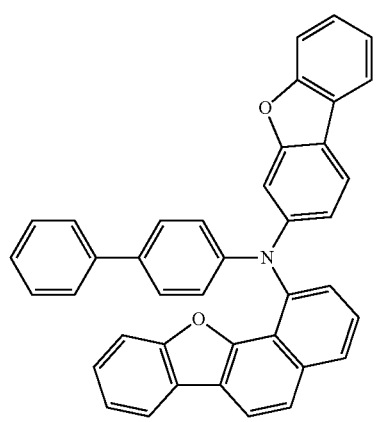
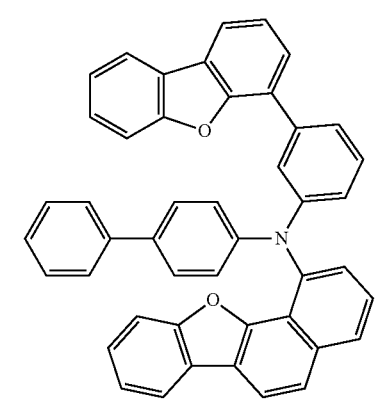
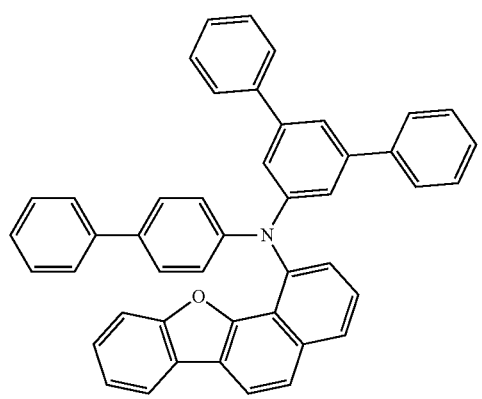
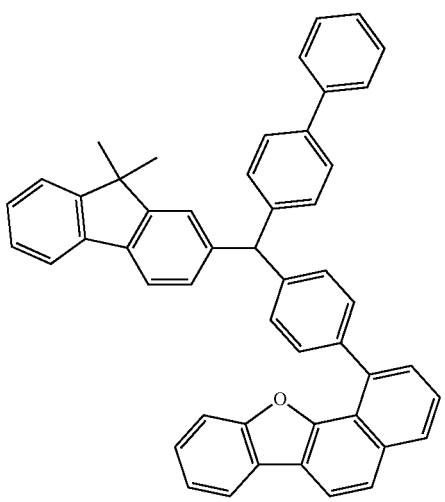
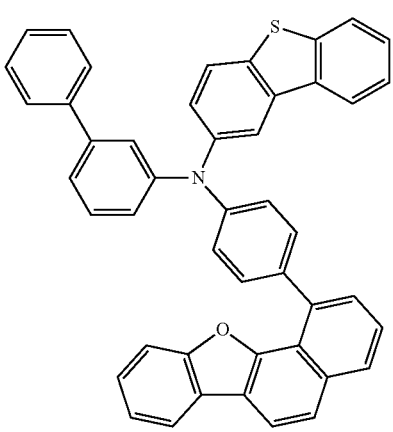
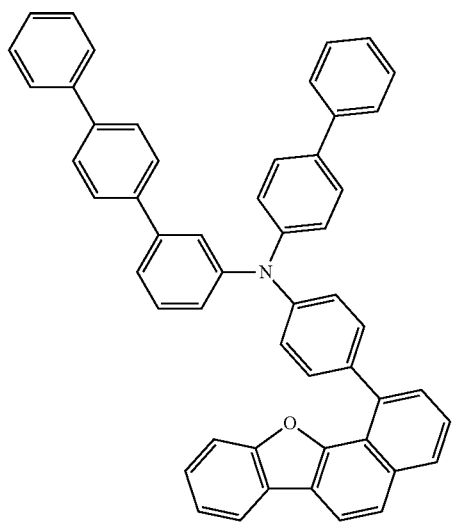

14
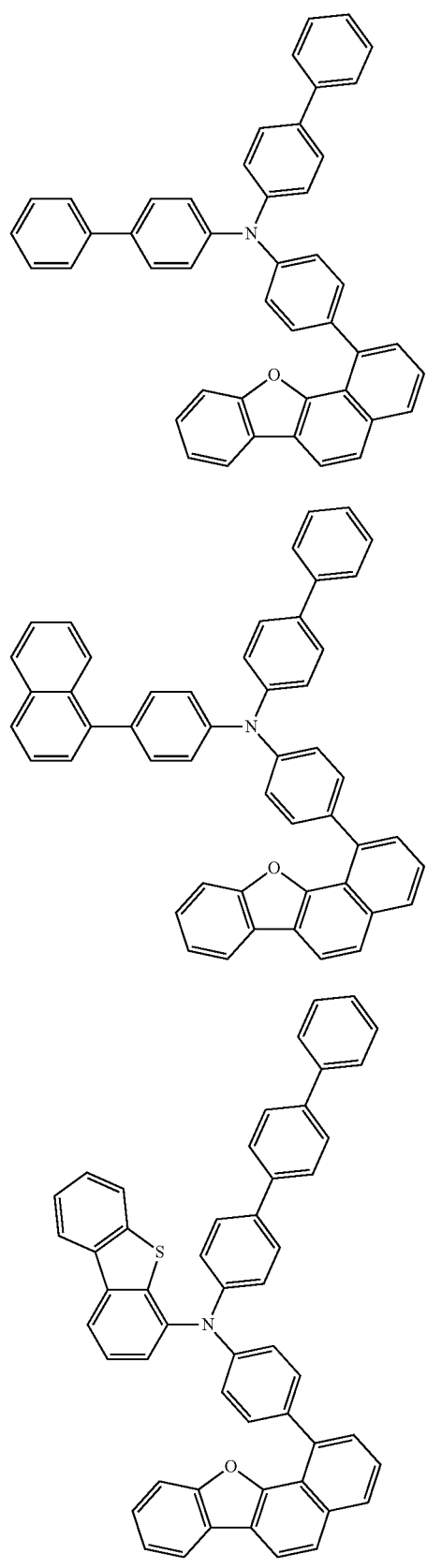
17
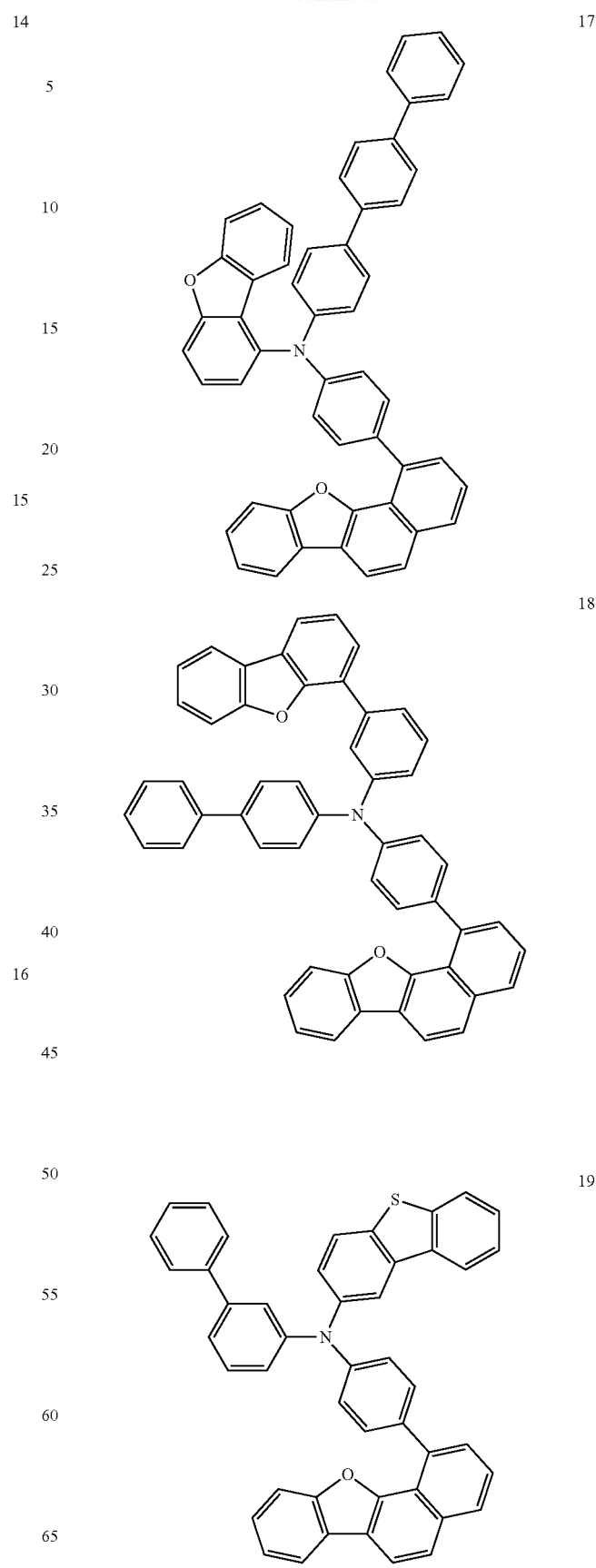

20
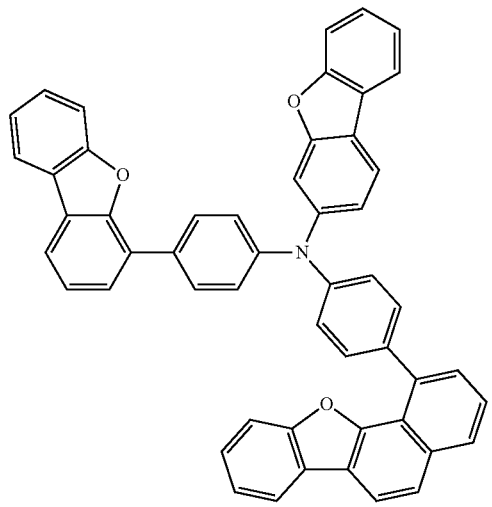
22
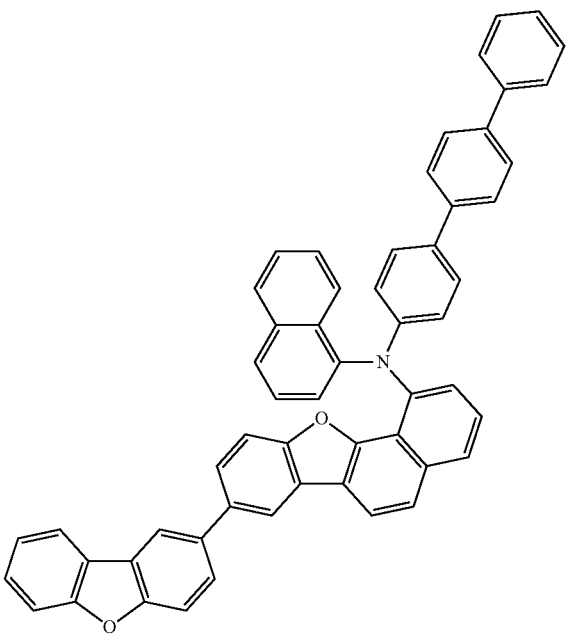
21
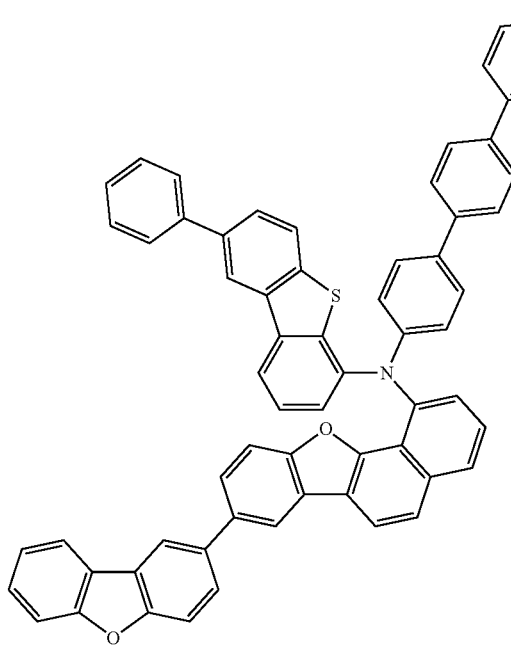
23
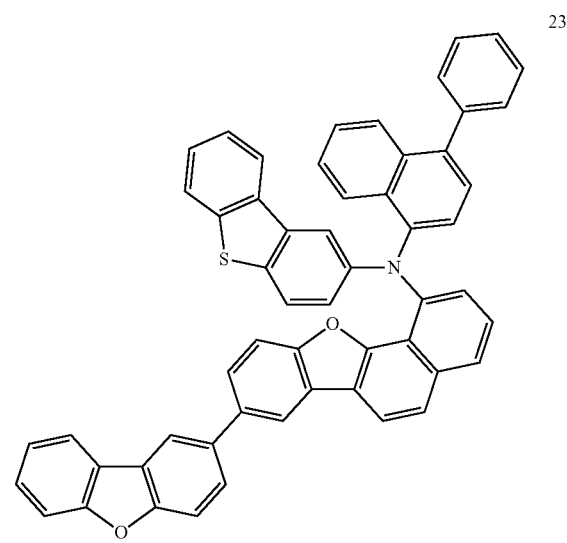

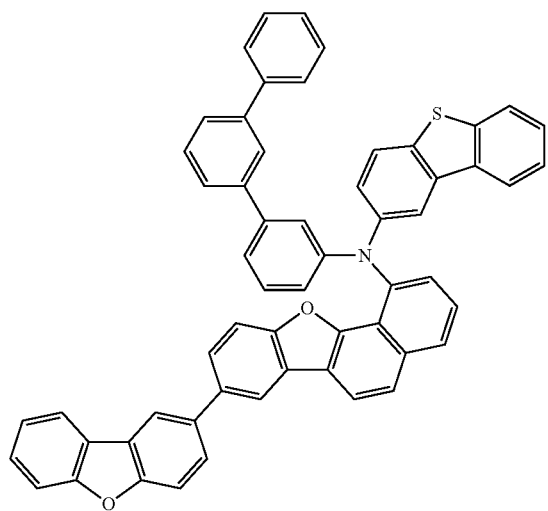
24
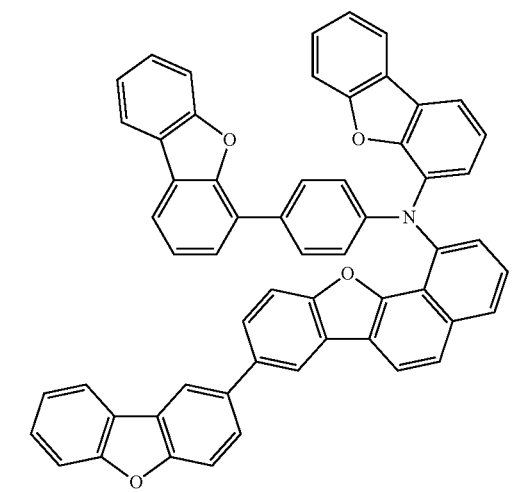
25
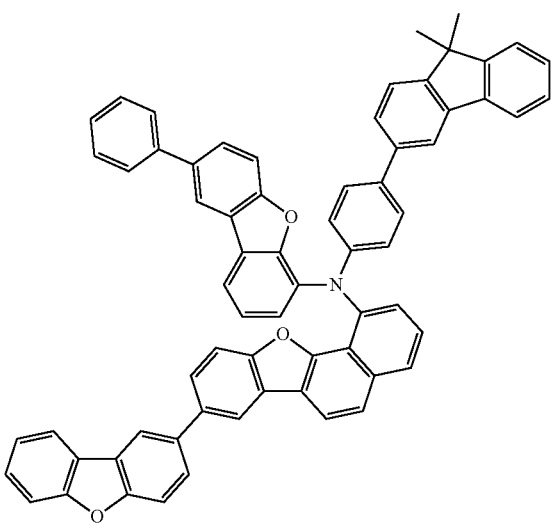
26
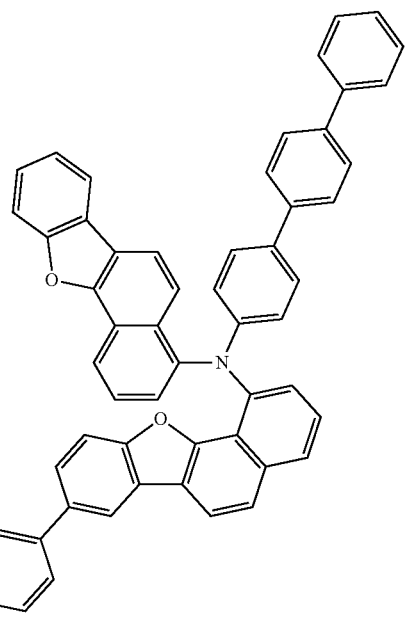
27
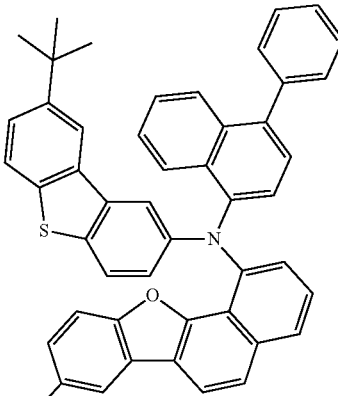
28
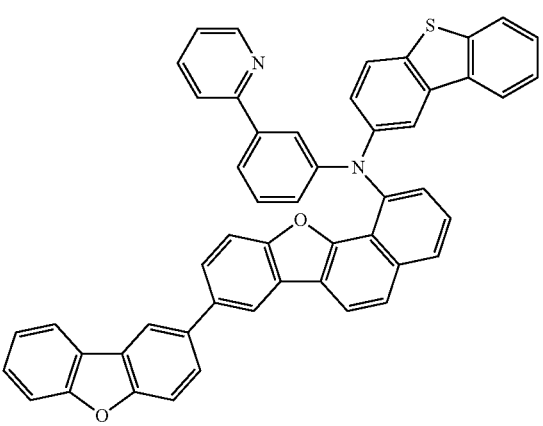
29

30
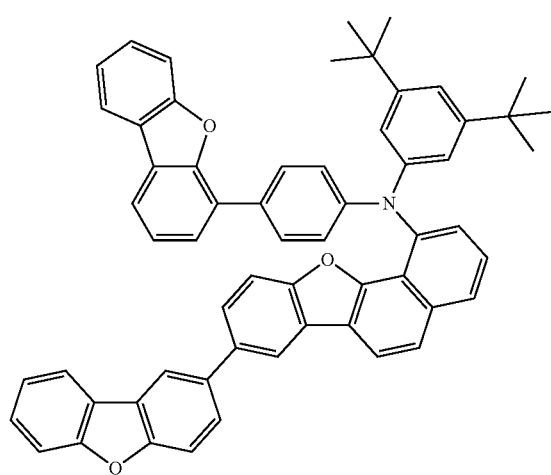
31
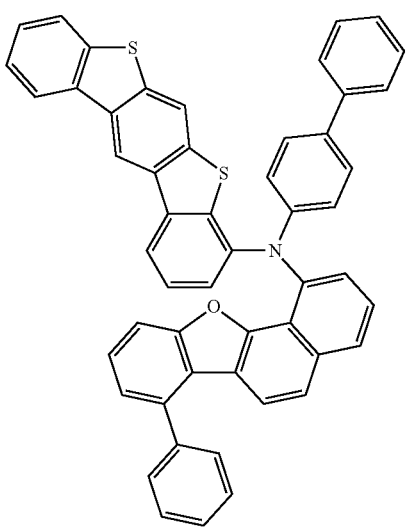
32
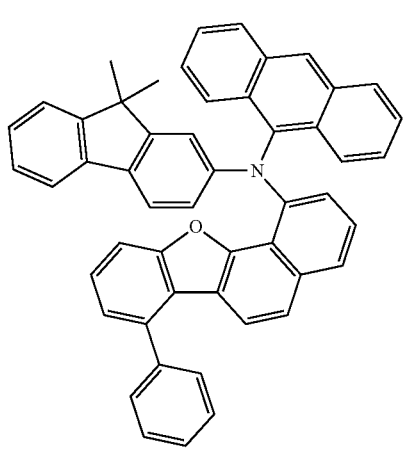
33
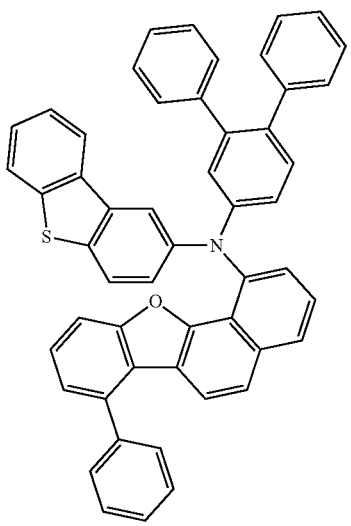
34
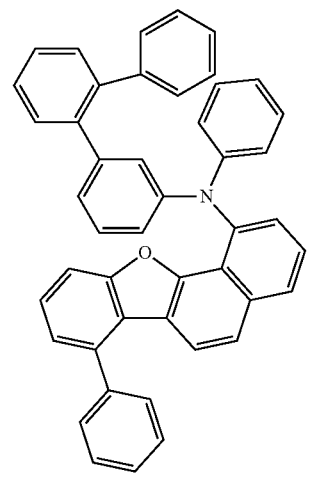
35
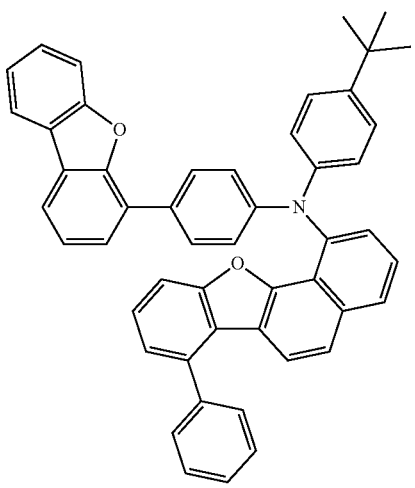

36
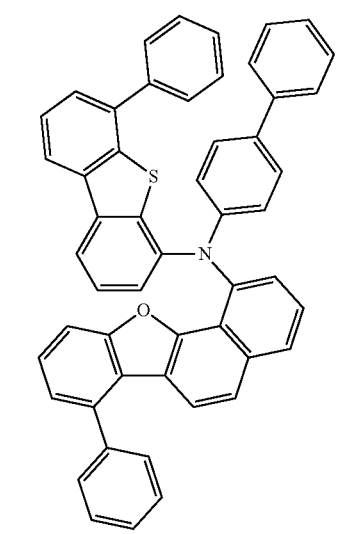
37
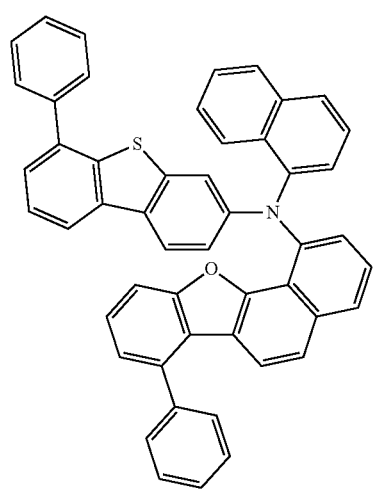
38
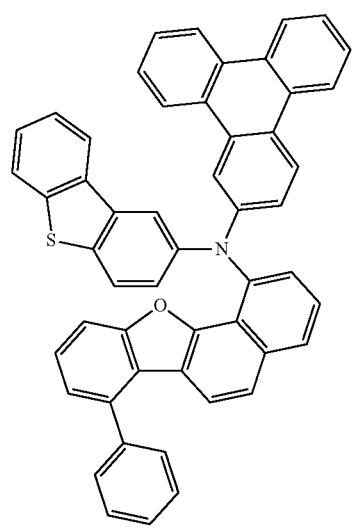
39
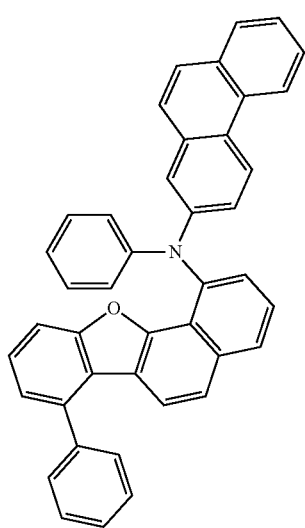
40
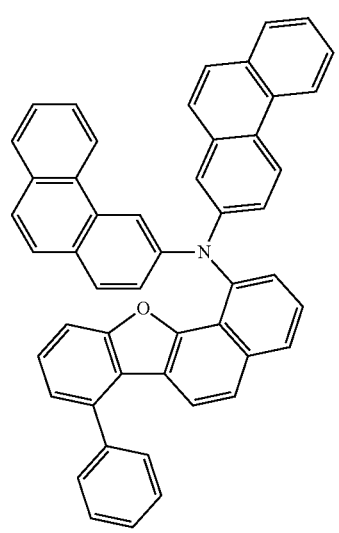
41
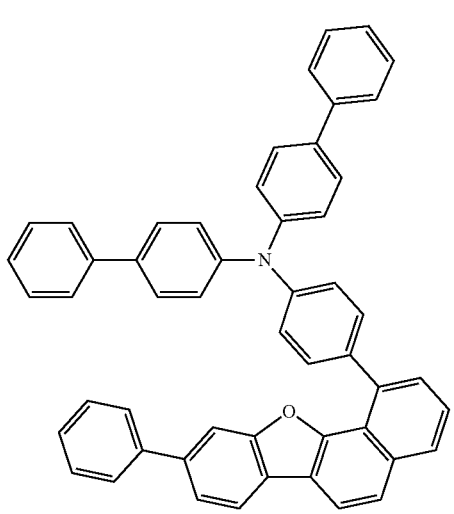

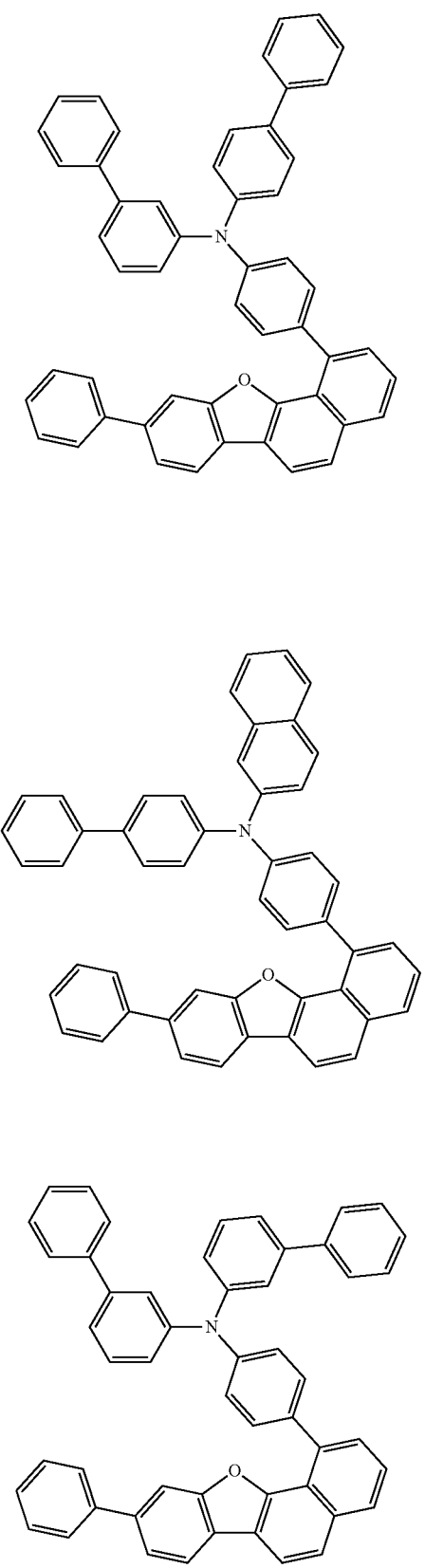
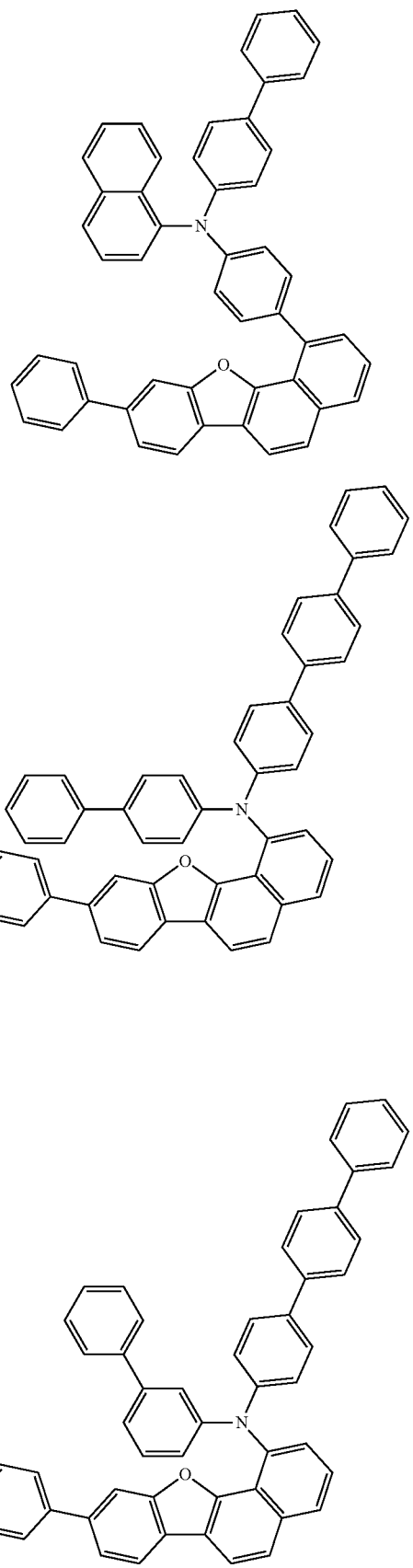

-continued
48
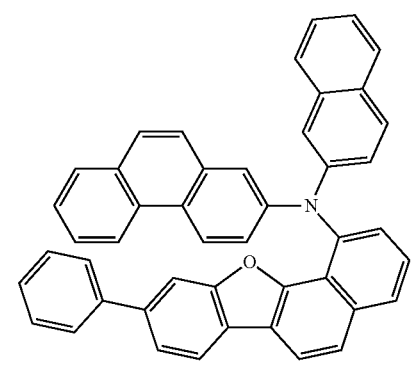
49
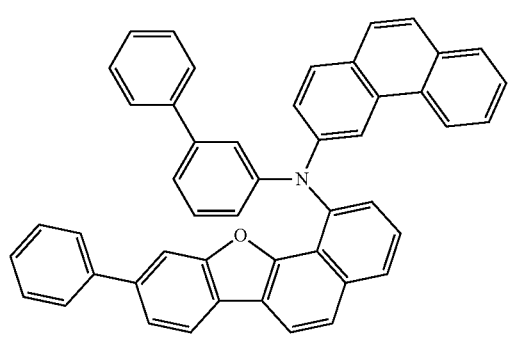
50
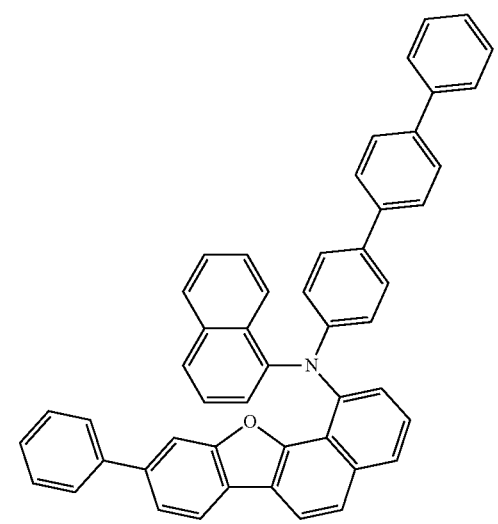
-continued
51
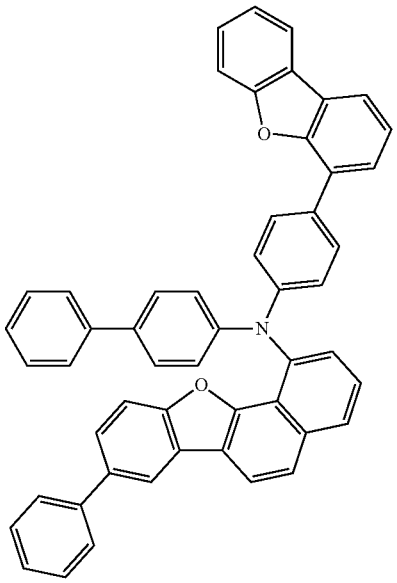
52
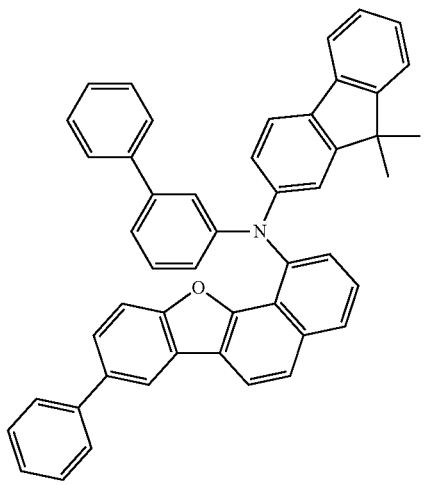
53
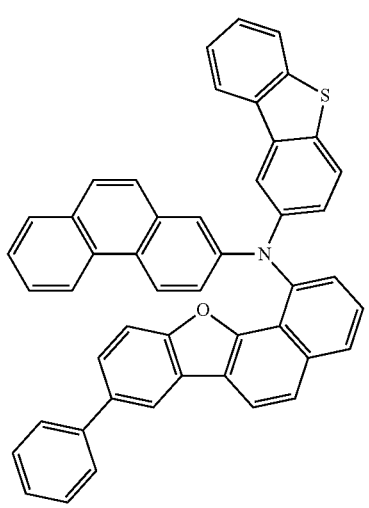

54
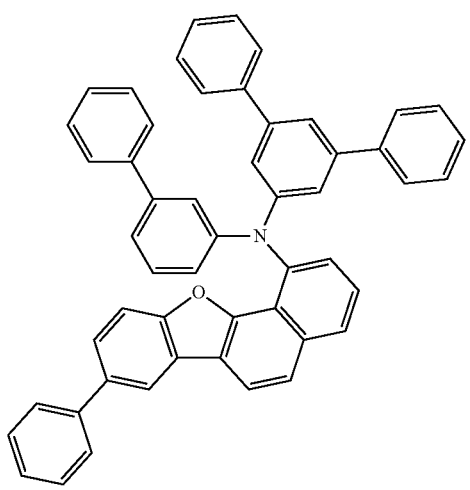
55
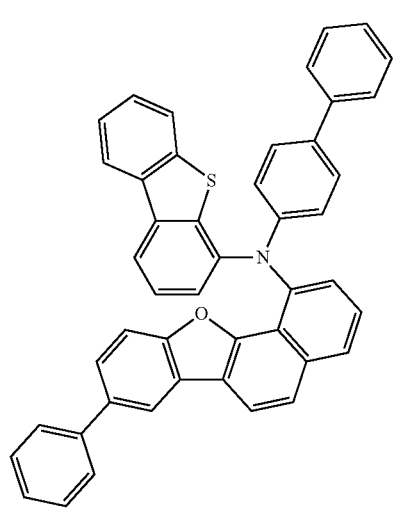
56
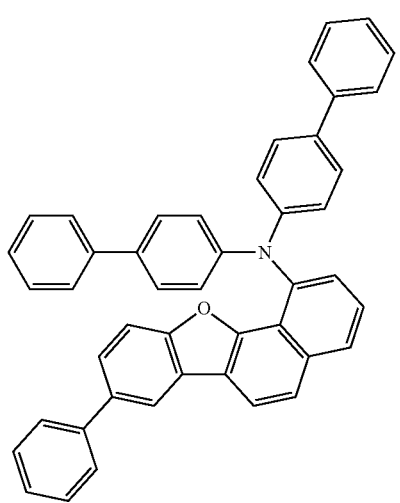
57
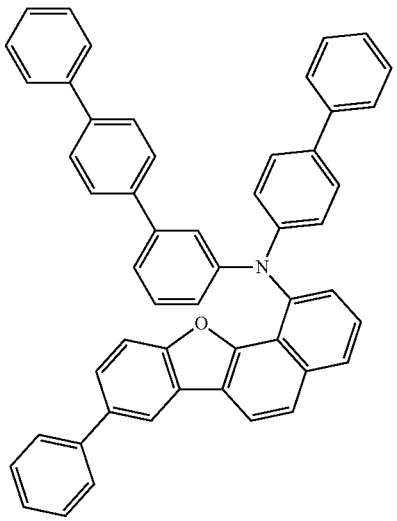
58
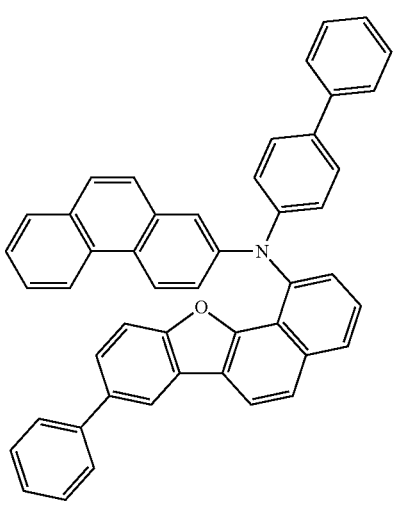
59
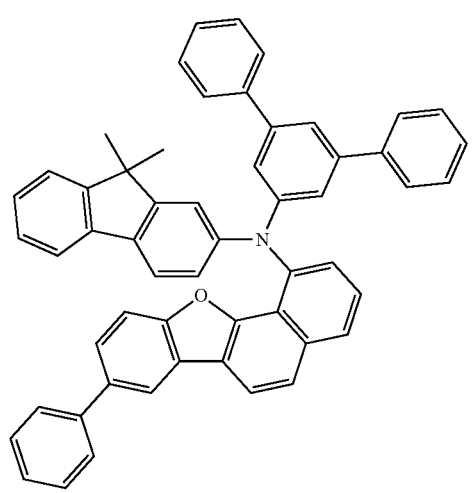

129
-continued
60
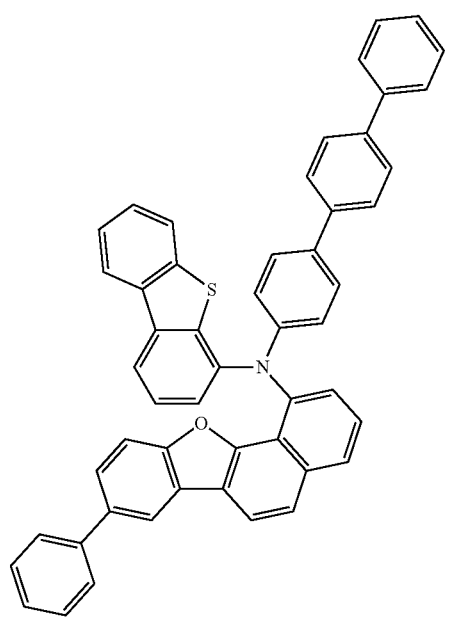
61
62
130
-continued
63
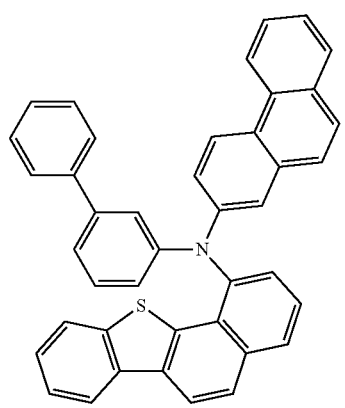
64
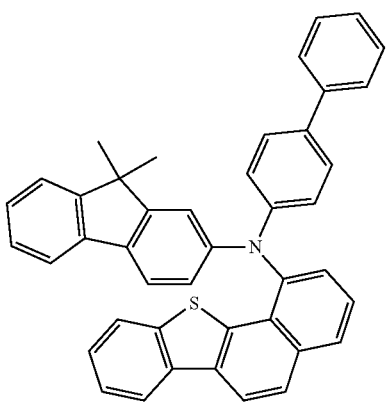
65
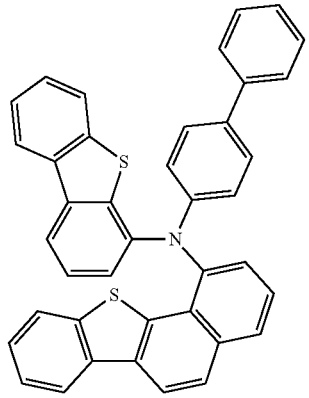
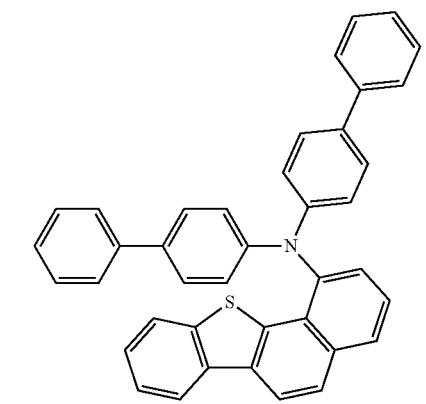

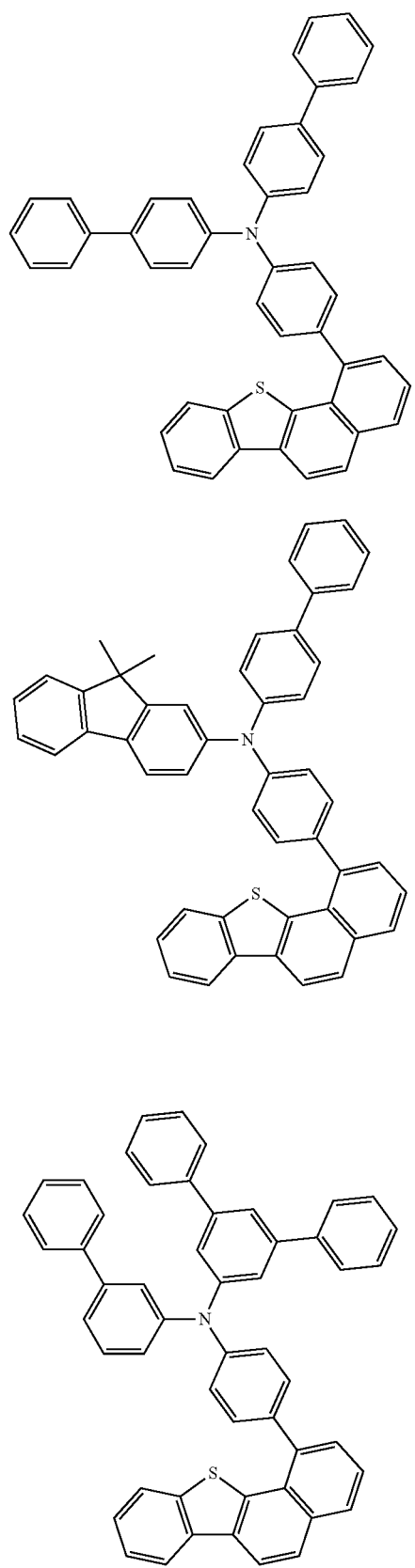
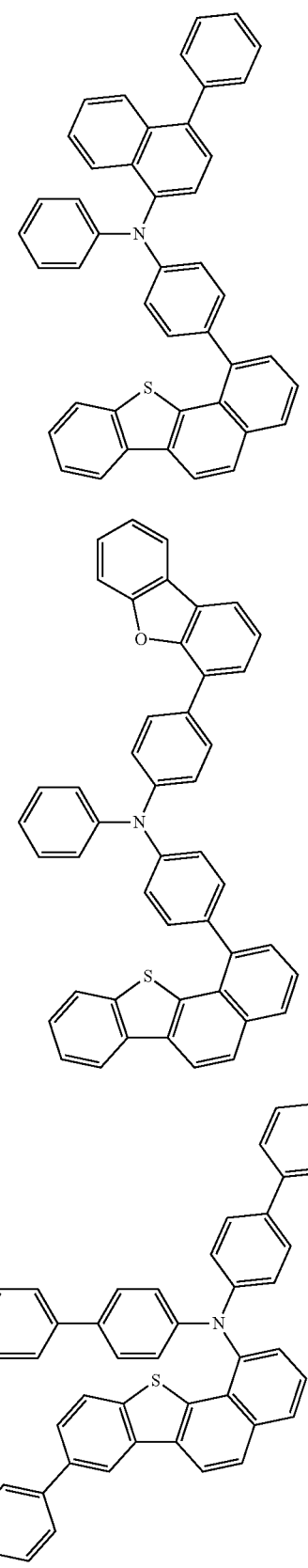

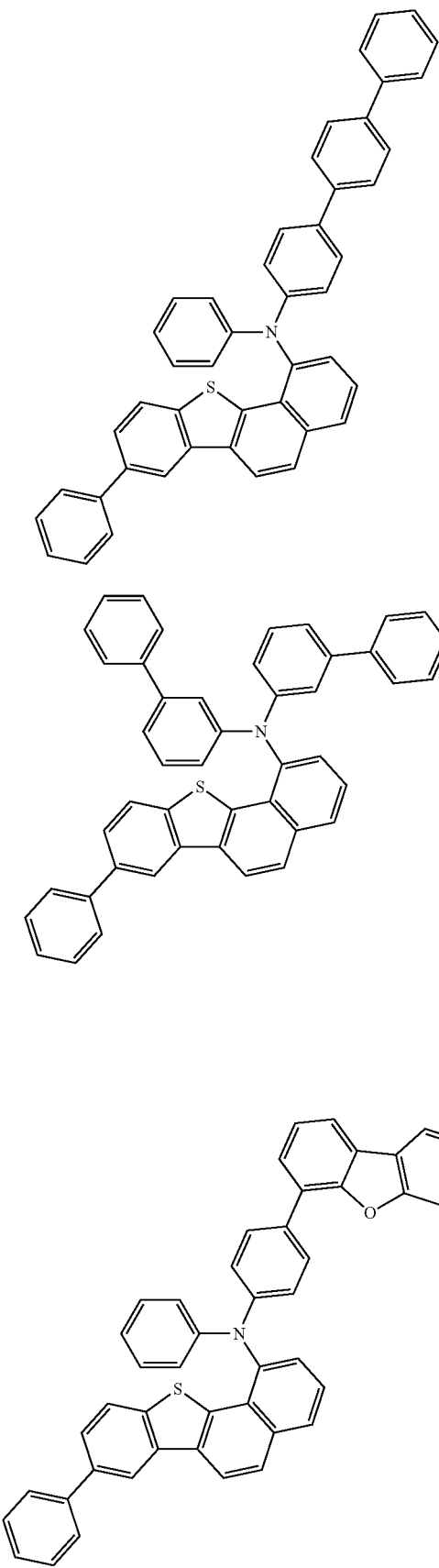

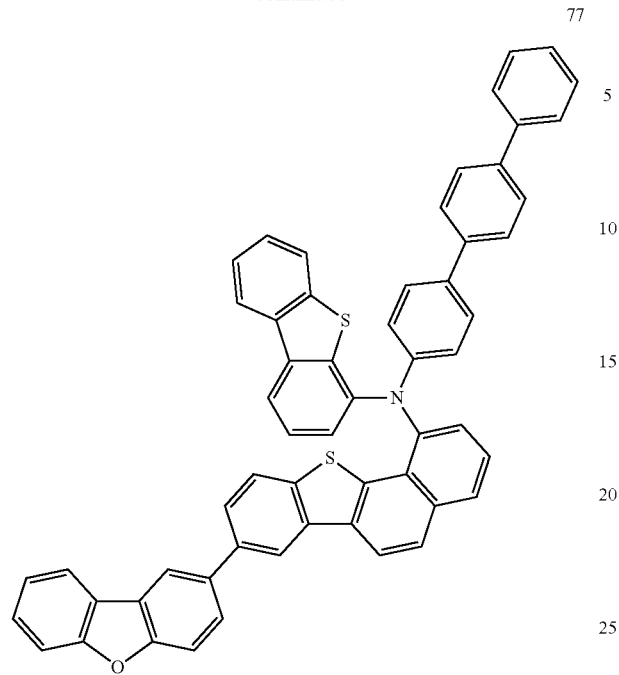
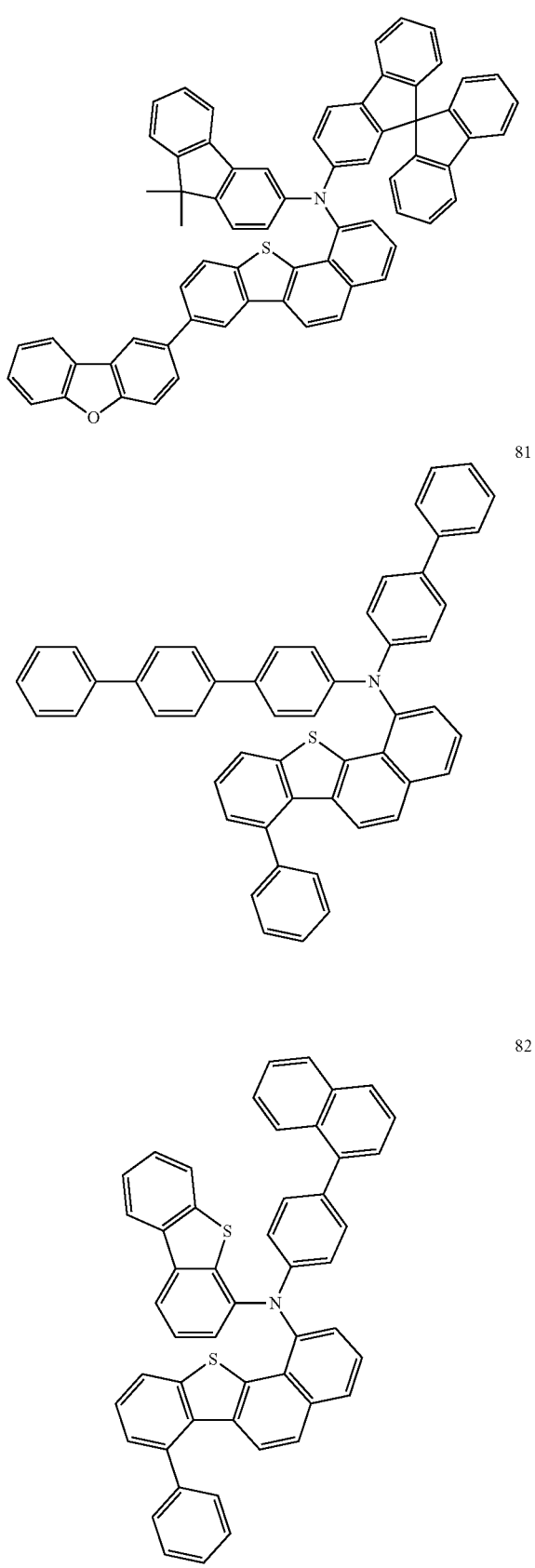

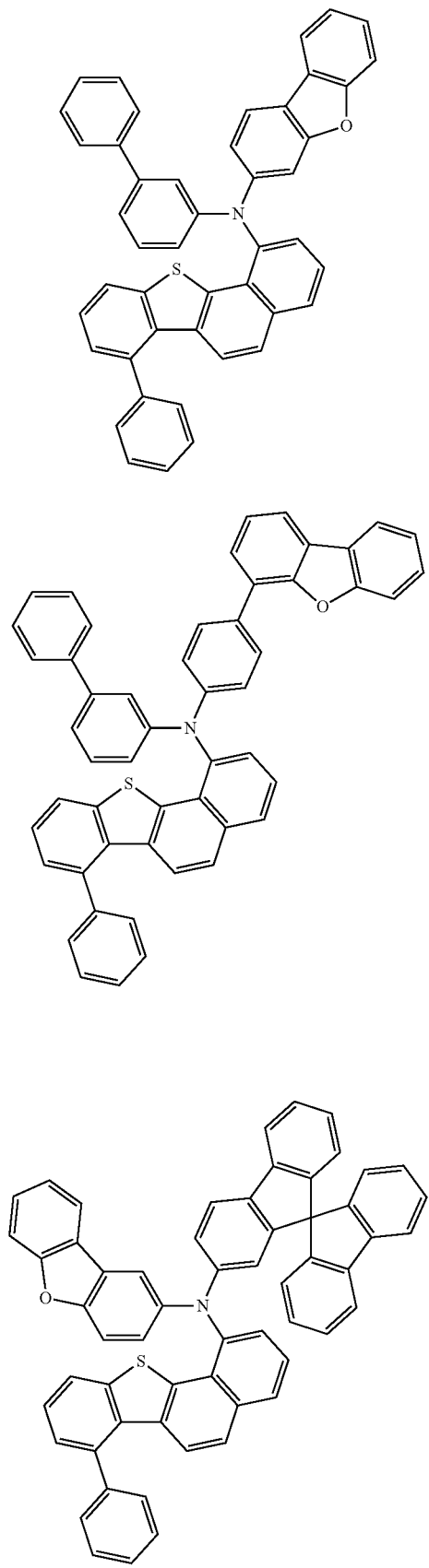

-continued
88
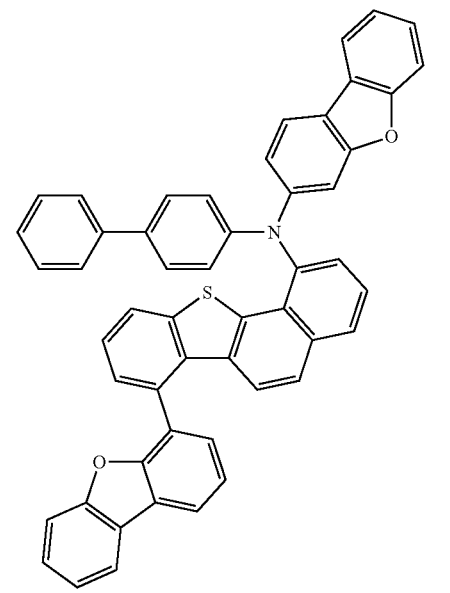
89
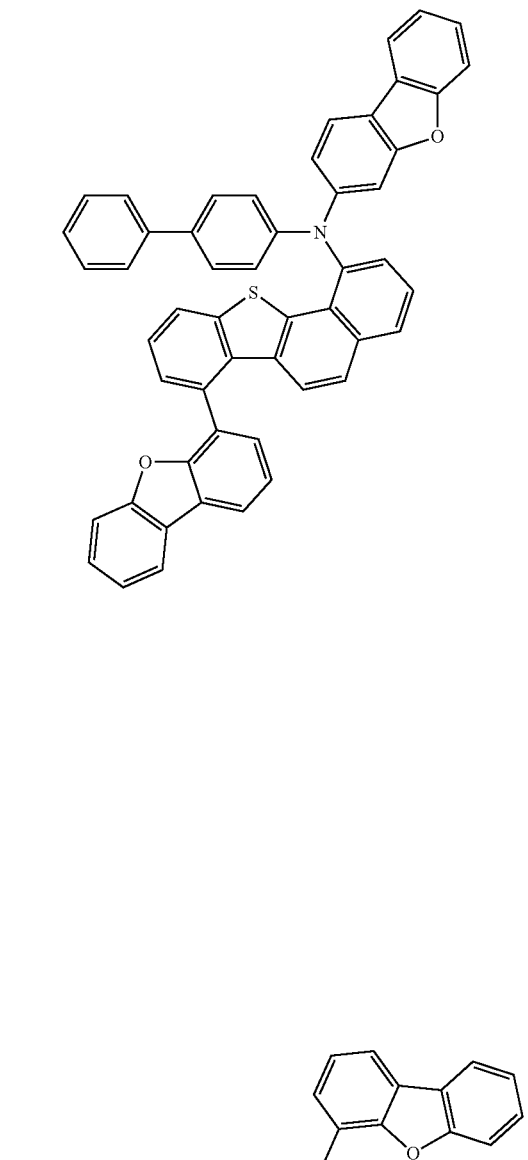
-continued
90
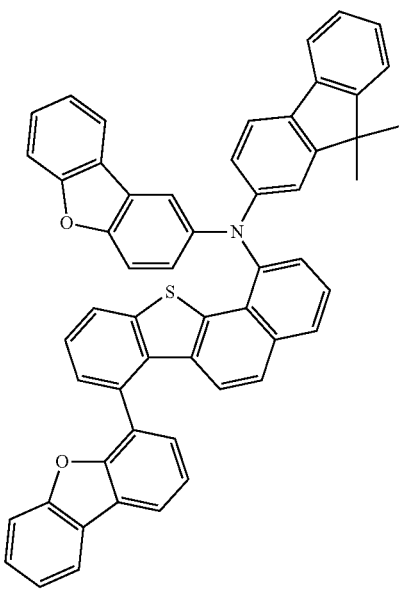
91
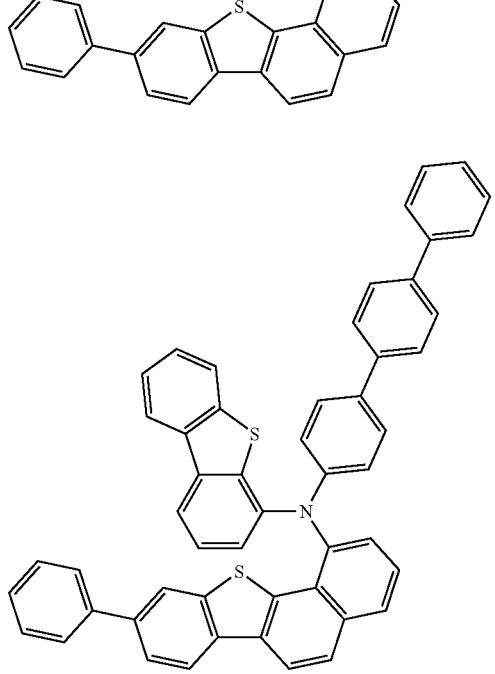
92

93
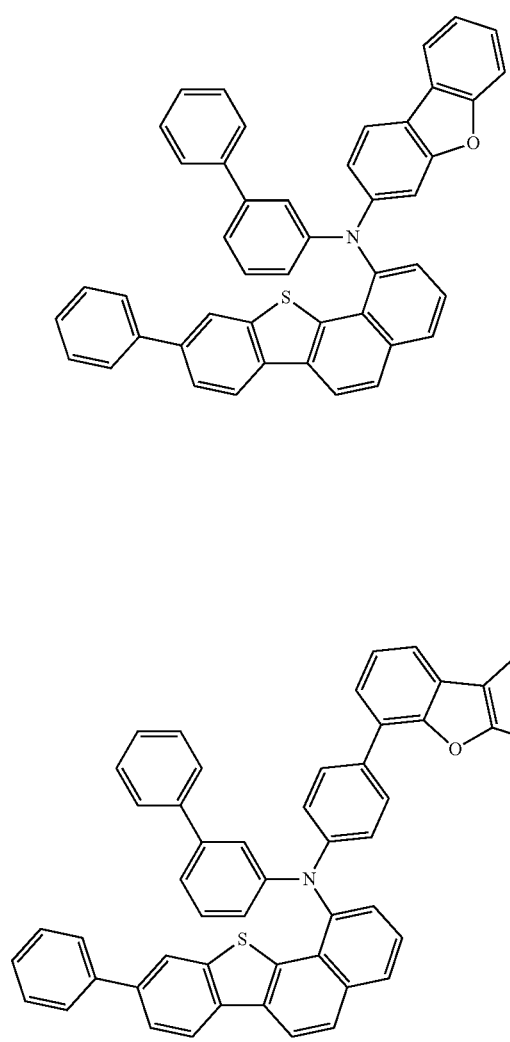
94
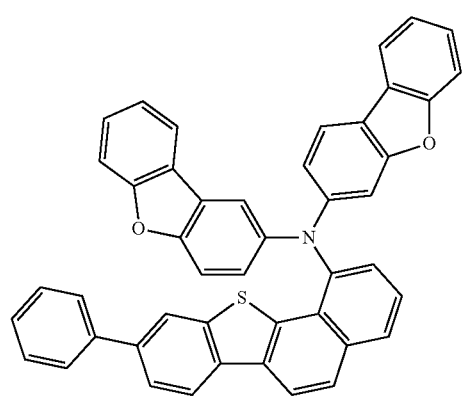
95
96
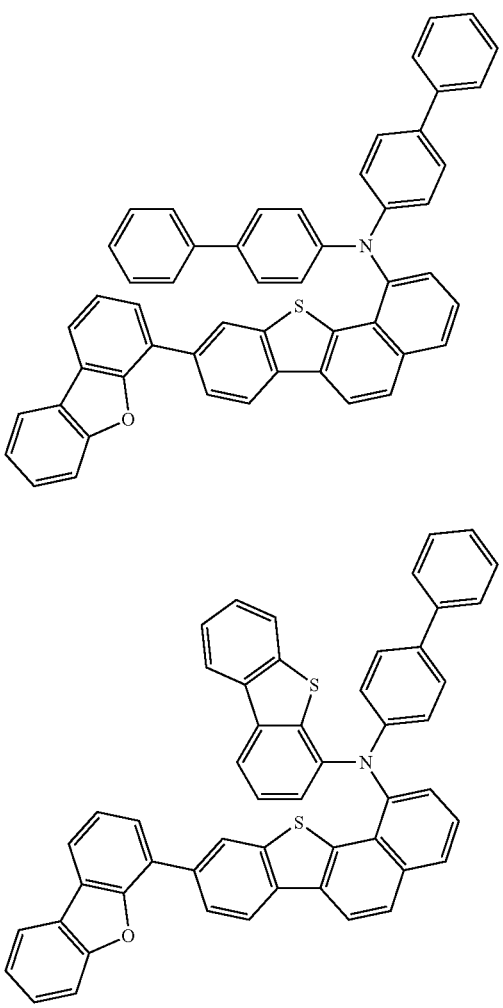
97
98
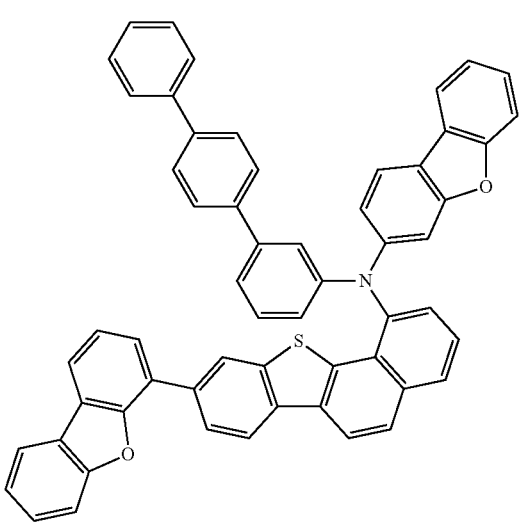

143
-continued
99
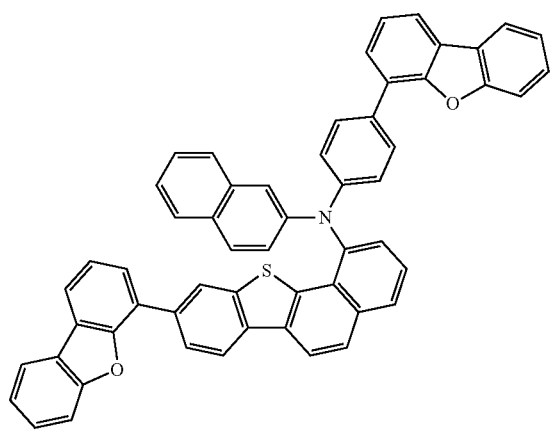
144
-continued
100
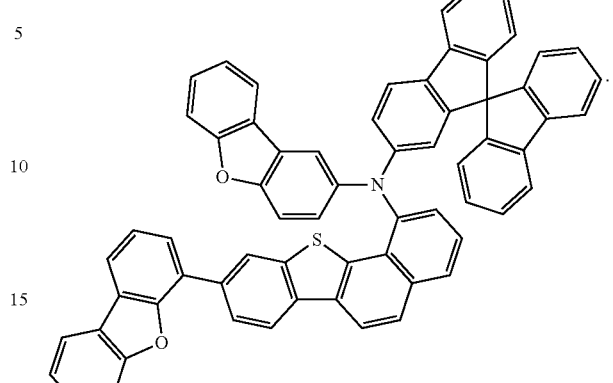
* * * * *

UNITED STATES PATENT AND TRADEMARK OFFICE
CERTIFICATE OF CORRECTION

PATENT NO. : 11,696,497 B2
APPLICATION NO. : 16/724057
DATED : July 4, 2023
INVENTOR(S) : Heejun Park et al.

Page 1 of 2

It is certified that error appears in the above-identified patent and that said Letters Patent is hereby corrected as shown below:

In the Claims

Column 112, Claim 20, Formula 18:

" 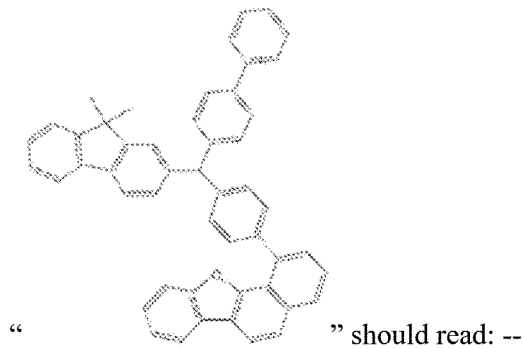 " should read: -- 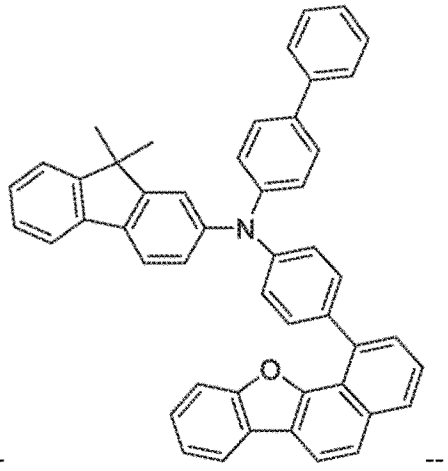 --

Column 117, Claim 20, Formula 26:

Signed and Sealed this
Sixteenth Day of July, 2024

Katherine Kelly Vidal
*Director of the United States Patent and Trademark Office*

CERTIFICATE OF CORRECTION (continued)
U.S. Pat. No. 11,696,497 B2

Page 2 of 2